US012605383B2

(12) United States Patent
Guo et al.

(10) Patent No.: US 12,605,383 B2
(45) Date of Patent: Apr. 21, 2026

(54) METHODS OF TREATING CANCER

(71) Applicant: UNIVERSITY OF PITTSBURGH—OF THE COMMONWEALTH SYSTEM OF HIGHER EDUCATION, Pittsburgh, PA (US)

(72) Inventors: Zong Sheng Guo, Wexford, PA (US); Binfeng Lu, Pittsburgh, PA (US); Zhi Zhu, Shenyang (CN); Hongqi Chen, Shanghai (CN)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 448 days.

(21) Appl. No.: 18/325,648

(22) Filed: May 30, 2023

(65) Prior Publication Data

US 2023/0338384 A1 Oct. 26, 2023

Related U.S. Application Data

(63) Continuation of application No. PCT/US2021/061160, filed on Nov. 30, 2021.

(60) Provisional application No. 63/119,516, filed on Nov. 30, 2020.

(51) Int. Cl.
*A61K 31/519* (2006.01)
*A61K 38/20* (2006.01)
*A61P 35/00* (2006.01)

(52) U.S. Cl.
CPC ............ *A61K 31/519* (2013.01); *A61K 38/20* (2013.01); *A61P 35/00* (2018.01)

(58) Field of Classification Search
CPC .................................................... A61K 31/519
See application file for complete search history.

(56) References Cited

U.S. PATENT DOCUMENTS

2007/0258952 A1 11/2007 Tong et al.
2017/0020938 A1 1/2017 Wang et al.

FOREIGN PATENT DOCUMENTS

WO WO 2019/183266 A1 9/2019

OTHER PUBLICATIONS

Guo, (2019), Journal for Immuno Therapy of Cancer, 7.6, pp. 1-21 (Year: 2019).*
Kyula, (2014) Oncogene, vol. 33, pp. 1700-1712 (Year: 2014).*
Hong, Sep. 24, 2020, N Engl J Med vol. 13, No. 13, p. 1207 to 1217 (Year: 2020).*
Bartlett et al., "Oncolytic viruses as therapeutic cancer vaccines," Mol Cancer 12:103 (2013).
Bommareddy et al., "Integrating oncolytic viruses in combination cancer immunotherapy," Nat Rev Immunol., 18: 498-513 (2018).
Chakrabarti et al., "Compact, Synthetic, Vaccinia Virus Early/Late Promoter for Protein Expression," Biotechniques 23:1094-1097 (1997).

(Continued)

*Primary Examiner* — Mark L Shibuya
(74) *Attorney, Agent, or Firm* — Baker Botts L.L.P.

(57) ABSTRACT

The present disclosure relates to the use of a KRAS inhibitor and an oncolytic virus to prevent and/or treat cancer. The methods include prevention and/or treatment of cancer with the administration of a KRAS inhibitor and an oncolytic virus to a subject. The present disclosure further provides kits for performing such methods.

10 Claims, 65 Drawing Sheets

Specification includes a Sequence Listing.

(56) References Cited

OTHER PUBLICATIONS

Cochran et al., "In Vitro Mutagenesis of the Promoter Region for a Vaccinia Virus Gene: Evidence for Tandem Early and Late Regulatory Signals," J. Virol. 54:30-37 (1985).
Fell et al., "Identification of the Clinical Development Candidate MRTX849, a Covalent KRASG12C Inhibitor for the Treatment of Cancer," J Med Chem., 63: 6679-6693 (2020).
Guo et al., "Oncolytic immunotherapy: dying the right way is a key to eliciting potent antitumor immunity," Front Oncol., 4: 74 (2014).
Harrington et al., "Optimizing oncolytic virotherapy in cancer treatment," Nat Rev Drug Discov. 2019; 18: 689-706 (2019).
International Search Report and Written Opinion dated Mar. 21, 2022 corresponding to International Patent Application No. PCT/US2021/061160.
Jiao et al., "Overcoming resistance to drugs targeting $KRAS^{G12C}$ mutation," The Innovation, 1, 100035 (2020).
Lawler et al., "Oncolytic viruses in cancer treatment: a review," JAMA Oncology, 3.6: 841-849 (2017).
Myers et al., "Optimal alignments in linear space," Comput. Appl. Biosci., 4:11-17 (1988).
Needleman et al., "A General Method Applicable to the Search for Similarities in the Amino Acid Sequence of Two Proteins," J. Mol. Biol. 48:444-453 (1970).
Wang et al., "IL-36γ Transforms the Tumor Microenvironment and Promotes Type 1 Lymphocyte-Mediated Antitumor Immune Responses," Cancer Cell 28: 296-306 (2015).

* cited by examiner

SEQUENCE LISTING

```
Sequence total quantity: 4
SEQ ID NO: 1            moltype = AA  length = 134
FEATURE                 Location/Qualifiers
source                  1..134
                        mol_type = protein
                        organism = Homo sapiens
SEQUENCE: 1
MRGTPGDADG GGRAVYQSIT VAVITCKYPE ALEQGRGDPI YLGIQNPEMC LYCEKVGEQP  60
TLQLKEQKIM DLYGQPEPVK PFLFYRAKTG RTSTLESVAF PDWFIASSKR DQPIILTSEL  120
GKSYNTAFEL NIND                                                    134

SEQ ID NO: 2            moltype = DNA  length = 402
```

-continued

```
FEATURE                Location/Qualifiers
source                 1..402
                       mol_type = other DNA
                       organism = Homo sapiens
SEQUENCE: 2
atgcgcggca ccccgggcga tgcggatggc ggcggccgcg cggtgtatca gagcattacc  60
gtggcggtga ttacctgcaa atatccggaa gcgctggaac agggccgcgg cgatccgatt  120
tatctgggca ttcagaaccc ggaaatgtgc ctgtattgcg aaaaagtggg cgaacagccg  180
accctgcagc tgaaagaaca gaaaattatg gatctgtatg gccagccgga accggtgaaa  240
ccgtttctgt tttatcgcgc gaaaaccggc cgcaccagca ccctggaaag cgtggcgttt  300
ccggattggt ttattgcgag cagcaaacgc gatcagccga ttattctgac cagcgaactg  360
ggcaaaagct ataacaccgc gtttgaactg aacattaacg at                    402

SEQ ID NO: 3           moltype = AA  length = 169
FEATURE                Location/Qualifiers
source                 1..169
                       mol_type = protein
                       organism = Homo sapiens
SEQUENCE: 3
MRGTPGDADG GGRAVYQSMC KPITGTINDL NQQVWTLQGQ NLVAVPRSDS VTPVTVAVIT  60
CKYPEALEQG RGDPIYLGIQ NPEMCLYCEK VGEQPTLQLK EQKIMDLYGQ PEPVKPFLFY  120
RAKTGRTSTL ESVAFPDWFI ASSKRDQPII LTSELGKSYN TAFELNIND             169

SEQ ID NO: 4           moltype = DNA  length = 507
FEATURE                Location/Qualifiers
source                 1..507
                       mol_type = other DNA
                       organism = Homo sapiens
SEQUENCE: 4
atgcgcggca ccccgggcga tgcggatggc ggcggccgcg cggtgtatca gagcatgtgc  60
aaaccgatta ccggcaccat taacgatctg aaccagcagg tgtggaccct gcagggccag  120
aacctggtgg cggtgccgcg cagcgatagc gtgaccccgg tgaccgtggc ggtgattacc  180
tgcaaatatc cggaagcgct ggaacagggc cgcggcgatc cgatttatct gggcattcag  240
aacccggaaa tgtgcctgta ttgcgaaaaa gtgggcgaac agccgaccct gcagctgaaa  300
gaacagaaaa ttatggatct gtatggccag ccggaaccgg tgaaaccgtt tctgttttat  360
cgcgcgaaaa ccggccgcac cagcaccctg gaaagcgtgg cgtttccgga ttggtttatt  420
gcgagcagca aacgcgatca gccgattatt ctgaccagcg aactgggcaa aagctataac  480
accgcgtttg aactgaacat taacgat                                     507
```

METHODS OF TREATING CANCER

CROSS-REFERENCE TO RELATED APPLICATIONS

This application is a continuation of International Patent Application No. PCT/US2021/061160, filed Nov. 30, 2021, which claims priority to U.S. Provisional Application No. 63/119,516, filed on Nov. 30, 2020, the contents of each of which are incorporated in their entirety, and to each of which priority is claimed.

STATEMENT OF GOVERNMENT RIGHTS

This invention was made with government support under CA205727 awarded by the National Institutes of Health (NIH). The government has certain rights in the invention.

SEQUENCE LISTINGS

The instant application contains a Sequence Listings, which has been submitted in XML format via EFS-Web and is hereby incorporated by reference in its entirety. Said XML copy, created on May 30, 2023, is named 072396_960_SL.xml and is 5,665 bytes in size.

FIELD OF INVENTION

The present disclosure relates to the use of combinatorial therapies to prevent and/or treat cancers.

BACKGROUND

Some cancers may have very limited treatment options, particularly when the cancer expresses specific mutations of oncogenes. KRAS has been one of the most challenging oncogenes in cancer. Cancers driven by KRAS mutations are both common and deadly. $KRAS^{G12C}$ is an oncogenic driver mutation in multiple cancer types, including lung, colorectal, and pancreatic cancers. About 45% of all non-small-cell lung carcinoma (NSCLC) KRAS mutations in the US are $KRAS^{G12C}$, which represents 25,000 NSCLC patients each year. Despite advances in treatments such as, for example, surgery, chemotherapy, and radiation therapy, the prognosis for many cancers with KRAS mutations may be poor. Accordingly, there exists an unmet need for additional cancer treatments.

SUMMARY

The present disclosure provides methods and compositions for treating cancer in a subject.

In one aspect, the present disclosure provides a method for treating a cancer in a subject in need thereof, comprising administering a therapeutically effective amount of a KRAS inhibitor and a therapeutically effective amount of an oncolytic virus to the subject.

In certain embodiments, the KRAS inhibitor is administered orally. In certain embodiments, the KRAS inhibitor comprises KRpep-2d, lonafarnib, BI-3406, BAY-293, BI-2852, oncrasin-1, MRTX849, MRTX1257, K-Ras-IN-1, sotorasib, AMG510, ARS-1620, fendiline hydrochloride, deltarasin, K-Ras inhibitor 9, K-Ras inhibitor 6, K-Ras inhibitor 12, 6H05, salts thereof, derivatives thereof, or a combination thereof. In certain embodiments, the KRAS inhibitor comprises MRTX849, MRTX1257, AMG510, or a combination thereof. In certain embodiments, the KRAS inhibitor is MRTX849. In certain embodiments, the KRAS inhibitor is MRTX1257. In certain embodiments, the KRAS inhibitor is AMG510. In certain embodiments, the oncolytic virus comprises a nucleic acid molecule encoding interleukin-36γ (IL-36γ). In certain embodiments, the IL-36γ is a human IL-36γ or a mouse IL-36γ. In certain embodiments, the IL-36γ is a recombinant IL-36γ. In certain embodiments, the IL-36γ comprises an amino acid sequence that is at least 80% identical to the amino acid sequence set forth in SEQ ID NO: 1. In certain embodiments, the IL-36γ comprises the amino acid sequence set forth in SEQ ID NO: 1. In certain embodiments, the IL-36γ comprises an amino acid sequence that is at least 80% identical to the amino acid sequence set forth in SEQ ID NO: 3. In certain embodiments, the IL-36γ comprises the amino acid sequence set forth in SEQ ID NO: 3.

In certain embodiments, the nucleic acid molecule is an exogenous nucleic acid molecule. In certain embodiments, the nucleic acid molecule is integrated into the genome of the oncolytic virus. In certain embodiments, the nucleic acid molecule is a DNA molecule. In certain embodiments, the nucleic acid molecule is operably linked to a promoter.

In certain embodiments, the oncolytic virus is an oncolytic vaccinia virus. In certain embodiments, the promoter is a vaccine virus promoter. In certain embodiments, the vaccine virus promoter is p7.5 or pSE/L.

In certain embodiments, the oncolytic vaccinia virus lacks the expression of a functional thymidine kinase (TK), a functional vaccinia growth factor (VGF), a functional serine proteinase inhibitor 1 (SPI-1), a functional serine proteinase inhibitor 2 (SPI-2), or a combination thereof. In certain embodiments, the oncolytic vaccinia virus comprises a mutation of the J2R gene, a mutation of the C11R gene, a mutation of the B22R gene, a mutation of the B13R gene, or a combination thereof. In certain embodiments, the nucleic acid molecule is integrated into the locus of the J2R gene. In certain embodiments, the oncolytic vaccinia virus is a Western Reserve strain.

In certain embodiments, the KRAS inhibitor is administered to the subject at a dose from about 0.05 mg/kg to about 100 mg/kg. In certain embodiments, the oncolytic virus is administered to the subject at a dose from about $10^5$ and $10^{10}$ plaque forming units (PFU).

In certain embodiments, the method further comprises administering an immunomodulatory agent to the subject. In certain embodiments, the immunomodulatory agent is selected from the group consisting of immune checkpoint inhibitors, T cells, dendritic cells, therapeutic antibodies, cancer vaccines, cytokines, Bacillus Calmette-Guérin (BCG), and a combination thereof.

In certain embodiments, the immunomodulatory agent is an immune checkpoint inhibitor. In certain embodiments, the immune checkpoint inhibitor is selected from the group consisting of anti-PD1 antibodies, anti-PD-L1 antibodies, anti-CTLA-4 antibodies, anti-BTLA antibodies, anti-TIM3 antibodies, anti-LAG-3 antibodies, and a combination thereof. In certain embodiments, the immune checkpoint inhibitor is an anti-PD1 antibody.

In certain embodiments, the method improves the anti-cancer adaptive immune response in the subject. In certain embodiments, the method promotes the immunogenicity of a tumor microenvironment of the subject.

In certain embodiments, the cancer is selected from the group consisting of adenocarcinomas, osteosarcomas, cervical carcinomas, melanomas, hepatocellular carcinomas, breast cancers, lung cancers, prostate cancers, ovarian cancers, leukemia, lymphomas, renal carcinomas, pancreatic cancers, gastric cancers, colon cancers, duodenal cancers, glioblastoma multiforme, astrocytomas, sarcomas, and a combination thereof. In certain embodiments, the cancer is selected from the group consisting of pancreatic cancers, colorectal cancers, melanomas, and a combination thereof. In certain embodiments, the subject is a human subject.

In another aspect, the present disclosure provides a KRAS inhibitor and an oncolytic virus for use in the treatment of a cancer in a subject.

In certain embodiments, the KRAS inhibitor is an oral KRAS inhibitor. In certain embodiments, the KRAS inhibitor comprises KRpep-2d, lonafarnib, BI-3406, BAY-293, BI-2852, oncrasin-1, MRTX849, MRTX1257, K-Ras-IN-1, sotorasib, AMG510, ARS-1620, fendiline hydrochloride, deltarasin, K-Ras inhibitor 9, K-Ras inhibitor 6, K-Ras inhibitor 12, 6H05, a salt thereof, a derivative thereof, or a combination thereof. In certain embodiments, the KRAS inhibitor comprises MRTX849, MRTX1257, AMG510, or a combination thereof. In certain embodiments, the KRAS inhibitor is MRTX849. In certain embodiments, the KRAS inhibitor is MRTX1257. In certain embodiments, the KRAS inhibitor is AMG510.

In certain embodiments, the oncolytic virus comprises a nucleic acid molecule encoding interleukin-36γ (IL-36γ). In certain embodiments, the IL-36γ is a human IL-36γ or a mouse IL-36γ. In certain embodiments, the IL-36γ is a recombinant IL-36γ. In certain embodiments, the IL-36γ comprises an amino acid sequence that is at least 80% identical to the amino acid sequence set forth in SEQ ID NO: 1. In certain embodiments, the IL-36γ comprises the amino acid sequence set forth in SEQ ID NO: 1. In certain embodiments, the IL-36γ comprises an amino acid sequence that is at least 80% identical to the amino acid sequence set forth in SEQ ID NO: 3. In certain embodiments, the IL-36γ comprises the amino acid sequence set forth in SEQ ID NO: 3.

In certain embodiments, the nucleic acid molecule is an exogenous nucleic acid molecule. In certain embodiments, the nucleic acid molecule is integrated into the genome of the oncolytic virus. In certain embodiments, the nucleic acid molecule is a DNA molecule. In certain embodiments, the nucleic acid molecule is operably linked to a promoter. In certain embodiments, the oncolytic virus is an oncolytic vaccinia virus. In certain embodiments, the promoter is a vaccine virus promoter. In certain embodiments, the vaccine virus promoter is p7.5 or pSE/L.

In certain embodiments, the oncolytic vaccinia virus lacks the expression of a functional thymidine kinase (TK), a functional vaccinia growth factor (VGF), a functional serine proteinase inhibitor 1 (SPI-1), a functional serine proteinase inhibitor 2 (SPI-2), or a combination thereof. In certain embodiments, the oncolytic vaccinia virus comprises a mutation of the J2R gene, a mutation of the C11R gene, a mutation of the B22R gene, a mutation of the B13R gene, or a combination thereof. In certain embodiments, the nucleic acid molecule is integrated into the locus of the J2R gene. In certain embodiments, the oncolytic vaccinia virus is a Western Reserve strain.

In certain embodiments, the KRAS inhibitor is administered to the subject at a dose from about 0.05 mg/kg to about 100 mg/kg. In certain embodiments, the oncolytic virus is administered to the subject at a dose from about $10^5$ and $10^{10}$ plaque forming units (PFU).

In certain embodiments, the subject has received or is receiving an immunomodulatory agent. In certain embodiments, the immunomodulatory agent is selected from the group consisting of immune checkpoint inhibitors, T cells, dendritic cells, therapeutic antibodies, cancer vaccines, cytokines, Bacillus Calmette-Guérin (BCG), and a combination thereof. In certain embodiments, the immunomodulatory agent is an immune checkpoint inhibitor. In certain embodiments, the immune checkpoint inhibitor is selected from the group consisting of anti-PD1 antibodies, anti-PD-L1 antibodies, anti-CTLA-4 antibodies, anti-BTLA antibodies, anti-TIM3 antibodies, anti-LAG-3 antibodies, and a combination thereof. In certain embodiments, the immune checkpoint inhibitor is an anti-PD1 antibody.

In certain embodiments, the cancer is selected from the group consisting of adenocarcinomas, osteosarcomas, cervical carcinomas, melanomas, hepatocellular carcinomas, breast cancers, lung cancers, prostate cancers, ovarian cancers, leukemia, lymphomas, renal carcinomas, pancreatic cancers, gastric cancers, colon cancers, duodenal cancers, glioblastoma multiforme, astrocytomas, sarcomas, and a combination thereof. In certain embodiments, the cancer is selected from the group consisting of pancreatic cancers, colorectal cancers, melanomas, and a combination thereof Finally, in another aspect, the present disclosure provides a kit for treating and/or preventing a cancer in a subject, comprising a KRAS inhibitor and an oncolytic virus. In certain embodiments, the kit further comprises an immunomodulatory agent.

In certain embodiments, the KRAS inhibitor is selected from the group consisting of KRpep-2d, lonafarnib, BI-3406, BAY-293, BI-2852, oncrasin-1, MRTX849, K-Ras-IN-1, sotorasib, AMG510, ARS-1620, fendiline hydrochloride, deltarasin, K-Ras inhibitor 9, K-Ras inhibitor 6, K-Ras inhibitor 12, 6H05, salts thereof, or derivatives thereof. In certain embodiments, the oncolytic virus comprises a nucleic acid molecule encoding interleukin-36γ (IL-36γ). In certain embodiments, the immunomodulatory agent is an anti-PD1 antibody.

BRIEF DESCRIPTION OF THE DRAWINGS

FIG. 1A shows the schematic presentation of vvTD and vvTD-IL36γ viral constructs. TKr, the right portion of the tk gene; TK1, the left portion of the tk gene. FIG. 1B shows cancer cell susceptibility towards MRTX1257. The KRASG12C mutant cancer cell lines include murine lung cancer LLC, mesothelioma AE17 and human lung cancer H2122, while non-KRASG12C mutant cancer cell lines include murine colon MC38 and human lung cancer A549. Cancer cells were plated in 96-well plates overnight and then cultured in the presence of drug at concentrations from 0, 0.016 up to 750 nM for duration of 48 h and cell viability was assessed by a CCK8 assay. FIG. 1C shows cytotoxicity induced by OVs for the KRASG12C mutant and non-mutant cancer cells. Cancer cells were infected with vvTD-IL36γ at various MOIs from 0, 0.001 to 100, and cell viability was measured at 48 h post infection. Data are representative of at least triplicates. The value for viable cells at MOI=0 were set at 100%. FIG. 1D shows cell killing activity of vvTD and vvTD-IL36γ combined with MRTX1257 in LLC cells. FIG. 1E shows cell killing activity of vvTD and vvTD-IL36γ combined with MRTX1257 in AE17 cells. FIG. 1F shows cell killing activity of vvTD and vvTD-IL36γ combined with MRTX1257 in H122 cells. FIG. 1G shows cell killing activity of vvTD and vvTD-IL36γ combined with MRTX1257 in MC38 cells. FIG. 1H shows cell killing activity of vvTD and vvTD-IL36γ combined with MRTX1257 in A549 cells. Cell killing activity of vvTD and vvTD-IL36γ combined with MRTX1257. Cancer cells were treated with vvTD or vvTD-IL36γ at MOI of 0.5 and/or 100 nmol MRTX1257 simultaneously. Cytotoxicity was measured at 24, 36, 48 and 72 h. FIG. 1I shows virus titers of LLC cells infected with vvTD or vvTD-IL36γ at MOI of 1 without or with 10 nM MRTX1257 simultaneously. FIG. 1J shows production and secretion of IL-36γ from infected CV1 cells. Cells were mock-infected or infected with vvTD or vvTD-IL36γ at MOI of 1.0, with MRTX1257 alone or in combination, then conditioned media were harvested at 48 h post-infection. The amount of the cytokine protein secreted into the medium was quantified by an ELISA assay.

FIG. 2A shows tumor size of LLC tumors in B6 mice with or without administration of MRTX1257. FIG. 2B shows tumor size of AE17 mesothelioma in B6 mice with or without administration of MRTX1257. FIG. 2C shows tumor size of MC38 colon cancer in B6 mice with or without administration of MRTX1257. FIG. 2D shows survival of B6 mice with LLC tumors with or without administration of MRTX1257. FIG. 2E shows survival of B6 mice with AE17 mesothelioma with or without administration of MRTX1257. FIG. 2F shows survival of B6 mice with MC38 colon cancer with or without administration of MRTX1257.

FIG. 3A shows the tumor size growth curves of LLC tumors in mice. FIG. 3B shows the survival curves of LLC tumors in mice. FIG. 3C shows the tumor size growth curves of AE17 tumors in mice. FIG. 3D shows the survival curves of AE17 tumors in mice.

FIG. 4A shows CD4+ and CD8+ T cells on days 6 and 11 post-therapy. FIG. 4B shows percentages of CD4+ T cells in CD45+ cell populations on these time points. FIG. 4C shows percentages of CD8+ T cells in CD45+ cell populations on these time points. FIG. 4D shows relative quantities of CD4 in TME on day 6 as analyzed by RT-qPCR. FIG. 4E shows relative quantities of CD8 in TME on day 6 as analyzed by RT-qPCR. FIG. 4F shows relative quantities of NKG2D in TME on day 6 as analyzed by RT-qPCR. FIG. 4G shows relative quantities of INF-γ in TME on day 6 as analyzed by RT-qPCR. FIG. 4H shows relative quantities of Granzyme B in TME on day 6 as analyzed by RT-qPCR. FIG. 4I shows relative quantities of IL-36γ in TME on day 6 as analyzed by RT-qPCR.

FIG. 5A shows levels of NK cells (NKG2D+CD3−). FIG. 5O shows levels of regulatory T cells (CD4+Foxp3+). Four to five mice were used for each treatment group and ANOVA (Tukey's multiple comparisons) test was used to compare respectively. *P<0.05; P<0.01; *P<0.001; and ****P<0.0001. ns: not significant.

FIG. 6A shows a schedule of the antibody immune cell depletion. FIG. 6B shows tumor size progression. FIG. 6C shows long-term survival of mice. FIG. 6D shows tumor size of tumors treated with combinatorial therapy. FIG. 6E shows tumor size of tumors treated with combinatorial therapy.

FIG. 7A shows representative images of IFN-γ ELISpot assay of $2.0\times10^4$ CD90.2+ T cells from tumor tissues (TILs) on day 7 post oncolytic virotherapy or drug treatment and co-cultured 1:1 with specific (LLC) and unspecific (MC38) target cells. FIG. 7B shows the quantification of FIG. 7A. FIG. 7C shows representative images of IFN-γ ELISpots of $1.0\times10^5$ CD90.2+ T cells isolated from the spleen on day 7 post oncolytic virotherapy or drug treatment, and co-cultured 1:1 with specific (LLC) and unspecific (MC38 tumor cells, medium, or splenocytes) target cells. FIG. 7D shows the quantification of FIG. 7C. FIG. 7E shows flow cytometric plots of 4-1BB+CD8+ T cells in the tumor tissues at day 11 post oncolytic virotherapy and/or drug treatment. FIG. 7F shows data of FIG. 7E. FIG. 7G shows flow cytometric plots of 4-1BB+CD4+ T cells in the tumor tissues at day 11 post oncolytic virotherapy and/or drug treatment. FIG. 7H shows data of FIG. 7G.

FIG. 8A shows effector memory T cells subpopulations of CD8+

T cells within the gated CD45+ population in tumors. FIG. 8B shows representative flow cytometric plots and percentages of Macrophages (CD11c+F4/80+) within the gated CD45+ population in tumors. FIG. 8C shows M1, M2-like Macrophages subpopulations (CD11c+F4/80+) within the gated CD45+ population in tumors. FIG. 8D shows PD-1 levels within the gated CD8+ T cells population in tumors. FIG. 8E shows TIM-3 levels within the gated CD8+ T cells population in tumors. FIG. 8F shows CTLA-4 levels within the gated CD8+ T cells population in tumors. FIG. 8G shows PD-1 levels within the gated CD8+ T cells population in tumors FIG. 8H shows NK cells (NKG2D+CD3−) within the gated CD45+ population. FIG. 8I shows DC cells (CD11c+CD11b+) within the gated CD45+ population. FIG. 8J shows exhausted CD8+ T cell (PD1highTIM3+CD8+) (J). FIG. 8K shows regulatory T cells (CD4+Foxp3+). FIG. 8L shows myeloid-derived suppressor cells within the gated CD45+ population.

FIG. 9A shows levels of NK cells (NKG2D+CD3−). FIG. 9O shows levels of myeloid-derived suppressor cells (O).

DETAILED DESCRIPTION

Figure 1A:
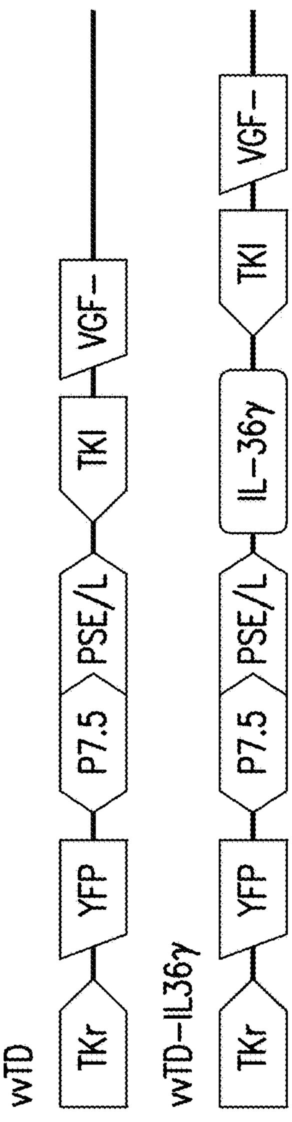
FIGS. 1A-1J illustrate the cytotoxicity of MRTX1257 and OVs in KRASG12C mutant and non-mutant cancer cells in vitro.

The present disclosure relates to composition and methods useful in connection with the use of a combinatorial therapy comprising KRAS inhibitors to prevent and/or treat cancer.

The present disclosure is based, in part, on the discovery that a combinatorial treatment comprising KRAS inhibitors and oncolytic viruses can induce the immune response against cancer cells.

For purposes of clarity of disclosure and not by way of limitation, the detailed description is divided into the following subsections:

1. Definitions;
2. KRAS Inhibitors;
3. Oncolytic Viruses;
4. Methods of Treatment; and
5. Kits.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the use of the word "a" or "an" when used in conjunction with the term "comprising" in the claims and/or the specification can mean "one," but it is also consistent with the meaning of "one or more," "at least one," and "one or more than one."

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of", and "consisting essentially of" the embodiments or elements presented herein, whether explicitly set forth or not.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ. In certain embodiments, the disease is a cancer.

An "effective amount" or "therapeutically effective amount" is an amount effective, at dosages and for periods of time necessary, that produces a desired effect, e.g., the desired therapeutic or prophylactic result. In certain embodiments, an effective amount can be formulated and/or administered in a single dose. In certain embodiments, an effective amount can be formulated and/or administered in a plurality of doses, for example, as part of a dosing regimen.

As used herein, the term "derivative" refers to a chemical compound with a similar core structure. For example, trichloromethane (chloroform) is a derivative of methane.

The term "enantiomers" refers to a pair of stereoisomers that are non-superimposable mirror images of each other. A 1:1 mixture of a pair of enantiomers is a "racemic" mixture or a racemate. The term is used to designate a racemic mixture where appropriate.

The term "enantiopure" refers to a sample that within the limits of detection consists of a single enantiomer.

The term "diastereoisomers" refers to stereoisomers that have at least two asymmetric atoms, but which are not mirror-images of each other. The absolute stereochemistry is specified according to the Cahn-Ingold-Prelog R—S system. When a compound is a pure enantiomer, the stereochemistry at each chiral carbon can be specified by either R or S.

Resolved compounds whose absolute configuration is unknown can be designated (+) or (−) depending on the direction (dextro or levorotatory) in which they rotate plane polarized light at the wavelength of the sodium D line.

The term "isomers" refers to different compounds that have the same molecular formula but differ in arrangement and configuration of the atoms. Also, as used herein, the term "stereoisomer" refers to any of the various stereo isomeric configurations which can exist for a given compound of the presently disclosed subject matter and includes geometric isomers. It is understood that a substituent can be attached at a chiral center of a carbon atom. Also, as used herein, the terms "constitutional isomers" refers to different compounds that have the same numbers of, and types of, atoms but the atoms are connected differently.

"Inhibitors" or "antagonists," as used herein, refer to modulating compounds that reduce, decrease, block, prevent, delay activation, inactivate, desensitize or down-regulate the biological activity and/or expression of a receptor or pathway of interest. The term "antagonist" includes full, partial, and neutral antagonists as well as inverse agonists.

The term "nucleic acid molecule" and "nucleotide sequence," as used herein, refers to a single or double-stranded covalently-linked sequence of nucleotides in which the 3' and 5' ends on each nucleotide are joined by phosphodiester bonds. The nucleic acid molecule can include deoxyribonucleotide bases or ribonucleotide bases, and can be manufactured synthetically in vitro or isolated from natural sources.

The terms "polypeptide," "peptide," "amino acid sequence" and "protein," used interchangeably herein, refer to a molecule formed from the linking of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis or enzymatic synthesis. The terms can apply to amino acid polymers in which one or more amino acid residue is an artificial chemical mimetic of a corresponding naturally occurring amino acid, as well as to naturally occurring amino acid polymers and non-naturally occurring amino acid polymers. In certain embodiments, the polypeptide can have one or more conservative amino acid substitutions. As used herein, "conservative amino acid substitution(s)" are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. Amino acids can also be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. In certain embodiments, no more than one, no more than two, no more than three, no more than four, no more than five residues within a specified sequence are altered. Exemplary conservative amino acid substitutions are shown in Table 1 below.

TABLE 1

| Original Residue | Exemplary Conservative Amino Acid Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gin (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "disease" refers to any condition or disorder that damages or interferes with the normal function of a cell, tissue, or organ.

As used herein, the term "treating" or "treatment" refers to clinical intervention in an attempt to alter the disease course of the individual or cell being treated and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing a cancer, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment can prevent the onset of the disorder or a symptom of the disorder in a subject at risk for the disorder or suspected of having the disorder.

2. KRAS Inhibitors

The present disclosure provides KRAS inhibitors for use in the methods disclosed herein. The KRAS gene is a proto-oncogene encoding the K-Ras protein. K-Ras protein is a GTPase, which acts as a molecular on/off switch, using protein dynamics. Once it is allosterically activated, it recruits and activates proteins necessary for the propagation of growth factors, as well as other cell signaling receptors like c-Raf and PI 3-kinase. K-Ras can upregulate the Glut11 glucose transporter, thereby contributing to the Warburg effect in cancer cells. K-Ras binds to GTP in its active state. It also possesses an intrinsic enzymatic activity that cleaves the terminal phosphate of the nucleotide, converting it to GDP.

The KRAS gene can have mutations that play a role in some of the most common and deadly carcinomas, including lung, colorectal, and pancreatic cancers. Table 2 below provides representative targets and functions regulated by K-Ras.

TABLE 2

| K-Ras effector pathways | Main function of the K-Ras signalling pathways | Oncogenic K-Ras perturb the intrinsic biochemical properties of cell pathways |
|---|---|---|
| MAPK | Proliferation | Increase |
| PI3K/AKT | Survival | |
| NORE1/RASSF1 | Apoptosis | Deregulation |
| RAL-GDS | Membrane vesicle trafficking | |
| JAK/STAT3 | Growth arrest and differentiation | |
| TIAM1/RAC | Cytoskeletal organization | |
| PLCε/PKC | Calcium transport signaling | |
| AF6 | Cell-cell junctions | |
| PKCξ | Transcription | |
| PI3K/PDK1 | Translation | |

The most frequent mutations of KRAS occur at codon 12 (i.e., G12A/C/D/F/L/R/SN), which accounts for 98% of mutations. One of the most common KRAS mutations is G12C (KRAS G12C), which is a single point mutation with a glycine-to-cysteine substitution at codon 12. In addition, less frequent (<1%) mutations are also observed at codon 13 (i.e., G13C/D/P/S) and codon 61 (Q61H/K/R). These substitutions favor the activated state of K-Ras, amplifying signaling pathways that lead to oncogenesis.

A KRAS inhibitor can be a molecule, e.g., chemical compound, that inhibits the activation of K-Ras. A KRAS inhibitor can be a molecule, e.g., chemical compound, that inhibits the functions of K-Ras. A KRAS inhibitor can reversibly or irreversibly inhibit the biological process activated by K-Ras resulting in decreased aggregated cancer cell mass, cancer cell growth rate, cancer cell proliferation, tumor mass, tumor volume, tumor weight, tumor cell proliferation, tumor growth rate, and/or tumor metastasis.

In certain embodiments, the KRAS inhibitor is a pan-KRAS inhibitor. A "pan-KRAS inhibitor" is a molecule that inhibits the activation of K-Ras independently of their variants. In certain embodiments, the KRAS inhibitor is selective for mutated KRAS, e.g., KRAS G12C. Non-limiting examples of KRAS inhibitors for use in the present disclosure include KRpep-2d, lonafarnib, BI-3406, BAY-293, BI-2852, BI 1701963, oncrasin-1, MRTX849, MRTX1257, K-Ras-IN-1, sotorasib, AMG510, ARS-1620, fendiline hydrochloride, deltarasin, K-Ras inhibitor 9, K-Ras inhibitor 6, K-Ras inhibitor 12, 6H05, salts thereof, or derivatives thereof. In certain embodiments, the KRAS inhibitor is a pan-inhibitors mutared KRAS. In certain non-limiting embodiments, for example, the KRAS inhibitor can be PHT-7.3 or compound-11.

In certain embodiments, the KRAS inhibitor for use in the present disclosure has the following formula:

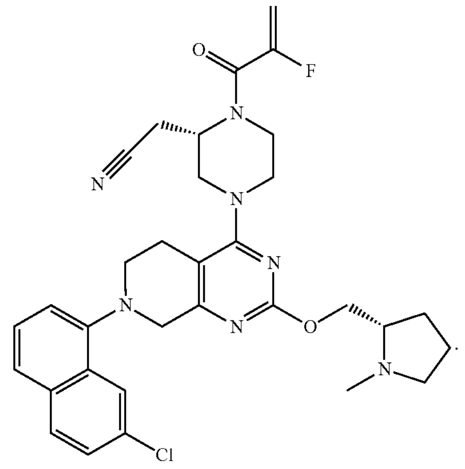 [SMILES: C=C(F)C(=O)N1CCN(c2nc(OC[C@@H]3CCCN3C)nc3c2CCN(c2cccc4ccc(Cl)cc24)C3)C[C@@H]1CC#N]

In certain embodiments, the KRAS inhibitor for use in the present disclosure has the following formula:

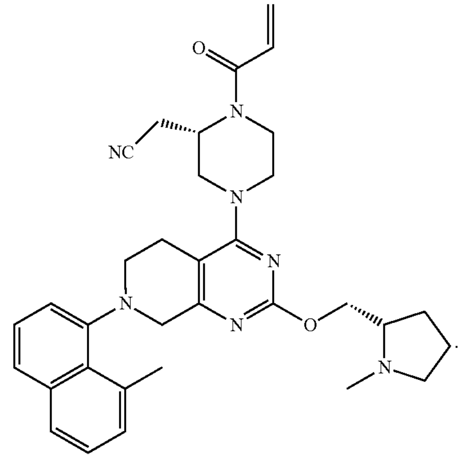

In certain embodiments, the KRAS inhibitor for use in the present disclosure has the following formula:

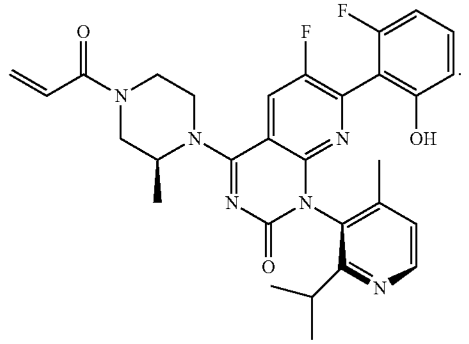

In certain non-limiting embodiments, the present disclosure further provides pharmaceutical formulations of KRAS inhibitors for therapeutic use. In certain embodiments, the pharmaceutical formulation includes a KRAS inhibitor and a pharmaceutically acceptable carrier. "Pharmaceutically acceptable," as used herein, includes any carrier which does not interfere with the effectiveness of the biological activity of the active ingredients, e.g., KRAS inhibitor, and that is not toxic to the patient to whom it is administered. Non-limiting examples of suitable pharmaceutical carriers include phosphate-buffered saline solutions, water, emulsions, such as oil/water emulsions, various types of wetting agents and sterile solutions. Additional non-limiting examples of pharmaceutically acceptable carriers can include gels, bioabsorbable matrix materials, implantation elements containing the inhibitor and/or any other suitable vehicle, delivery or dispensing means or material. Such carriers can be formulated by conventional methods and can be administered to the subject.

In certain embodiments, the pharmaceutical formulations of the present disclosure include stereoisomers, enantiomers, diastereomers, or racemates of the KRAS inhibitors. The KRAS inhibitors disclosed herein can contain one or more asymmetric centers and can thus give rise to enantiomers, diastereomers, and other stereoisomeric forms that can be defined, in terms of absolute stereochemistry, as (R)- or (S)-. In certain embodiments, the pharmaceutical formulation of the present disclosure includes all possible isomers, including racemic mixtures, optically pure forms, and intermediate mixtures. Optically active (R)- and (S)-isomers can be prepared using chiral synthons or chiral reagents or resolved using conventional techniques. If the KRAS inhibitor contains a double bond, the substituent can be E or Z configuration. If the compound contains a disubstituted cycloalkyl, the cycloalkyl substituent can have a cis- or trans-configuration. All tautomeric forms are also intended to be included.

In certain embodiments, the pharmaceutical formulations of the present disclosure can be formulated using pharmaceutically acceptable carriers well known in the art that are suitable for parenteral administration, e.g., intravenous administration, intraarterial administration, intrathecal administration, intranasal administration, intramuscular administration, subcutaneous administration and intracisternal administration. In certain embodiments, the pharmaceutical formulation is formulated for intrathecal administration. For example, but not by way of limitation, the pharmaceutical formulation can be formulated as solutions, suspensions or emulsions.

In certain non-limiting embodiments, the pharmaceutical formulations of the present disclosure can be formulated using pharmaceutically acceptable carriers well known in the art that are suitable for oral administration. Such carriers enable the pharmaceutical compositions to be formulated as tablets, pills, capsules, liquids, gels, syrups, slurries, suspensions and the like, for oral ingestion by a patient to be treated. In certain embodiments, the pharmaceutical formulation can be a solid dosage form.

In certain embodiments, the pharmaceutical formulation can be formulated to release the KRAS inhibitor immediately upon administration. Alternatively, the pharmaceutical formulation can be formulated to release the KRAS inhibitor at any predetermined time or time period after administration. Such types of compositions are generally known as controlled release formulations, which include (i) formulations that create substantially constant concentrations of the KRAS inhibitor within the subject over an extended period of time; (ii) formulations that after a predetermined lag time create substantially constant concentrations of the KRAS inhibitor within the subject over an extended period of time; (iii) formulations that sustain the KRAS inhibitor's action during a predetermined time period by maintaining a relatively constant, effective level of the KRAS inhibitor in the body with concomitant minimization of undesirable side effects; (iv) formulations that localize action of KRAS inhibitor, e.g., spatial placement of a controlled release composition adjacent to or in the disease, e.g., cancer cells; (v) formulations that achieve convenience of dosing, e.g., administering the composition once per week or once every two weeks; and (vi) formulations that target the action of the KRAS inhibitor by using carriers or chemical derivatives to deliver the KRAS inhibitor to a particular target cell type or a particular target tissue type. In certain embodiments, controlled release is obtained by appropriate selection of various formulation parameters and ingredients, including, e.g., various types of controlled release compositions and coatings. For example, but not by way of limitation, the KRAS inhibitor can be formulated with appropriate excipients into a pharmaceutical formulation that, upon administration, releases the KRAS inhibitor in a controlled manner, e.g., oil solutions, suspensions, emulsions, microcapsules, molecular complexes, microspheres, nanoparticles, patches and liposomes.

In certain embodiments, the pharmaceutical formulations suitable for use in the present disclosure can include formulations where the KRAS inhibitors are contained in a therapeutically effective amount. A "therapeutically effective amount" refers to an amount that is able to prevent and/or reduce the development, growth, and metastasis of a cancer. The therapeutically effective amount of an active ingredient can vary depending on the active ingredient, e.g., KRAS inhibitor, formulation used, the anatomical location of the cancer and its severity, and the age, weight, etc., of the subject to be treated. In certain embodiments, a patient can receive a therapeutically effective amount of a KRAS inhibitor as a single dose or multiple administrations of two or more doses, which can depend on the dosage and frequency as required and tolerated by the patient. In certain embodiments, the provided methods involve administering the compositions at effective amounts, e.g., therapeutically effective amounts.

3. Oncolytic Viruses

The present disclosure provides oncolytic viruses expressing an interleukin-36 (IL-36) cytokine for use in the methods disclosed herein. In certain embodiments, the oncolytic virus includes a nucleic acid molecule encoding the IL-36 cytokine. In certain embodiments, the nucleic acid molecule is an exogenous nucleic acid molecule. In certain embodiments, the nucleic acid molecule is integrated into the genome of the oncolytic virus.

IL-36 cytokines are members of IL-1 cytokine family, which plays major roles in initiating and promoting inflammation. In certain embodiments, the IL-36 cytokines are IL-36 receptor agonists that can activate IL-36 receptor ("IL-36R") signaling. Non-limiting examples of IL-36 receptor agonists that can be used with the presently disclosed subject matter include IL-36α, IL-36β, and IL-36γ. In certain embodiments, the oncolytic virus disclosed herein includes a nucleic acid molecule encoding an IL-36 cytokine selected from IL-36α, IL-36β, IL-36γ, and combinations thereof. In certain embodiments, the nucleic acid molecule is an exogenous nucleic acid molecule.

In certain embodiments, the oncolytic virus for use in the methods disclosed herein includes a nucleic acid molecule encoding IL-36γ or a functional fragment thereof. In certain embodiments, the nucleic acid molecule encodes a human IL-36γ or a functional fragment thereof. In certain embodiments, the human IL-36γ has an amino acid sequence that is at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homologous or identical to the amino acid sequence set forth in GenBank/NCBI database accession no. NP_001265497.1, or NP_062564.1. In certain embodiments, the nucleic acid molecule encoding the human IL-36γ can contain substitutions (e.g., conservative substitutions), insertions, or deletions relative to the amino acid sequence set forth in GenBank/NCBI database accession no. NP_001265497.1, or NP_062564.1, that do not significantly alter the function or activity of the human IL-36γ.

In certain embodiments, the human IL-36γ polypeptide comprises or consists of an amino acid sequence that is at least about 85%, about 90%, about 95%, about 96%, about 97%, about 98%, about 99% or 100% homologous or identical to the amino acid sequence set forth in SEQ ID NO: 1, which is provided below.

```
                                        (SEQ ID NO: 1)
MRGTPGDADGGGRAVYQSITVAVITCKYPEALEQGRGDPTYLGIQNPEMC

LYCEKVGEQPTLQLKEQKIMDLYGQPEPVKPFLFYRAKTGRTSTLESVAF

PDWFIASSKRDQPIILTSELGKSYNTAFELNIND
```

An exemplary nucleic acid sequence encoding the amino acid sequence of SEQ ID NO: 1 is set forth in SEQ ID NO: 2, which is provided below.

```
                                        (SEQ ID NO: 2)
ATGCGCGGCACCCCGGGCGATGCGGATGGCGGCGGCCGCGCGGTGTATCA

GAGCATTACCGTGGCGGTGATTACCTGCAAATATCCGGAAGCGCTGGAAC

AGGGCCGCGGCGATCCGATTTATCTGGGCATTCAGAACCCGGAAATGTGC

CTGTATTGCGAAAAAGTGGGCGAACAGCCGACCCTGCAGCTGAAAGAACA

GAAAATTATGGATCTGTATGGCCAGCCGGAACCGGTGAAACCGTTTCTGT

TTTATCGCGCGAAAACCGGCCGCACCAGCACCCTGGAAAGCGTGGCGTTT

CCGGATTGGTTTATTGCGAGCAGCAAACGCGATCAGCCGATTATTCTGAC

CAGCGAACTGGGCAAAAGCTATAACACCGCGTTTGAACTGAACATTAACG

AT
```

In certain embodiments, the human IL-36γ polypeptide comprises or consists of an amino acid sequence that is at least about 85%, about 90%, about 95%, about 96%, about 97%, about 98%, about 99% or 100% homologous or identical to the amino acid sequence set forth in SEQ ID NO: 3, which is provided below.

```
                                        (SEQ ID NO: 3)
MRGTPGDADGGGRAVYQSMCKPITGTINDLNQQVWTLQGQNLVAVPRSDS

VTPVTVAVITCKYPEALEQGRGDPTYLGIQNPEMCLYCEKVGEQPTLQLK
```

-continued

```
EQKIMDLYGQPEPVKPFLFYRAKTGRTSTLESVAFPDWFIASSKRDQPII

LTSELGKSYNTAFELNIND
```

An exemplary nucleic acid sequence encoding the amino acid sequence of SEQ ID NO: 3 is set forth in SEQ ID NO: 4, which is provided below.

```
                                        (SEQ ID NO: 4)
ATGCGCGGCACCCCGGGCGATGCGGATGGCGGCGGCCGCGCGGTGTATCA

GAGCATGTGCAAACCGATTACCGGCACCATTAACGATCTGAACCAGCAGG

TGTGGACCCTGCAGGGCCAGAACCTGGTGGCGGTGCCGCGCAGCGATAGC

GTGACCCCGGTGACCGTGGCGGTGATTACCTGCAAATATCCGGAAGCGCT

GGAACAGGGCCGCGGCGATCCGATTTATCTGGGCATTCAGAACCCGGAAA

TGTGCCTGTATTGCGAAAAAGTGGGCGAACAGCCGACCCTGCAGCTGAAA

GAACAGAAAATTATGGATCTGTATGGCCAGCCGGAACCGGTGAAACCGTT

TCTGTTTTATCGCGCGAAAACCGGCCGCACCAGCACCCTGGAAAGCGTGG

CGTTTCCGGATTGGTTTATTGCGAGCAGCAAACGCGATCAGCCGATTATT

CTGACCAGCGAACTGGGCAAAAGCTATAACACCGCGTTTGAACTGAACAT

TAACGAT
```

In certain embodiments, the nucleic acid molecule encodes a mouse, a rat, a dog, or a chimpanzee IL-36γ. In certain embodiments, the mouse, the dog, the rat, or the chimpanzee IL-36γ has an amino acid sequence that is at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homologous or identical to the amino acid sequence set forth in GenBank/NCBI database accession no. NP_705731.2 (mouse), XP_008759827.1 (rat), XP_017447462.1 (rat), XP_022260442.1 (dog), XP_005630506.1 (dog), XP_005630508.1 (dog), XP_024783449.1 (chimpanzee), XP_024783450.1 (chimpanzee), or XP_003804550.1 (chimpanzee). In certain embodiments, the mouse, the dog, the rat, or the chimpanzee IL-36γ can contain substitutions (e.g., conservative substitutions), insertions, or deletions relative to the amino acid sequence set forth in GenBank/NCBI database accession no. NP_705731.2 (mouse), XP_008759827.1 (rat), XP_017447462.1 (rat), XP_022260442.1 (dog), XP_005630506.1 (dog), XP_005630508.1 (dog), XP_024783449.1 (chimpanzee), XP_024783450.1 (chimpanzee), or XP_003804550.1 (chimpanzee), that do not significantly alter the function or activity of the mouse, the dog, the rat, or the chimpanzee IL-36γ.

The nucleic acid molecule encoding an IL-36 cytokine can be a DNA molecule, an RNA molecule, or a cDNA molecule to conform to the nucleic acid of the oncolytic viral genome into which it is integrated.

Any suitable oncolytic viruses can be used with in the methods disclosed herein. Non-limited examples of oncolytic viruses that can be used with the presently disclosed subject matter include Coxsackieviruses, Maraba viruses (rhabdovirus), Parvoviruses, Seneca Valley viruses, vesicular stomatitis viruses (VSVs), Newcastle disease viruses (NDVs), retroviruses, reoviruses, measles viruses, Sindbis viruses, influenza viruses, herpes simplex viruses (HSVs), Sendai viruses, vaccinia viruses (VVs), and adenoviruses, and variants thereof.

In certain embodiments, the oncolytic virus for use in the methods disclosed herein is an oncolytic vaccinia virus. Any suitable strains of vaccinia viruses can be used with the presently disclosed subject matter. Non-limiting examples of vaccinia virus strains for use in the methods disclosed herein include strains of, derived from, or modified forms of Western Reserve (WR) strain, Tashkent strain, Lister strain (also known as Elstree), Dryvax strain (also known as Wyeth strain), IHD-J strain, and IHD-W strain, Brighton strain, Ankara strain, modified vaccinia Ankara (MVA) strain, Dairen strain (e.g., Dairen I strain (DIs)), LIPV strain, lister clone 16m8 (LC16m8) strain, LC16MO strain, LIVP strain, WR 65-16 strain, Connaught strain, New York City Board of Health (NYCBH) strain, EM63 strain, ACAM2000™ strain, CV-1 strain, Paris strain, Copenhagen (Cop) strain, Bern strain, and the Tian Tan (VTT) strain. In certain embodiments, the oncolytic vaccinia virus for use in the methods disclosed herein is a Western Reserve strain.

In certain embodiments, the nucleic acid molecule encoding an IL-36 cytokine is integrated into the genome of the oncolytic virus, where the expression of the nucleic acid molecule is operably linked to a promoter that is active or activatable in an oncolytic virus infected cell, for example, a promoter of the oncolytic virus. As used herein, "operably linked" means that a promoter is in a correct functional location and/or orientation in relation to a nucleic acid locus to control transcriptional initiation and/or expression of that locus.

In certain embodiments, the promoter is a vaccinia virus promoter. In certain embodiments, the vaccinia virus promoter is a synthetic vaccinia promoter. In certain embodiments, the vaccinia virus promoter is a p7.5 promoter, which is a classical early-late promoter (Cochran et al., J. Virol. (1985); 54:30-37, the contents of which are incorporated by reference in its entirety). In certain embodiments, the vaccinia virus promoter is a synthetic promoter (pSE/L) that has been used to direct strong early as well as late gene expression (Chakrabarti et al., Biotechniques (1997); 23:1094-1097, the contents of which are incorporated by reference in its entirety).

In certain embodiments, the oncolytic vaccinia virus disclosed herein lacks the expression of a functional thymidine kinase (TK). TK is encoded by the J2R gene (also known as tk gene), and forms part of the salvage pathway for pyrimidine deoxyribonucleotide synthesis. In certain embodiments, the oncolytic vaccinia virus includes a mutation of the J2R gene. In certain embodiments, the mutation of the J2R gene can be a deletion, a substitution, and/or an insertion of at least one nucleotide of the J2R gene nucleic acid sequence. In certain embodiments, the mutation of the J2R gene includes an insertion of a nucleic acid molecule into the locus of the J2R gene. In certain embodiments, the nucleic acid molecule is an exogenous nucleic acid molecule. In certain embodiments, the nucleic acid molecule encodes an IL-36 cytokine.

In certain embodiments, the oncolytic vaccinia virus disclosed herein lacks the expression of a functional vaccinia growth factor (VGF). VGF is encoded by the C11R gene (also known as vgf gene), and functions by stimulating cellular proliferation around infected cells. In certain embodiments, the oncolytic vaccinia virus includes a mutation in the C11R gene. In certain embodiments, the mutation of the C11R gene can be a deletion, a substitution, and/or an insertion of at least one nucleotide of the C11R gene nucleic acid sequence.

In certain embodiments, the oncolytic vaccinia virus disclosed herein lacks the expression of a functional serine proteinase inhibitor 1 (SPI-1). SPI-1 is encoded by the B22R gene (also known as spi-1 gene), and functions by stimulating cellular proliferation around infected cells. In certain embodiments, the oncolytic vaccinia virus for use in the methods disclosed herein includes a mutation in the B22R gene. In certain embodiments, the mutation of the B22R gene can be a deletion, a substitution, and/or an insertion of at least one nucleotide of the B22R gene nucleic acid sequence.

In certain embodiments, the oncolytic vaccinia virus for use in the methods disclosed herein lacks the expression of a functional serine proteinase inhibitor 2 (SPI-2). SPI-2 is encoded by the B13R gene (also known as spi-2 gene), and functions by stimulating cellular proliferation around infected cells. In certain embodiments, the oncolytic vaccinia virus includes a mutation in the B13R gene. In certain embodiments, the mutation of the B13R gene can be a deletion, a substitution, and/or an insertion of at least one nucleotide of the B13R gene nucleic acid sequence.

In certain embodiments, a mutation in a gene (e.g., the J2R gene, the C11R gene, the B22R gene, the B13R gene) is an inactivating mutation, in which the expression of the gene is significantly decreased, or the product encoded by the gene (e.g., TK, VGF, SPI-1, SPI-2) is rendered nonfunctional, or its ability to function is significantly decreased.

In certain embodiments, the oncolytic vaccinia virus for use in the methods disclosed herein comprises: (a) a nucleic acid molecule encoding an IL-36γ cytokine, and (b) a mutation is selected from a group consisting of a mutation of the J2R gene, a mutation of the C11R gene, a mutation of the B22R gene, a mutation of the B13R gene, and combinations thereof.

In certain embodiments, the IL-36 cytokine expressing oncolytic vaccinia virus disclosed herein lacks the expression of a functional TK. In certain embodiments, the IL-36γ cytokine expressing oncolytic vaccinia virus disclosed herein comprises a mutation of the J2R gene.

In certain embodiments, the IL-36γ cytokine expressing oncolytic vaccinia virus for use in the methods disclosed herein lacks the expressions of a functional TK and a functional VGF. In certain embodiments, the IL-36γ cytokine expressing oncolytic vaccinia virus disclosed herein comprises a mutation of the J2R gene, and a mutation of the C11R gene In certain embodiments, the IL-36γ cytokine expressing oncolytic vaccinia virus disclosed herein lacks the expressions of a functional TK, a functional SPI-1, and a functional SPI-2. In certain embodiments, the IL-36γ cytokine expressing oncolytic vaccinia virus disclosed herein comprises a mutation of the J2R gene, a mutation of the B22R gene, and a mutation of the B13R gene.

In certain non-limiting embodiments, the present disclosure provides pharmaceutical formulations that include an oncolytic virus that expresses an IL-36γ cytokine or a functional fragment thereof. In certain embodiments, the pharmaceutical composition includes an effective amount of the oncolytic virus. In certain embodiments, the pharmaceutical composition can be prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof.

In certain embodiments, the pharmaceutical composition described herein further includes a pharmaceutically acceptable carrier, e.g., an excipient. In certain embodiments, the pharmaceutically acceptable carrier includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically acceptable carriers include gels, bioadsorbable matrix materials, implantation elements containing the oncolytic virus, and any other suitable vehicle, delivery, or dispensing means or material.

In certain embodiments, the pharmaceutically acceptable carrier can be a buffering agent. Non-limiting examples of suitable buffering agents can include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide other calcium salts, and combinations thereof.

In certain embodiments, the oncolytic virus disclosed herein can be propagated in suitable host cells, isolated from host cells, and stored in conditions that promotes stability and integrity of the virus, such that loss of infectivity over time is minimized. In certain embodiments, the oncolytic virus disclosed herein can be stored by freezing or drying, such as by lyophilization. In certain embodiments, prior to administration, the stored oncolytic virus can be reconstituted (if dried for storage) and diluted in a pharmaceutically acceptable carrier for administration.

4. Methods of Treatment

The present disclosure provides methods of treating a subject having cancer. In certain embodiments, the methods include administering to the subject a combinatorial therapy comprising a KRAS inhibitor and an oncolytic virus that expresses an IL-36 cytokine or a functional fragment thereof. For example, but not by way of limitation, the methods can include administering to the subject a KRAS inhibitor disclosed in Section 2 and an oncolytic virus that comprises a nucleic acid that encodes an IL-36γ cytokine, e.g., a human IL-36γ cytokine, or a functional fragment thereof. Additional non-limiting examples of said oncolytic viruses are disclosed in Section 3.

In certain embodiments, the methods disclosed herein reduce aggregated cancer cell mass, reduces cancer cell growth rate, reduces cancer cell proliferation, reduces tumor mass, reduces tumor volume, reduces tumor weight, reduces tumor cell proliferation, reduces tumor growth rate, and/or reduces tumor metastasis in the subject.

In certain embodiments, the methods disclosed herein improve the anti-cancer adaptive immune response in the subject. In certain embodiments, the improved anticancer adaptive immune response is dependent on the presence and levels of CD4+ and CD8+ T cells in the tumor or tumor microenvironment. In certain embodiments, the methods disclosed herein improve adaptive T cell-mediated immune responses.

In certain embodiments, the methods disclosed herein modulates a tumor microenvironment. The tumor microenvironment is the environment surrounding a tumor. A tumor microenvironment includes extracellular matrix (ECM), fibroblasts, neuroendocrine (NE) cells, adipose cells, immune, signaling molecules, and the blood and lymphatic vascular networks. Cellular interactions, crosstalks between cancer and immune cells, and interplays between cells and soluble factors (such as cytokines) in the tumor microenvironment determine a subject's immune response to tumor cells. In certain embodiments, the methods disclosed herein modify the tumor microenvironment. In certain embodiments, the methods disclosed herein promote the immunogenicity of the tumor microenvironment. As used herein, the term "immunogenicity" refers to the ability to induce an immune response against cancer, e.g., cancer cells, tumor cells.

In certain embodiments, the methods disclosed herein increase the levels of lymphocytes and/or dendritic cells in the tumor or the tumor microenvironment. In certain embodiments, the methods disclosed herein do not increase the level of myeloid-derived suppressor cells or M2 type tumor-associated macrophages in the tumor or the tumor microenvironment. In certain embodiments, the methods disclosed herein increase the level of T cells in the tumor or the tumor microenvironment. In certain embodiments, the T cells are selected from the group consisting of tumor antigen-specific CD4+ T cells, tumor antigen-specific CD8+ T cells, viral antigen-specific CD4+ T cells, viral antigen-specific CD8+ T cells, and combinations thereof. In certain embodiments, the methods disclosed herein decrease the level of T regulatory cells in the tumor or the tumor microenvironment.

Methods disclosed herein can be used for treating any suitable cancers. Non-limiting examples of cancers that can be treated by methods disclosed herein include adenocarcinomas, osteosarcomas, cervical carcinomas, melanomas, hepatocellular carcinomas, breast cancers, lung cancers, prostate cancers, ovarian cancers, leukemias, lymphomas, renal carcinomas, pancreatic cancers, gastric cancers, colon cancers, duodenal cancers, glioblastoma multiforme, astrocytomas, sarcomas, and combinations thereof. In certain embodiments, the method disclosed herein can be used for treating pancreatic cancer, colorectal cancer, melanoma, or a combination thereof.

In certain embodiments, the methods disclosed herein can be used for treating any cancers expressing a mutated KRAS gene. A "mutation" is a permanent change in the nucleotide sequence of DNA. In certain non-limiting embodiments, without any limitation, the mutation can be a base substitution, a deletion, or an insertion. In certain embodiments, the base substitution can be a silent substitution, a missense substitution, or a nonsense substitution. In certain embodiments, the mutated KRAS includes a missense substitution. For example, without any limitation, the missense substitution can be G12C, G12D, G12V and G13C. In certain embodiments, the subject is human. In certain embodiments, the subject is a non-human subject, such as, but not limited to, a non-primate, a dog, a cat, a horse, a rabbit, a mice, a rat, a guinea pig, a fowl, a cow, a goat, or a sheep.

In certain embodiments, the methods disclosed herein include administering the oncolytic virus to the subject in an amount of between about 105 and 1010 plaque-forming units (PFU). In certain embodiments, the methods disclosed herein include administering to the subject the oncolytic virus in a single dose, or in multiple doses. In certain embodiments, where the oncolytic virus is administered to the subject in multiple doses, the doses can be administered sequentially, e.g., at daily, weekly, or monthly intervals, or in response to a specific need of the subject.

In certain embodiments, the method disclosed herein comprises administering to the subject a pharmaceutical composition comprising the oncolytic virus disclosed herein (e.g., pharmaceutical compositions disclosed in Section 3).

Any suitable methods of administration can be used with the presently disclosed subject matter for administering the oncolytic virus to the subject having cancer. In certain embodiments, the oncolytic virus disclosed herein is administered systemically. Alternatively or additionally, the oncolytic virus disclosed herein is administered by injection at the site of the cancer, e.g., tumor site. For example, and not by way of limitation, the route of administration can be inhalation, intranasal, intravenous, intraarterial, intrathecal, intratumoral, intraperitoneal, intramuscular, subcutaneous, topical, intradermal, local regional, oral administration, or a combination thereof. In certain embodiments, the oncolytic virus disclosed herein is administered to the subject from a source implanted in the subject. In certain embodiments, the oncolytic virus disclosed herein is administered to the subject by continuous infusion over a selected period of time. In certain embodiments, the oncolytic virus disclosed herein can be administered directly to a tumor site, e.g., via direct intratumoral injection.

In certain embodiments, the methods disclosed herein include administering the KRAS inhibitor to a subject at a dose of about 0.05 mg/kg to about 100 mg/kg. In certain embodiments, a subject can be administered up to about 2,000 mg of the KRAS inhibitor in a single dose or as a total daily dose. For example, but not by way of limitation, a subject can be administered up to about 1,950 mg, up to about 1,900 mg, up to about 1,850 mg, up to about 1,800 mg, up to about 1,750 mg, up to about 1,700 mg, up to about 1,650 mg, up to about 1,600 mg, up to about 1,550 mg, up to about 1,500 mg, up to about 1,450 mg, up to about 1,400 mg, up to about 1,350 mg, up to about 1,300 mg, up to about 1,250 mg, up to about 1,200 mg, up to about 1,150 mg, up to about 1,100 mg, up to about 1,050 mg, up to about 1,000 mg, up to about 950 mg, up to about 900 mg, up to about 850 mg, up to about 800 mg, up to about 750 mg, up to about 700 mg, up to about 650 mg, up to about 600 mg, up to about 550 mg, up to about 500 mg, up to about 450 mg, up to about 400 mg, up to about 350 mg, up to about 300 mg, up to about 250 mg, up to about 200 mg, up to about 150 mg, up to about 100 mg, up to about 50 mg or up to about 25 mg of the KRAS inhibitor in a single dose or as a total daily dose. In certain embodiments, the subject can be administered from about 50 to about 1,000 mg of the KRAS inhibitor in a single dose or a total daily dose. In certain embodiments, a subject can be administered about 1,000 mg of the KRAS inhibitor, e.g., MRTX1257, in a single dose or as a total daily dose. In certain embodiments, a subject can be administered about 25 mg or more of the KRAS inhibitor, e.g., MRTX1257, in a single dose or as a total daily dose.

It is to be understood that, for any particular subject, specific dosage regimes should be adjusted over time according to the individual need and the professional judgment of the person administering or supervising the administration of the KRAS inhibitor. For example, the dosage of the KRAS inhibitor can be increased if the lower dose does not provide sufficient activity in the treatment of a disease or condition described herein. Alternatively, the dosage of the composition can be decreased if the disease is reduced, no longer detectable or eliminated.

In certain embodiments, the KRAS inhibitor can be administered once a day, twice a day, once a week, twice a week, three times a week, four times a week, five times a week, six times a week, once every two weeks, once a month, twice a month, once every other month or once every third month. In certain embodiments, the KRAS inhibitor can be administered twice a week. In certain embodiments, the KRAS inhibitor can be administered once a week. In certain embodiments, the KRAS inhibitor can be administered two times a week for about four weeks and then administered once a week for the remaining duration of the treatment. In certain embodiments, a subject can be administered up to about 1,000 mg of the KRAS inhibitor in a single dose or as a total daily dose two times a week.

In certain embodiments, the period of treatment can be at least one day, at least one week, at least one month, at least two months, at least three months, at least four months, at least five months or at least six months. In certain embodiments, the KRAS inhibitor can be administered until the cancer is no longer detectable.

In certain embodiments, the KRAS inhibitor can be administered to a subject by any route known in the art. In certain embodiments, the KRAS inhibitor can be administered parenterally. In certain embodiments, the KRAS inhibitor can be administered orally, intravenously, intraarterially, intrathecally, intranasally, subcutaneously, intramuscularly and rectally. In certain embodiments, the KRAS inhibitor can be administered intrathecally. For example, but not by way of limitation, the present disclosure provides methods for the prevention and/or treatment of cancer in a subject, e.g., having lung cancer, by oral administration of a KRAS inhibitor.

In certain embodiments, one or more KRAS inhibitors can be used alone or in combination with an oncolytic virus described herein in Section 3. For example, but not by way of limitation, methods of the present disclosure can include administering one or more KRAS inhibitors and an oncolytic virus expressing IL-36. "In combination with," as used herein, means that the KRAS inhibitor and the oncolytic virus are administered to a subject as part of a treatment regimen or plan. In certain embodiments, being used in combination does not require that the KRAS inhibitor and the oncolytic virus are physically combined prior to administration, administered by the same route or that they be administered over the same time frame. In certain embodiments, the oncolytic virus is administered before a KRAS inhibitor. In certain embodiments, the oncolytic virus is administered after a KRAS inhibitor. In certain embodiments, the oncolytic virus is administered simultaneously with a KRAS inhibitor.

4.1 Combinatorial Therapy of Immunotherapy, KRAS Inhibitors and Oncolytic Viruses The present disclosure further provides methods for improving a subject's responsiveness to an immunomodulatory agent, comprising administering to the subject the immunomodulatory agent, a KRAS inhibitor (e.g., KRAS inhibitors disclosed in Section 2, and an oncolytic virus expressing an IL-36 cytokine (e.g., oncolytic viruses disclosed in Section 3), wherein the subject has cancer. For example, but not by way of limitation, a method for improving a subject's responsiveness to an immunomodulatory agent can include administering a KRAS inhibitor, e.g., MRTX1257, and an oncolytic virus that comprises a nucleic acid that encodes an IL-36γ cytokine, e.g., a human IL-36 cytokine, or a functional fragment thereof with an immunomodulatory agent, wherein the subject has cancer.

The present disclosure also provides methods of treating a subject having a cancer, including administering to the subject a KRAS inhibitor (e.g., KRAS inhibitors disclosed in Section 2), an oncolytic virus that expresses an IL-36 cytokine (e.g., oncolytic viruses disclosed in Section 3), and an immunomodulatory agent. For example, but not by way of limitation, a KRAS inhibitor, e.g., MRTX1257, and an oncolytic virus that comprises a nucleic acid that encodes an IL-36γ cytokine, e.g., a human IL-36 cytokine, or a functional fragment thereof can be administered in combination with an immunomodulatory agent to treat a subject that has cancer.

Any suitable immunomodulatory agent that targets components of the immune system to fight cancer can be used with the presently disclosed methods. Non-limiting examples of immunomodulatory agents include immune checkpoint inhibitors, T cells, dendritic cells, therapeutic antibodies (e.g., anti-CD33 antibodies, anti-CD11b antibodies), cancer vaccines, cytokines (e.g., IL-12, GM-CSF, IL-2, IFNβ, IFNγ, MIP-1, MCP-1, IL-8), Bacillus Calmette-Guérin (BCG), and any combinations thereof. In certain embodiments, the immunomodulatory agent is an immune checkpoint inhibitor. In certain embodiments, the immune checkpoint inhibitor is selected from anti-PD1 antibodies, anti-PD-L1 antibodies, anti-CTLA-4 antibodies, anti-BTLA antibodies, anti-TIM3 antibodies, anti-LAG-3 antibodies, and any combinations thereof. Non-limiting examples of anti-PD1 antibodies include pembrolizumab (KEYTRUDA®), nivolumab (OPDIVO®), cemiplimab (LIBTAYO®), and combinations thereof. Non-limiting examples of anti-PD-L1 antibodies include atezolizumab (TECENTRIQ®), avelumab (BAVENCIO®), durvalumab (IMFINZI®), and combinations thereof. Non-limiting examples of anti-CTL4 antibodies include ipilimumab (YERVOY®).

In certain embodiments, the KRAS inhibitor, the oncolytic virus and the immunomodulatory agent can be administered to the subject as part of a treatment regimen. In certain embodiments, the KRAS inhibitor, the oncolytic virus and the immunomodulatory agent can be administered concurrently to the subject. In certain embodiments, the KRAS inhibitor, the oncolytic virus and the immunomodulatory agent can be administered at the same time. In certain embodiments, the KRAS inhibitor, the oncolytic virus and the immunomodulatory agent can be administered sequentially in any order (e.g., the KRAS inhibitor is administered to the subject before the oncolytic virus and the oncolytic virus is administered to the subject before the immunomodulatory agent is administered; or the KRAS inhibitor is administered before the immunomodulatory agent and the oncolytic virus is administered to the subject after the immunomodulatory agent) or at different points in time (e.g., the KRAS inhibitor, the oncolytic virus and the immunomodulatory agent are administered to the subject on the same day but different hours; the KRAS inhibitor, the oncolytic virus and the immunomodulatory agent are administered to the subject in the same week but on different days).

5. Kits

The present disclosure provides kits for use in the disclosed methods. In certain embodiments, a kit can include a first container that includes a KRAS inhibitor or a pharmaceutical formulation thereof. In certain embodiments, the first container can include a single dose of the KRAS inhibitor or multiple doses of the KRAS inhibitor. In certain embodiments, the kit can further include a second container that includes an oncolytic virus or a pharmaceutical formulation thereof. In certain embodiments, the second container can include a single dose of the oncolytic virus or multiple doses of the oncolytic virus. In certain embodiments, the kit can further include a third container that includes an immunomodulatory agent or a pharmaceutical formulation thereof. In certain embodiments, the third container can include a single dose of the immunomodulatory agent or multiple doses of the immunomodulatory agent. A container can be any receptacle and closure suitable for storing, shipping, dispensing and/or handling a pharmaceutical product.

In certain embodiments, the kit can further include an additional container that includes a solvent, carrier and/or solution for diluting and/or resuspending the KRAS inhibitor, the oncolytic virus, the immunomodulatory agent, or a combination thereof. For example, but not by way of limitation, the additional container can include sterile water or saline.

In certain embodiments, the kits include one or more sterile containers which contain the KRAS inhibitor, the oncolytic virus, the immunomodulatory agent, pharmaceutical formulations thereof, or combinations thereof; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kit can further include instructions for administering the KRAS inhibitor, the oncolytic virus, the immunomodulatory agent, pharmaceutical formulations thereof, or combinations thereof. The instructions can include information about the use of the KRAS inhibitor, the oncolytic virus, the immunomodulatory agent, pharmaceutical formulations thereof, or combinations thereof for treating cancer. In certain embodiments, the instructions include at least one of the following: description of the KRAS inhibitor; description of the oncolytic virus; description of the immunomodulatory agent; dosage schedule and administration for treating cancer; precautions; warnings; indications; counter-indications; overdosage information; adverse reactions; animal pharmacology; clinical studies; and/or references. The instructions can be printed directly on the container (when present), or as a label applied to the container, or as a separate sheet, pamphlet, card, or folder supplied in or with the container. For example, but not by way of limitation, the instructions can describe the method for administration and the dosage amount. In certain embodiments, the instructions indicate that the KRAS inhibitor or pharmaceutical formulation thereof can be administered orally. In certain embodiments, the instructions can indicate that the KRAS inhibitor or a pharmaceutical formulation thereof can be administered to a subject at a dose of between about 0.05 mg/kg to about 100 mg/kg. In certain embodiments, the instructions can indicate that the oncolytic virus or pharmaceutical formulation thereof can be administered to a subject at a dose of between about 105 and 1010 plaque-forming units (PFU).

In certain embodiments, the kit can further include a device for administering the KRAS inhibitor, the oncolytic virus, the immunomodulatory agent, pharmaceutical formulations thereof, or combinations thereof. For example, but not by way of limitation, the device can include a syringe, catheter, e.g., implantable catheter, and/or pump.

EXAMPLES

The presently disclosed subject matter will be better understood by reference to the following Examples, which are provided as exemplary of the presently disclosed subject matter, and not by way of limitation.

Example 1

The present example illustrates the rational combination of a specific molecule-targeted inhibitor and an oncolytic (OV)-mediated antitumor immunity for KRASG12C cancers. The present example shows that this combination worked well in two murine KRASG12C tumor models, and the addition of an anti-PD-1 antibody further improved its efficacy. This combinatorial approach targeting various aspects of cancer for synergistic cytotoxicity and potent antitumor immunity can lead to optimal efficacy for KRASG12C mutant cancer with the potential long-term cure in human patients.

KRAS has been one of the most challenging targets in cancer. Cancers driven by KRAS mutations are both common and deadly. KRASG12C is an oncogenic driver mutation in multiple cancer types, including lung, colorectal, and pancreatic cancers. About 45% of all non-small-cell lung carcinoma (NSCLC) KRAS mutations in the US are KRASG12C [Arbour et al., Clin Cancer Res. 2018; 24: 334-340], which represents 25,000 NSCLC patients each year [Biernacka et al., Cancer Genet. 2016; 209: 195-198]. Researchers struggled to inhibit its mutated forms of KRAS—which earned a reputation as "undruggable." Few small molecule inhibitors specific to KRASG12C are available for preclinical and early-stage clinical studies. For example, the covalent compound ARS-1620 selectively achieved rapid and sustained in vivo occupancy to induce tumor regression in KRASG12C PDX models [Janes et al., Cell. 2018; 172: 578-589 e517]. Two-phase I clinical trials of the KRASG12C inhibitors MRTX849 and AMG510 have shown robust efficacy in human patients, including those with NSCLC [Canon et al., Nature. 2019; 575: 217-223; Hallin et al., Cancer Discov. 2020; 10: 54-71]. Two key features have been noticed in the application of KRASG12C inhibitors. First, KRASG12C inhibitors have resulted in the downregulation of IL-36γ in the tumor. Second, it was noted that AMG510, and possibly other inhibitors s as well, can induce inflammation and thus promote infiltration of immune cells into the tumor tissues, leading to enhanced efficacy of immune checkpoint blockade-mediated cancer immunotherapy when combined with anti-PD-1 antibody. Intriguingly, the latest generation of KRAS inhibitors, MRTX849 and MRTX1257, include potent, highly selective, orally deliverable small molecule KRASG12C inhibitors (Fell et al., J Med Chem. 2020; 63: 6679-6693).

Cancer immunotherapy is rapidly evolving, and treating cancer by activating the patient's immune system presents an attractive therapeutic strategy. Oncolytic virus (OV)-mediated cancer immunotherapy is one promising regimen, yet its efficacy as a single agent has been limited (Bommareddy et al., Nat Rev Immunol. 2018; 18: 498-513; Harrington et al., Nat Rev Drug Discov. 2019; 18: 689-706). OV selectively infects and replicates in cancer cells and/or cancer-associated stromal cells in vivo while leaving normal cells unharmed. OVs induce oncolysis of cancer cells, a mode of death called immunogenic cell death that subsequently induces antitumor immunity (Bartlett et al., Mol Cancer. 2013; 12: 103; Guo et al., Front Oncol. 2014; 4: 74). OVs have been shown in both pre-clinical studies and clinical trials to induce adaptive antitumor immunity contributing to the overall efficacy.

Materials and Methods:

Mice and cell lines. Female C57BL/6J (B6) mice, age 5-6 weeks old, were obtained from The Jackson Laboratory (Bar Harbor, ME) and housed in specific pathogen-free conditions. Murine colon cancer cell lines MC38, melanoma B16, Lewis lung cancer (LLC), were originally obtained from American Type Culture Collection (Manassas, VA). Mouse malignant mesothelioma AE17 cancer cell line was purchased from Millipore Sigma (Burlington, MA). Mouse colon cancer cell line MC38-luc was described previously. All cell lines were tested for mycoplasma once every three months or so, to ensure they were free of mycoplasma contamination.

Oncolytic vaccinia viruses. WR strain-derived oncolytic vaccinia virus (VVs) were used. vvTD (previous name vSPT) is an OV with mutations of triple viral genes encoding thymidine kinase (tk), antiapoptotic genes SPI-1 and SPI-2. vvTD-IL36γ is derived from vvTD with insertion of murine IL-36γ cDNA at the tk locus [Wang et al., Cancer Cell. 2015; 28: 296-306]. These oncolytic VVs were amplified in HeLa cells, and then purified and tittered as previously described.

Cell Viability Assay. The viability of cancer cells infected by OV or treated with MRTX1257 in vitro was measured using Cell Counting Kit-8 kit.

Tumor models and therapeutic treatments. For subcutaneous (s. c.) tumor models, B6 mice were subcutaneously inoculated with $5.0\times10^5$ LLC, or MC38 colon cancer cells. For subcutaneous AE17 tumor, 1.0e7 cancer cells were mixed with Matrigel for increased initiation and growth of the tumor. When the tumors reached the size of about 100-125 $mm^3$, vvTD, vvTD-IL36, or PBS was intratumorally injected at a dose of 2.0e6 pfu/tumor. The primary tumor size was measured using an electric caliper in two perpendicular diameters followed by measurement once every three days. For the long-term survival of mice, the health and survival of treated mice were closely monitored. All mice bearing subcutaneous were monitored via caliper measurements for changes in tumor size. Mice were dead naturally due to the disease or sacrificed when their subcutaneous tumor size exceeded 20 mm in diameter. Therapeutic and survival data by tumor model are summarized in Tables 3A-3D.

TABLE 3A

Figure 2B:
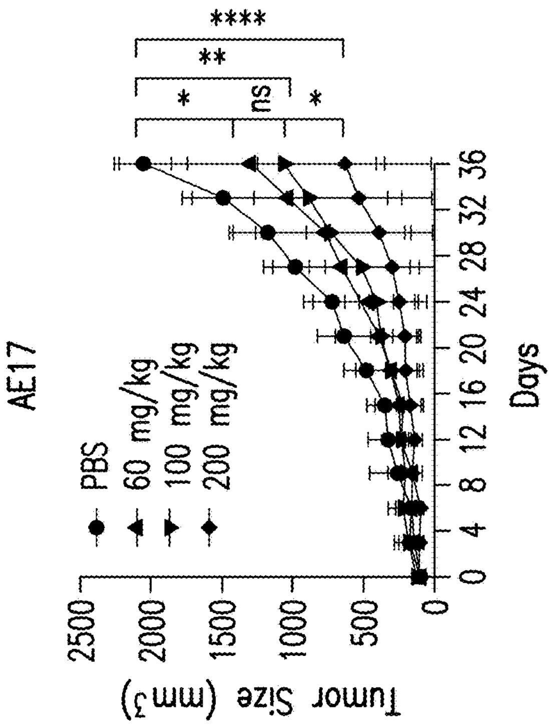
FIGS. 2A-2F illustrate anti-tumor efficacy of MRTX1257 in three subcutaneous tumor models.
Figure 2A:
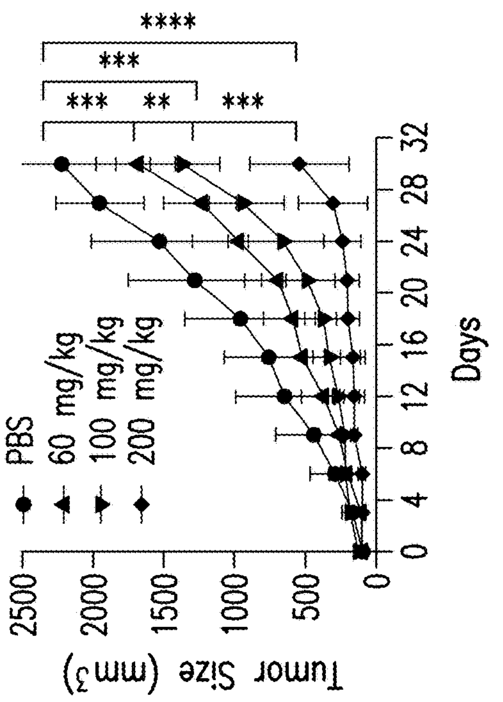
Figure 2C:
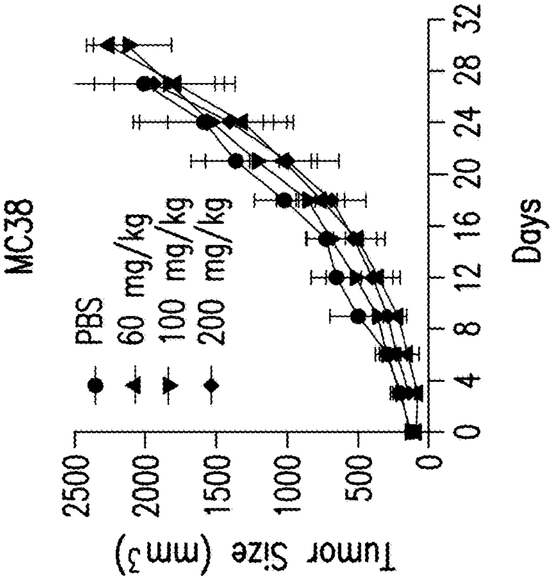
Figure 2D:
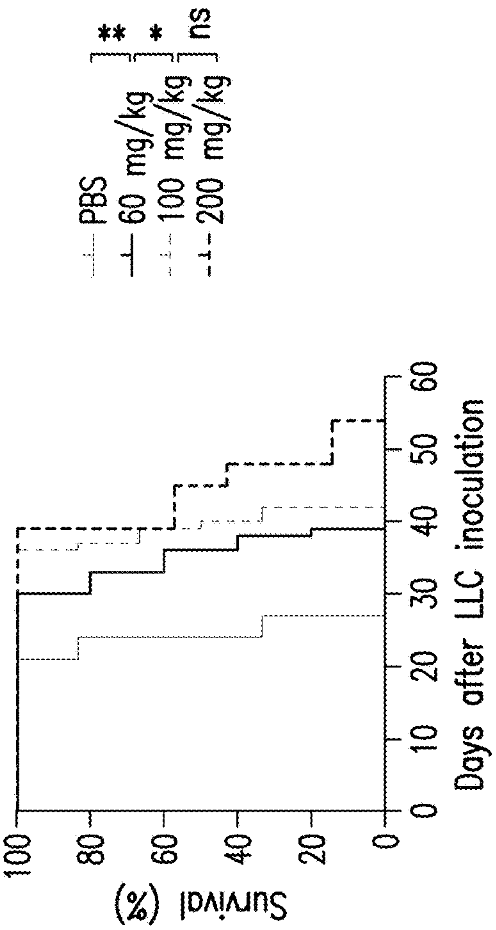
Figure 2E:
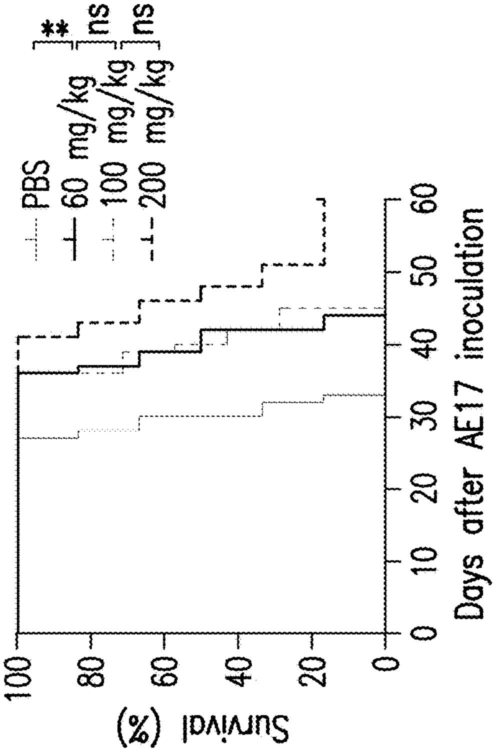
Figure 2F:
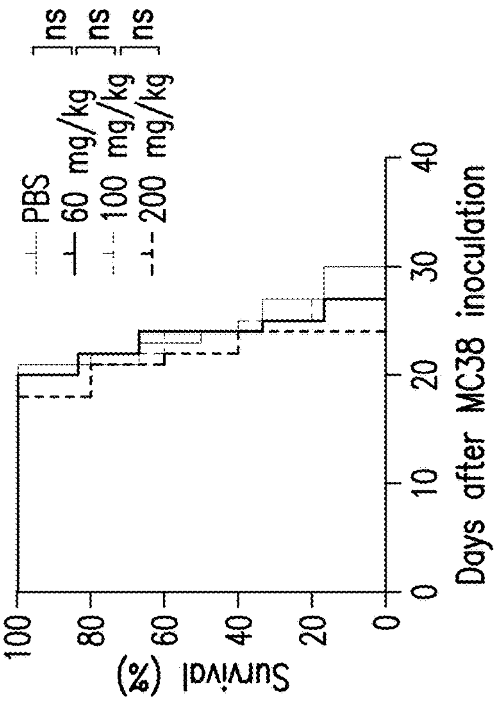

| Experiment | Treatment Group | n | Median survival (days) | p vs PBS | p vs 60 | p vs 100 | p vs 200 |
|---|---|---|---|---|---|---|---|
| MRTX1257 treated LLC s.c. tumor survival (FIG. 2D) | PBS | 6 | 24 | — | | | |
| | 60 mg/kg | 7 | 36 | ** | — | | |
| | 100 mg/kg | 7 | 39.5 | ** | * | — | |
| | 200 mg/kg | 7 | 45 | *** | ** | ns | — |
| AE17 s.c. tumor survival (FIG. 2E) | PBS | 6 | 30 | — | | | |
| | 60 mg/kg | 7 | 40.5 | ** | — | | |
| | 100 mg/kg | 7 | 40 | ** | ns | — | |
| | 200 mg/kg | 7 | 47 | *** | *** | *** | — |
| MC38 s.c. tumor survival FIG. 2F) | PBS | 6 | 23.5 | — | | | |
| | 60 mg/kg | 7 | 24 | ns | — | | |
| | 100 mg/kg | 7 | 24 | ns | ns | — | |
| | 200 mg/kg | 7 | 22 | ns | ns | ns | — |

TABLE 3B

Figure 3A:
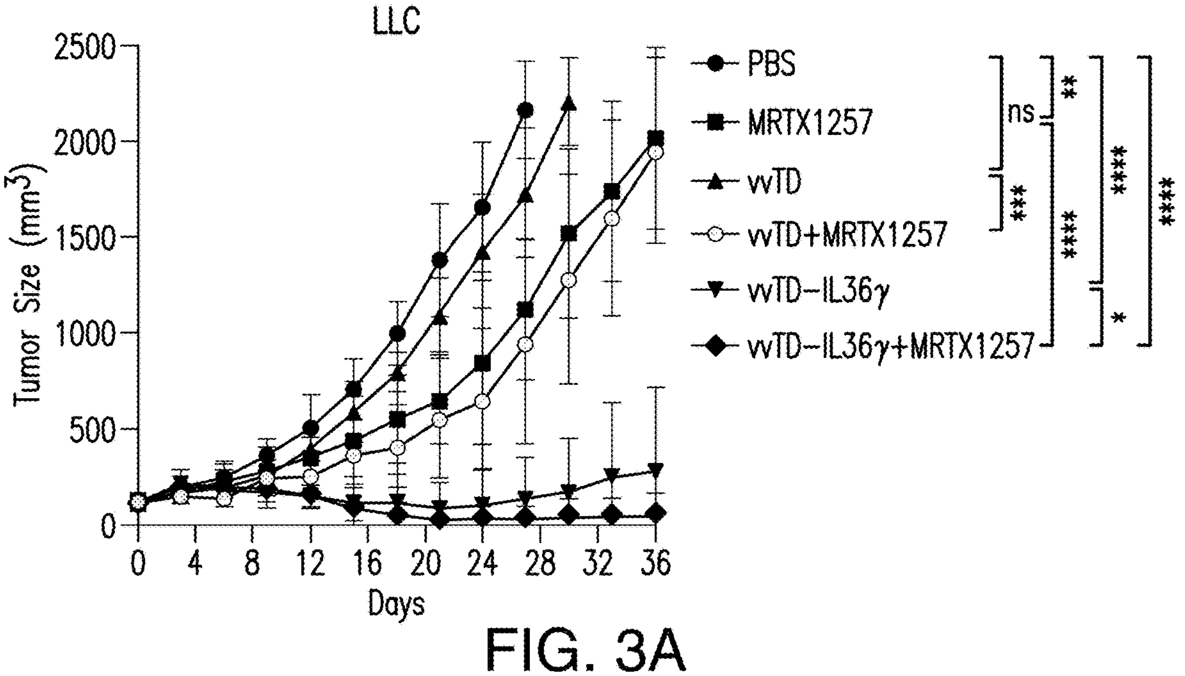
FIGS. 3A-3D illustrate anti-tumoral effects of an OV or in combination with MRTX1257 in murine KRASG12C tumor models. B6 mice were inoculated subcutaneously with 1.0e6 LLC or 1.0e7 AE17 cancer cells on the right flank. When tumor reached average 100-150 $mm^3$ (mostly on day 10), the mice were randomly divided into six groups (PBS; vvTD; MRTX1257; vvTD+MRTX1257; vvTD-IL36γ; vvTD-IL36γ+MRTX1257) (n=7~8). On day 11, mice were injected i.t. with 1.0e6 PFU of vvTD, vvTD-IL36γ, or PBS, then on day 13 treated with the MRTX1257 (60 mg/kg, daily for 3 weeks).
Figure 3B:
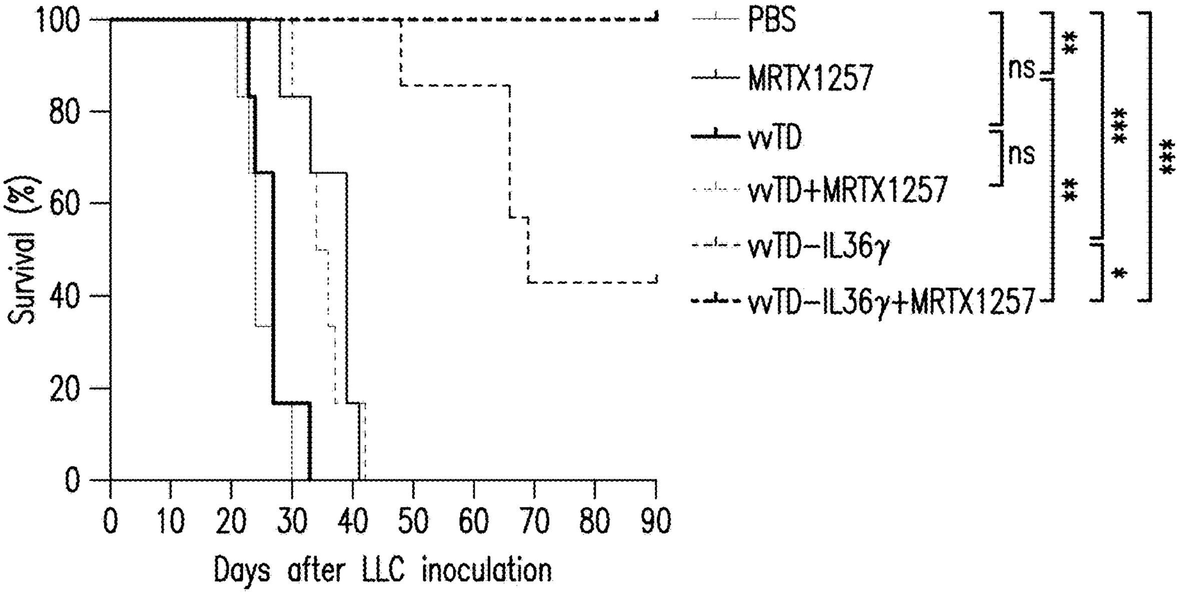

| Experiment | Treatment Group | n | Median survival (days) | PBS | MRTX 1257 | vvTD | vvTD + MRTX 1257 | vvTD-IL36γ | vvTD-IL36γ + MRTX 1257 |
|---|---|---|---|---|---|---|---|---|---|
| LLC Tumor Progression/ Survival FIG. 3B) | PBS | 6 | 24 | — | | | | | |
| | MRTX 1257 | 7 | 39 | ** | — | | | | |
| | vvTD | 7 | 27 | ns | ** § | — | | | |
| | vvTD + MRTX 1257 | 7 | 35 | ** § | ns § | *** | — | | |
| | vvTD-IL36γ | 7 | 69 | *** | *** § | *** § | *** § | — | |
| | vvTD-IL36γ + MRTX 1257 | 7 | >90 | *** | *** § | *** § | *** § | * | — |
| AE17 Tumor Progression/ Survival FIG. 3) | PBS | 6 | 31.5 | — | | | | | |
| | MRTX 1257 | 7 | 49.5 | ** | — | | | | |
| | vvTD | 7 | 31.5 | ns | ** § | — | | | |
| | vvTD + MRTX 1257 | 7 | 48 | ** § | ns § | ns | — | | |
| | vvTD-IL36γ | 7 | >90 | *** | *** § | *** § | *** § | — | |
| | vvTD-IL36γ + MRTX 1257 | 7 | >90 | *** | *** § | *** § | *** § | * | — |

TABLE 3C

| Experiment | Treatment Group | n | Median survival (days) | PBS | vvTD-IL36γ + M RTX1257 | +αCD8 | +αCD4 | +αPK136 |
|---|---|---|---|---|---|---|---|---|
| Selective Immune Depletion (FIG. 6C) | PBS | 8 | 24 | — | | | | |
| | vvTD-IL36γ + M RTX1257 | 8 | >150 | *** | — | | | |
| | +αCD8 | 8 | 25.5 | ns | *** | — | | |
| | +αCD4 | 8 | >150 | *** § | * | *** § | — | |
| | +αPK136 | 8 | >150 | *** § | * | *** § | ns § | — |

TABLE 3D

| Experiment | Treatment Group | n | Median survival (days) | PBS | MRT X1257 | αPD-1 | MRT X1257 + αPD-1 | vvTD-IL36γ + MRT X1257 | vvTD-IL36γ + αPD-1 | vvTD-IL36γ + MR TX12 57 + αPD-1 |
|---|---|---|---|---|---|---|---|---|---|---|
| Combination with PD-1 Blockade (FIG. 6E) | PBS | 6 | 24 | — | | | | | | |
| | MRT X1257 | 7 | 39 | *** | — | | | | | |
| | αPD-1 | 7 | 26 | ns | ** § | — | | | | |
| | MRT X1257 + αPD-1 | 5 | 42 | *** § | ns § | ** § | — | | | |
| | vvTD-IL36γ + MRT X1257 | 7 | 65 | *** | *** § | *** § | *** § | — | | |
| | vvTD-IL36γ + αPD-1 | 7 | >80 | *** | *** § | *** § | *** | ns§ | — | |
| | vvTD-IL36γ + MRT | 7 | >80 | *** | *** § | *** § | *** § | ns§ | ns | — |

TABLE 3D-continued

| Experiment | Treatment Group | n | Median survival (days) | PBS | MRT X1257 | αPD-1 | MRT X1257 + αPD-1 | vvTD-IL36γ + MRT X1257 | vvTD-IL36γ + αPD-1 | vvTD-IL36γ + MR TX12 57 + αPD-1 |
|---|---|---|---|---|---|---|---|---|---|---|
| | X1257 + αPD-1 | | | | | | | | | |

Flow cytometry. Tumor tissues were collected from mice, minced and incubated in RPMI 1640 medium containing 2% FBS, 1 mg/mL collagenase IV (Sigma: #C5138), 0.1 mg hyaluronidase (Sigma: #H6254), and 200U DNase I (Sigma: #D5025) at 37° C. for 1 h to make single cells. Single-cell samples were processed for flow cytometry as described (Feist M 2020). After staining with 100 μL Zombie Aqua Fixable Viability Kit cell dye (BioLegend, San Diego, CA), cells were stained in 100 μL total stain volume (50 μL, BV stain buffer, 50 μl 2% FBS) with antibody at a dilution of 1:200 for 30 min on ice in the dark.

RT-qPCR. On day 6 and day 11 post virus treatments, tumor tissues or spleens were harvested, and then single-cell suspension was made for cell separation and further analysis of immune cells either by flow cytometry or by RT-qPCR.

Enzyme-linked immunospot (ELISpot) assay. Collected tumor tissues were cut into pieces and incubated at 37° C. in digestion buffer (Miltenyi Biotec, San Diego, CA) before being mashed over a 100 μM tissue strainer. ELISpot assay was performed as described previously.

Statistics. Statistical analyses were performed using unpaired Student's t-test for two-group comparison. For multiple group comparisons, one-way ANOVA was used where p-value is adjusted for multiple tests by Dunnett method (GraphPad Prism version 5). Animal survival is presented using Kaplan-Meier survival curves and compared by using log-rank test (GraphPad Prism version 5). Value of $p<0.05$ is considered to be statistically significant, and all p values were two-sided. In the figures, the standard symbols were used: *p<0.05; p<0.01; *p<0.001; ****p<0.0001; and NS: not significant.

Figure 1B:
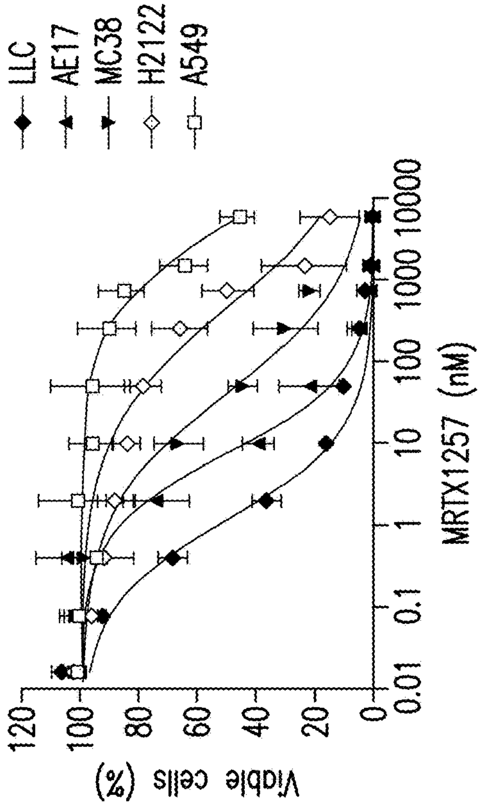
Figure 1C:
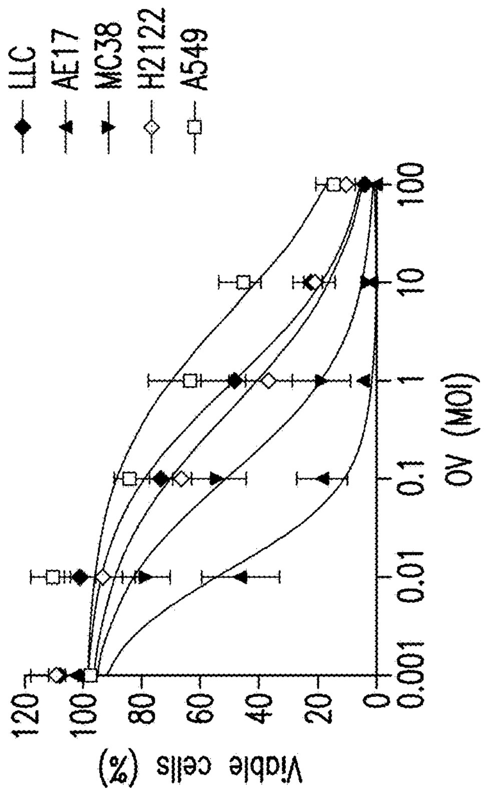
Figure 1E:
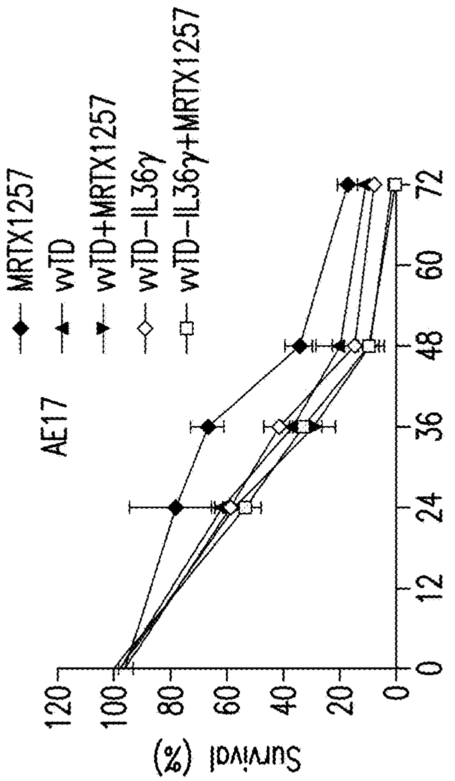
Figure 1D:
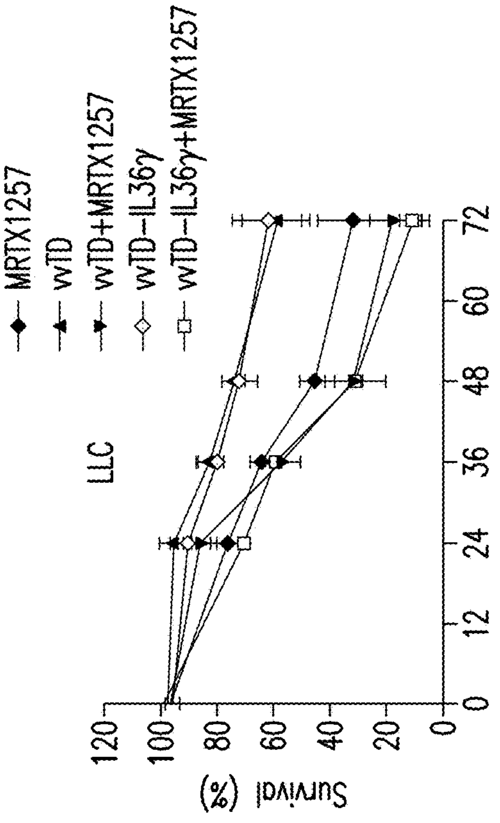
Figure 1F:
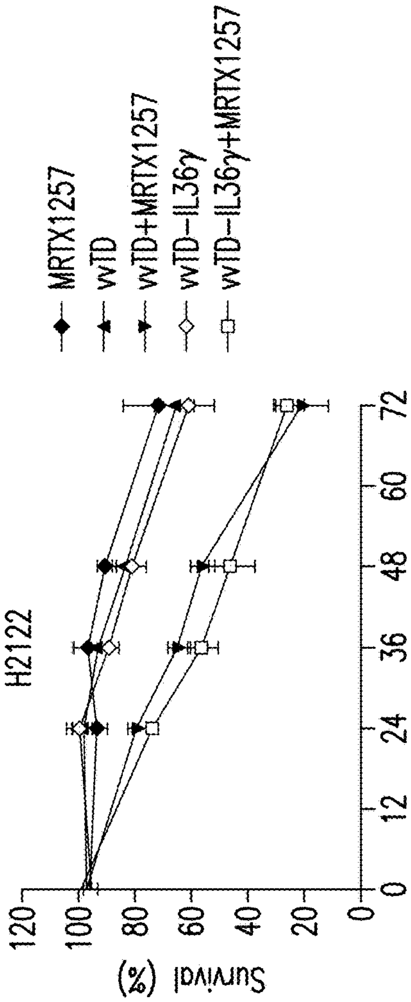
Figure 1H:
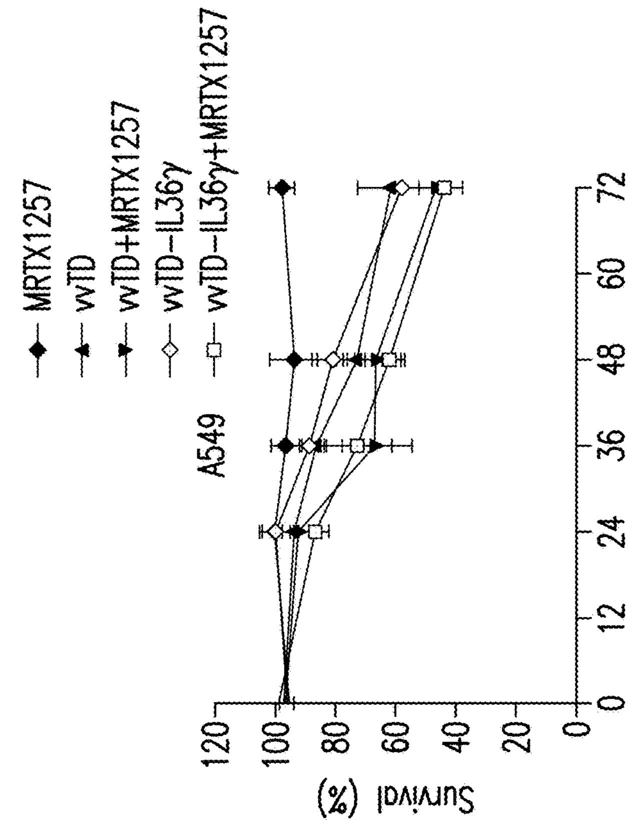
Figure 1G:
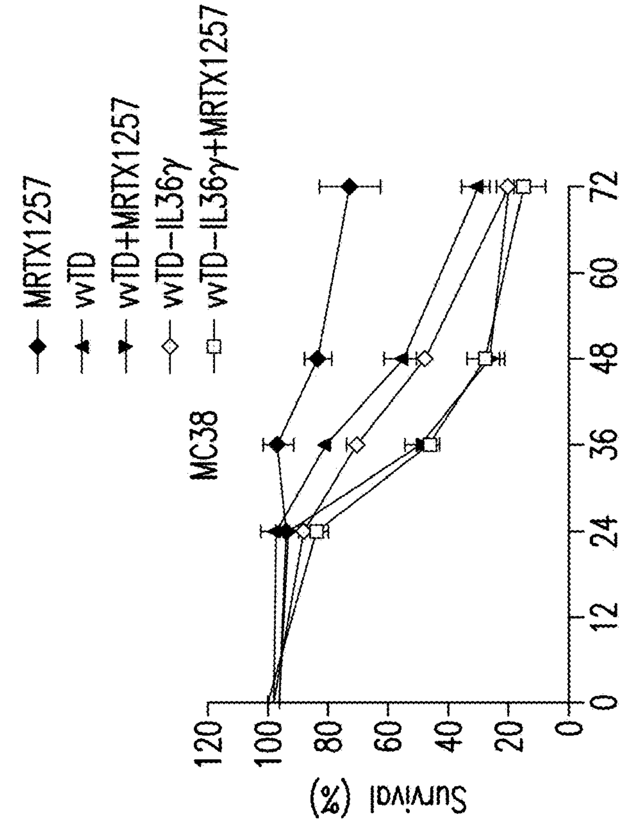
Figure 1I:
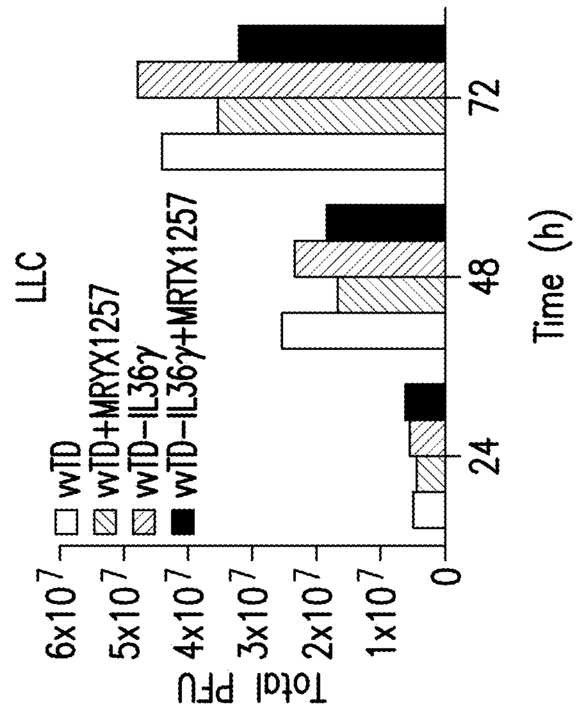

Results:

To confirm that the efficacy of MRTX1257, a covalent inhibitor specific to KRAS G12C oncoprotein, cytotoxicity studies were performed in a panel of human and murine cancer cell lines that harbor KRASG12C mutant protein or non-KRASG12C mutant protein (FIG. 1A). Among murine cancer cell lines, LLC (lung cancer) and AE17 (mesothelioma) are KRASG12C mutants, while MC38 (colon cancer) is not. Among human lung cancer cell lines, H2122 is KRASG12C mutant while A549 is not. The cancer cells were plated in 96-well plates overnight and then infected with various MOIs of vvTD-IL36γ (FIG. 1B). The sensitivity of these cancer cells varied a lot, with a difference of LD50 over 1,000-fold. The most sensitive one was MC38 while the least sensitive one was A549 (FIG. 1B). Then, the sensitivity of these cancer cells to MRTX1257 was tested. The cancer cells were treated with MRTX1257 drug at a dose range of 0.0, 0.016 up to 7500 nM (FIG. 1C). The viable cells were measured at 48 h post-treatment with CCK8 assay. LLC and AE17 cells were highly sensitive to MRTX1257 while MC38 was less sensitive. For human cancer cells, H2122 was more sensitive than A549 cells.

Figure 1J:
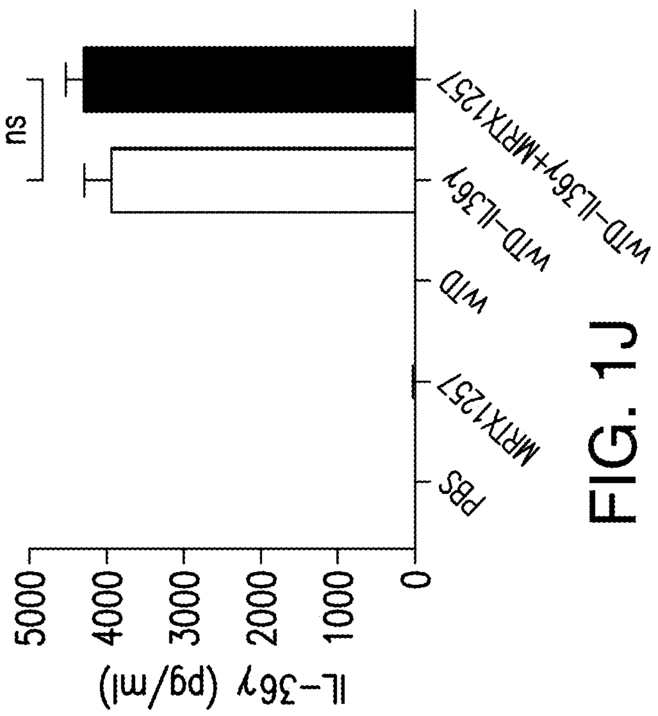

For straightforward comparison, the MOT of the OV was set at 0.5 and MRTX1257 at 100 nM and the five lines of cancer cells were compared for their susceptibility to these two types of antitumor agents (FIGS. 1D-1H). All three murine cancer cell lines were sensitive to both OVs, with similar kinetics of oncolysis over time. As for MRTX1257, MC38 (KRASG12C non-mutant) cells were much more resistant to this drug-mediated cytotoxicity than the other two cancer lines. The effects of MRTX1257 on the viral replication of vvTD and vvTD-IL36γ were tested (FIG. 11). MRTX1257 had a small inhibitory effect on the viral replication and accumulation. As a verification, cells infected with vvTD-IL36 alone or in combination with MRTX1257, led to the production and secretion of high levels of IL-36γ (FIG. 1J).

In both LLC and AE17 tumor models that are KRASG12C, MRTX1257 had good efficacy at inhibiting tumor growth and prolonged the survival of mice bearing the tumor in a dose-dependent manner (FIGS. 2A-2B). However, the drug had no effect on MC38 tumor model that is non-KRASG12C mutant (FIG. 2C). The antitumor effects were also reflected in the extension of survival of mice in a dose-dependent manner in LLC and AE17, but not in MC38 tumor model (FIGS. 2D-2F). Thus, the specificity of the small molecule inhibitor was confirmed in tumor models in vivo.

Figure 3C:
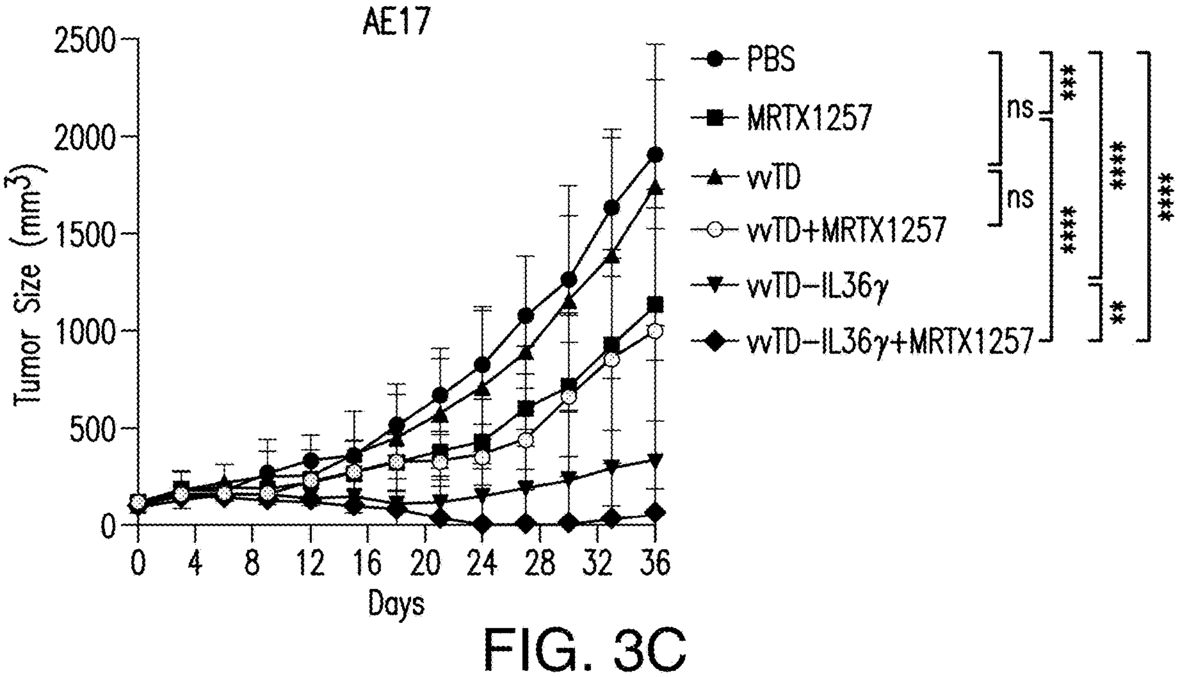
Figure 3D:
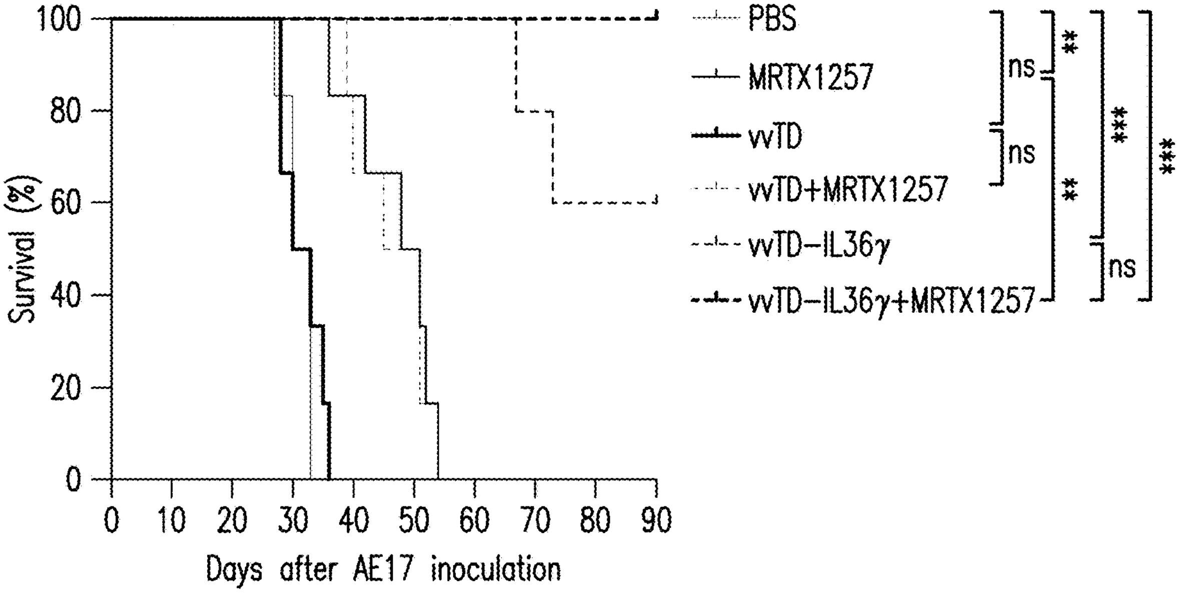

The potential of combining the inhibitor with a potent IL-36γ-armed OV in KRASG12C mutant tumor models was tested (FIGS. 3A-3D). The two agents were used at sub-optimal concentrations: MRTX1257 at 60 mg/kg body-weight (oral delivery), and OVs at 2.0e6 pfu/mouse (intratumoral delivery). In LLC model (FIG. 3A-3B), MRTX1257 showed a significant antitumor effect (FIG. 3A). vvTD, the parental OV, showed vert little therapeutic effect (ns, compared to PBS), yet IL-36γ-armed OV displayed very potent antitumor efficacy ($p<0.0001$, when compared to PBS). The combination of vvTD with MRTX1257 led to an improved result. Yet the combination of MRTX1257 and vvTD-IL36γ led to the best therapeutic efficacy ($p<0.05$ compared to vvTD-IL36γ; $p<0.0001$ compared to MRTX1257). Similar patterns of antitumor effects were also observed in AE17 tumor model, another KRASG12C mutant tumor (FIG. 3C). These antitumor effects were translated into longer survival of mice in both LLC model (FIG. 3B) and AE17 tumor model (FIG. 3D).

Figure 4A:
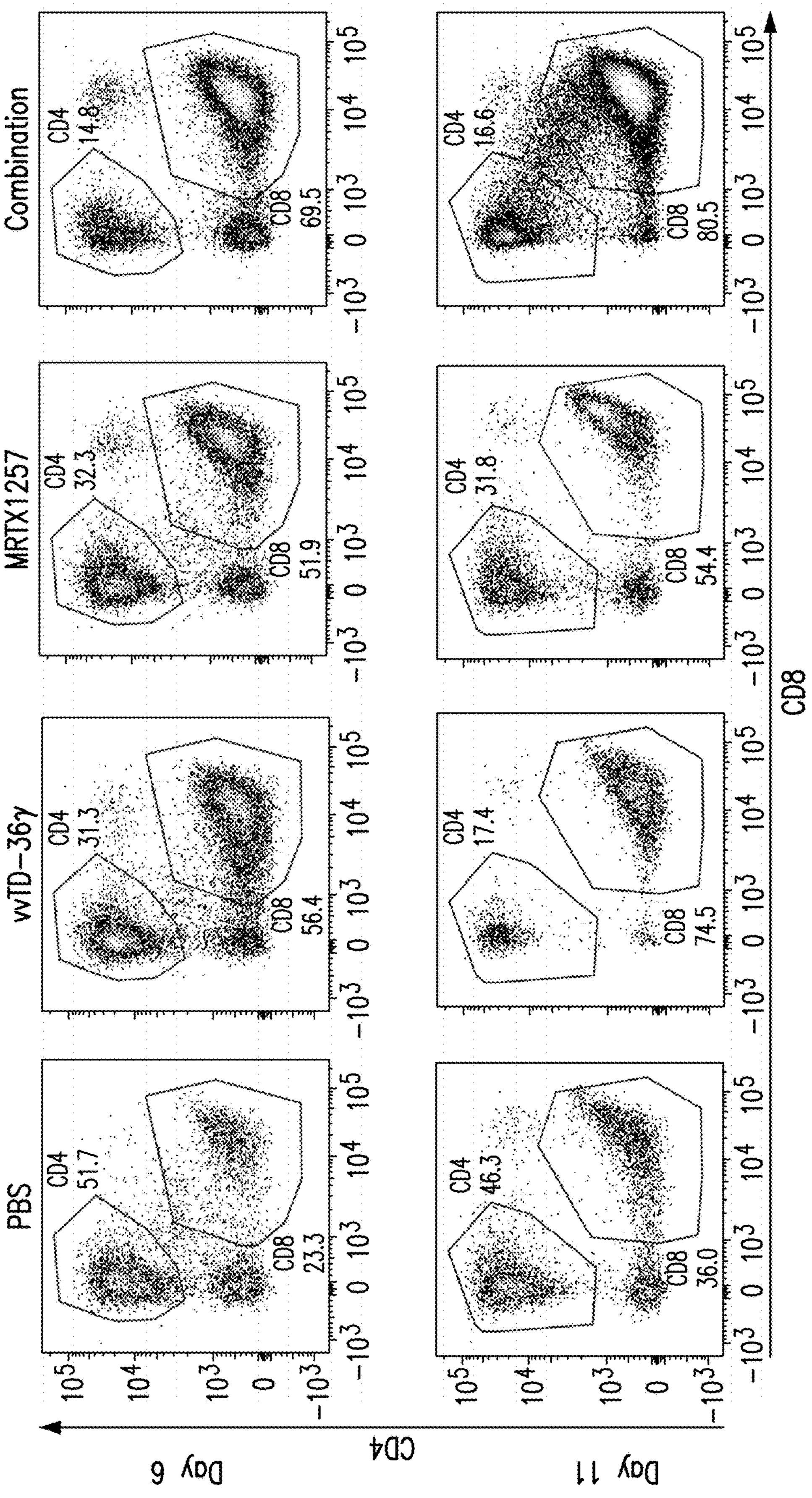
FIGS. 4A-4I illustrate changes of quantities of CD4+ and CD8+ T cell subsets and key functional molecules in the LLC tumor microenvironment after therapy with vvTD-IL36γ, MRTX1257 or the dual combination. B6 mice were inoculated s.c. with 1.0e6 LLC cells. On day 11, mice were randomly split into groups and treated with PBS, single dose of vvTD-IL36γ (2.0e6 PFU/mouse) that day, MRTX1257 (60 mg/kg; oral garage daily for 3 weeks), or combination (vvTD-IL36γ+MRTX1257). Tumor-bearing mice were sacrificed on days 6 and 11 post-treatment, and tumor tissues were collected, single cells prepared and analyzed by flow cytometry.
Figure 4B:
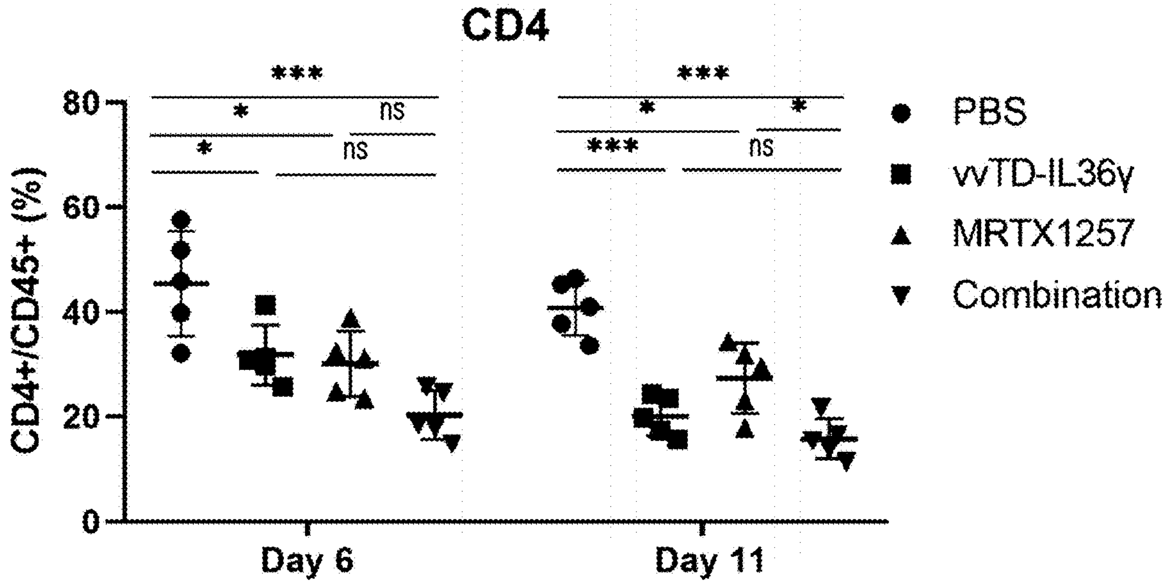
Figure 4C:
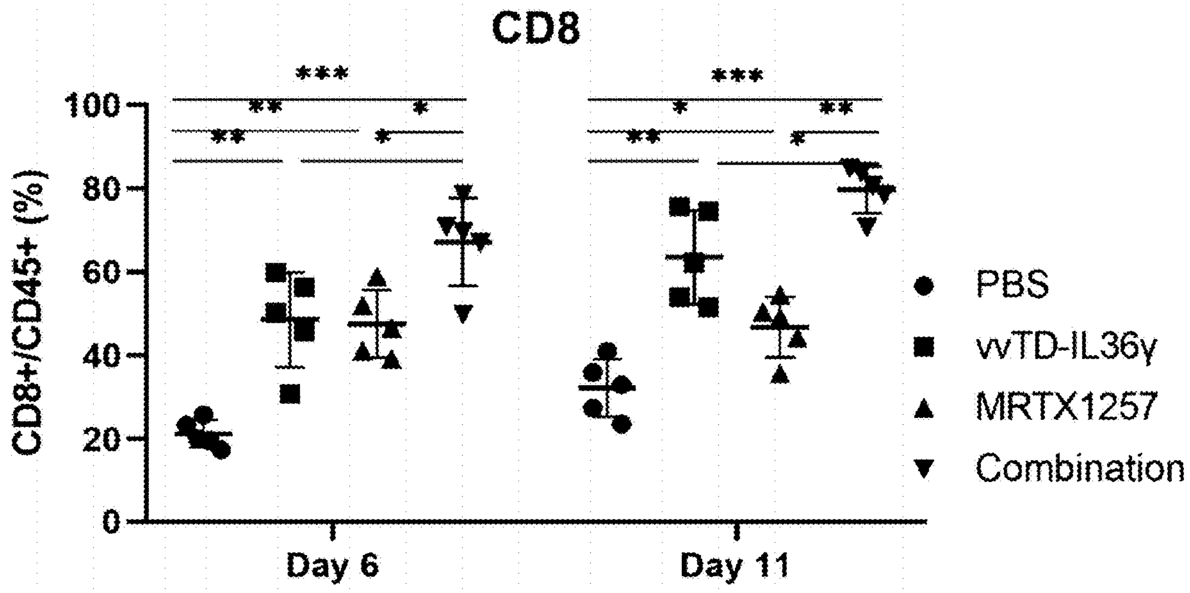

The dynamics of the immune profile in the tumor tissue were examined on days 6 and 11 after treatments. It was observed a reduction of CD4+ T cells in all treated groups as compared to PBS on days 6 and 11 (FIGS. 4A-4B). However, there was no reduction of CD8+ T cells in groups treated with either vvTD-IL36 or MRTX1257 ($p<0.01$) (FIGS. 4A, 4C). In dual therapy, there was a further increase as compared to either monotherapy ($p<0.05$ compared to monotherapies; and $p<0.001$ when compared to PBS). Next, the key molecular markers for the status of immunity in the TME were analyzed by RT-qPCR (FIGS. 4D-4I). An enhancement of CD4 marker in monotherapies and a further increase in dual therapy on day 6 was observed (FIG. 4D). This seemed to be contradictory to flow data (FIG. 4A. B).

Figure 4E:
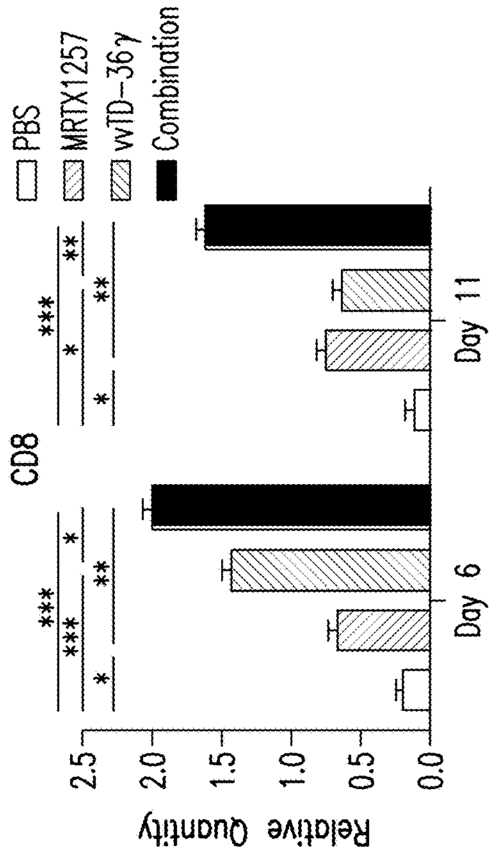
Figure 4D:
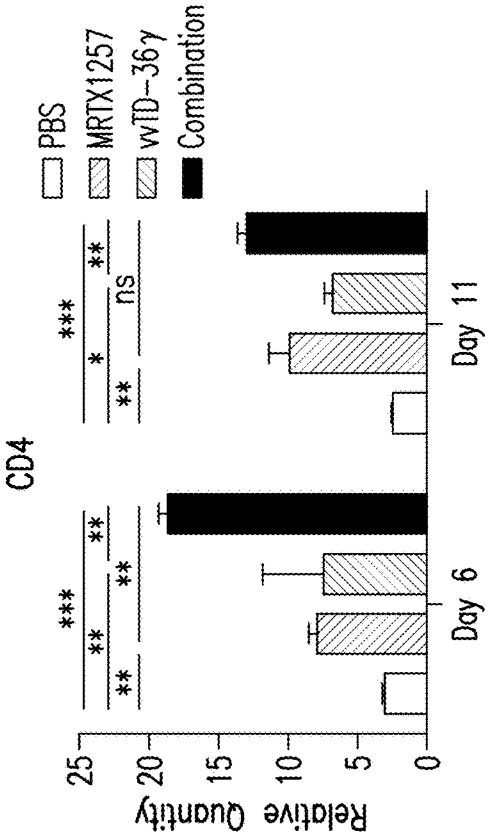
Figure 4F:
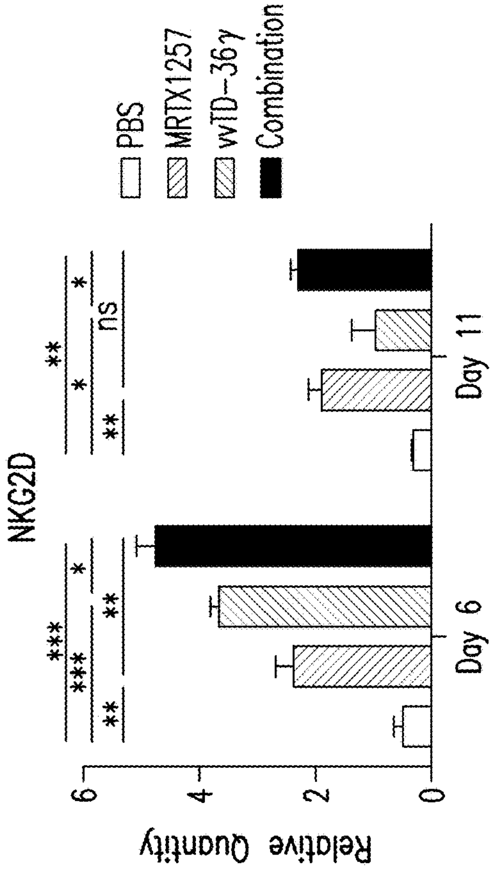
Figure 4G:
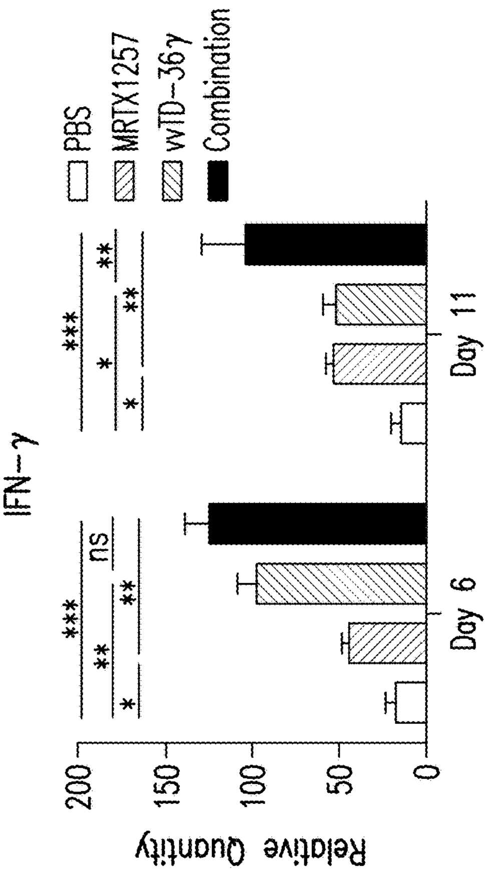
Figure 4H:
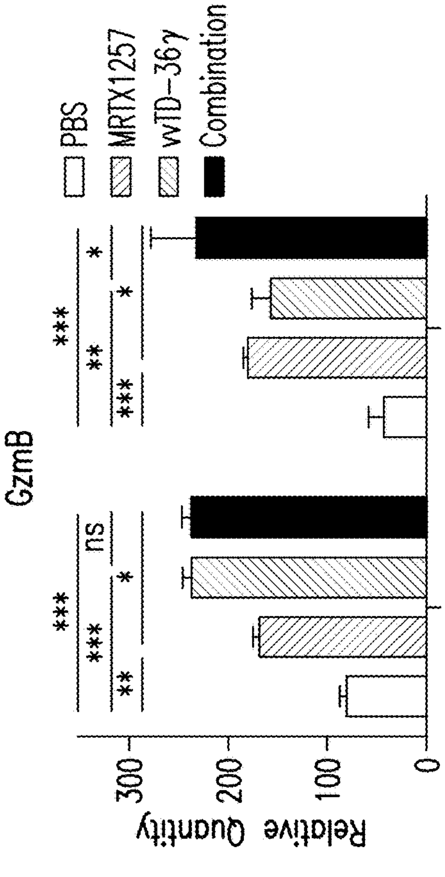
Figure 4I:
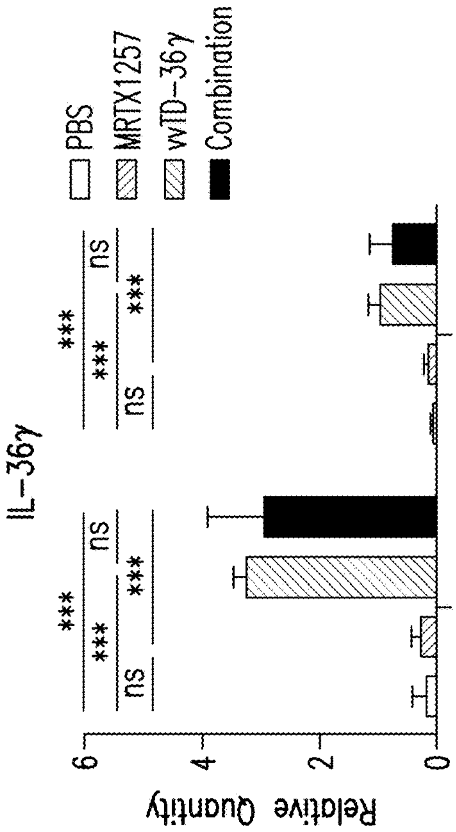

However, the patterns of CD8 were consistent with data from flow (FIG. 4E). NKG2D, IFN-γ, and GzmB were all enhanced by either monotherapy, and either maintained at high level or further increased in dual therapy (FIGS. 4F-4H). As for IL-36γ mRNA expression, there was high-level expression in vvTD-IL36γ or dual therapy on day 6 (p value: ns), and the levels were reduced by day 11 (FIG. 4I).

Figure 5B:
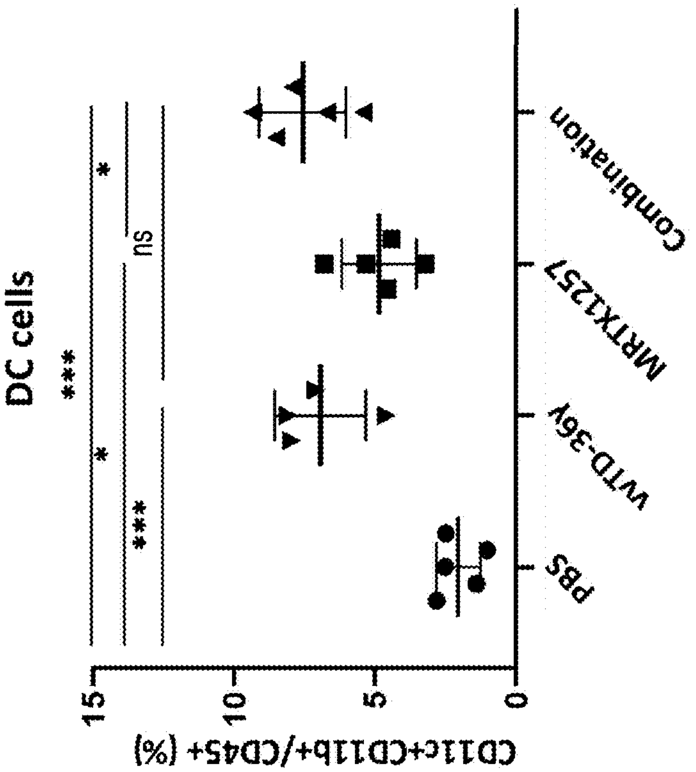
FIG. 5B shows levels of DC cells (CD11c+CD11b+).
Figure 5A:
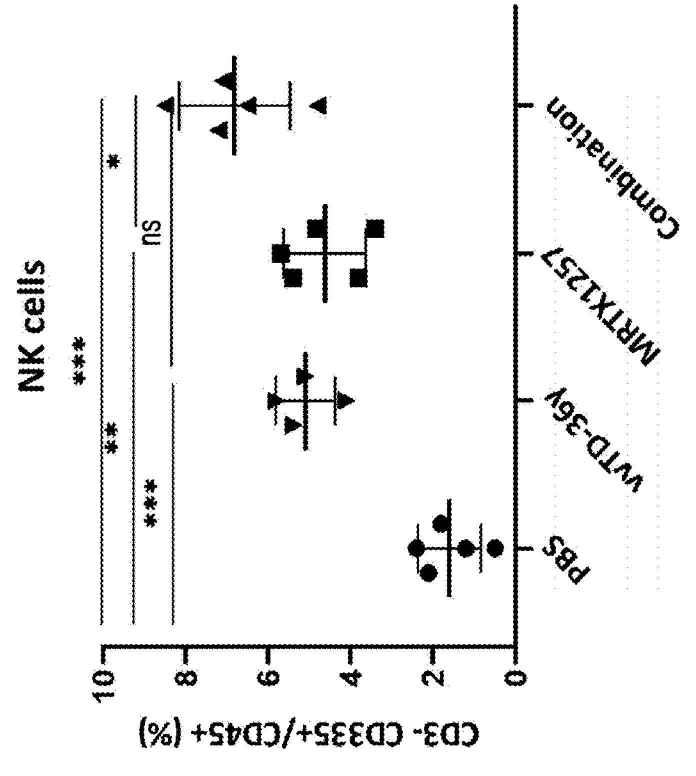
FIGS. 5A-5O illustrate changes of immune status in the tumor microenvironment after monotherapies or dual therapy with vvTD-IL36γ and MRTX1257. B6 mice were inoculated s.c. with 1.0e6 LLC cells and treated with PBS, vvTD-IL36γ as described (2.0e6 PFU per mouse 11 days post-tumor inoculation), MRTX1257 (60 mg/kg per mouse 13 days post-inoculation using a daily schedule by oral gavage for 3 weeks), or combination (vvTD-IL36γ+MRTX1257 scheduled as before). Tumor-bearing mice were sacrificed 6 days post-treatment and primary tumors were collected and analyzed by flow cytometry.
Figure 5D:
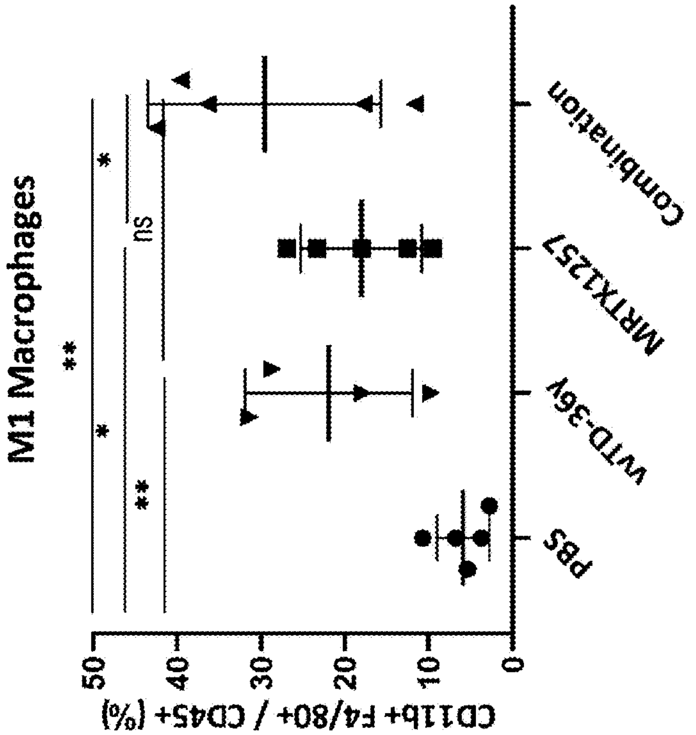
FIG. 5D shows levels of M1-like Macrophages (CD11c+F4/80+).
Figure 5C:
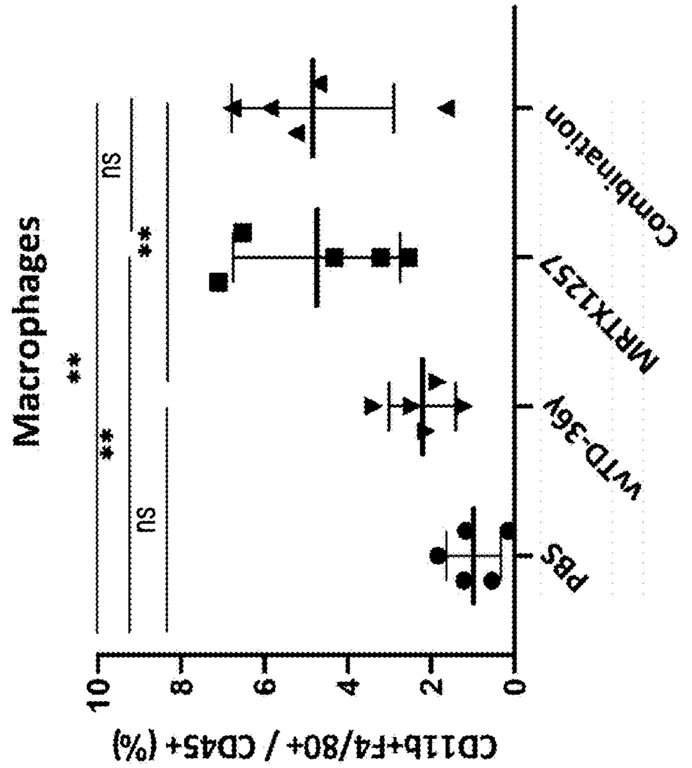
FIG. 5C shows levels of macrophages (F4/80+CD11b+).
Figure 5F:
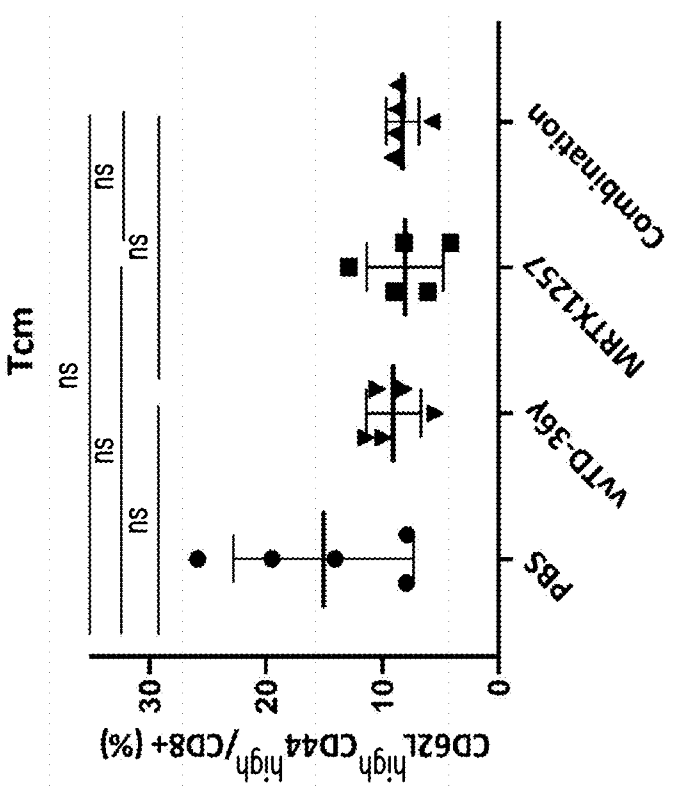
FIG. 5F shows levels of central Memory T cells (CD62L+CD44+).
Figure 5E:
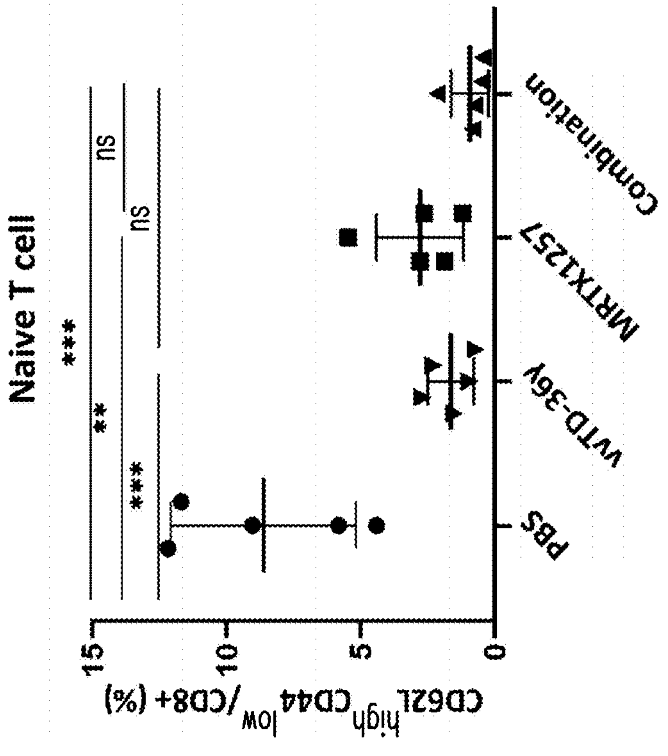
FIG. 5E shows levels of naive T cells (CD62L+ CD44−).
Figure 5H:
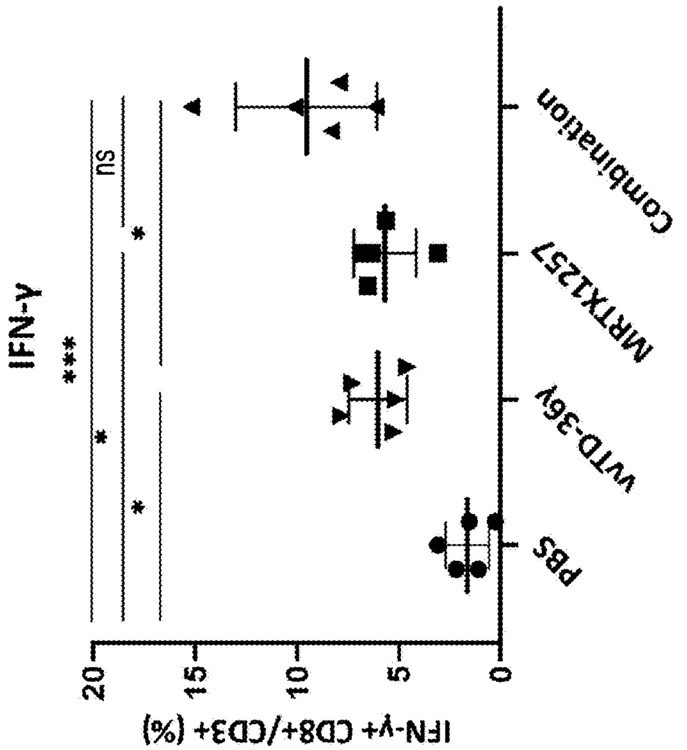
FIG. 5H shows levels of CD8+IFN-γ+ T cells.
Figure 5G:
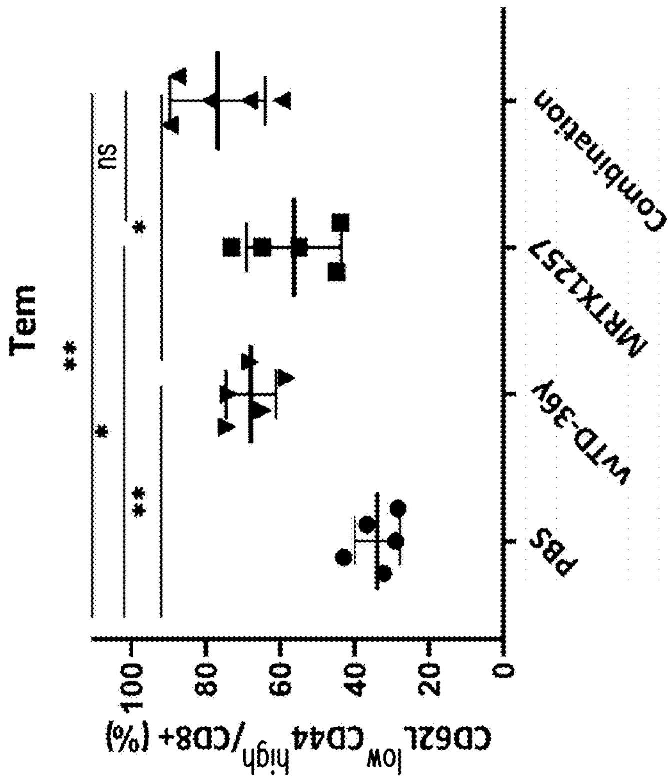
FIG. 5G shows levels of effector memory T cells (CD62L− CD44+).
Figure 5J:
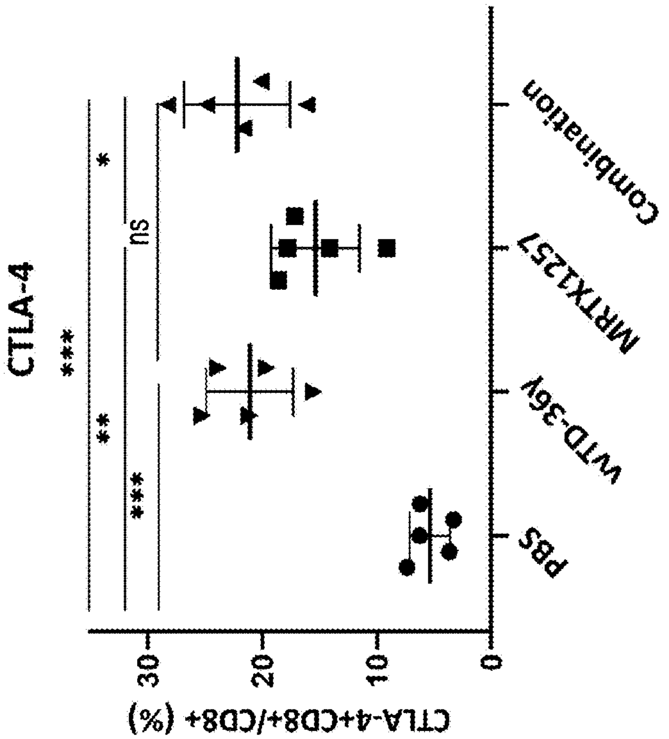
FIG. 5J shows levels of TIM-3+CD8+ T cells.
Figure 5I:
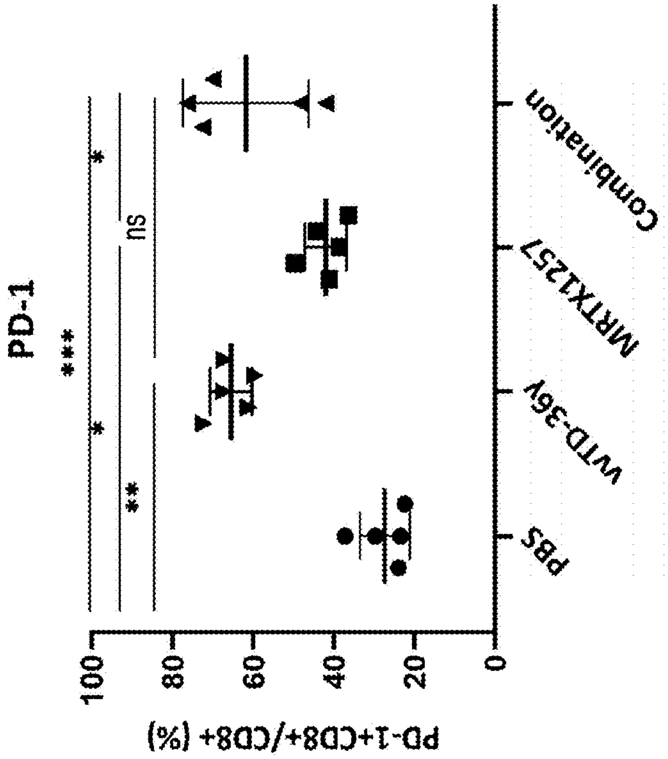
FIG. 5I shows levels of PD-1+CD8+ T cells.
Figure 5L:
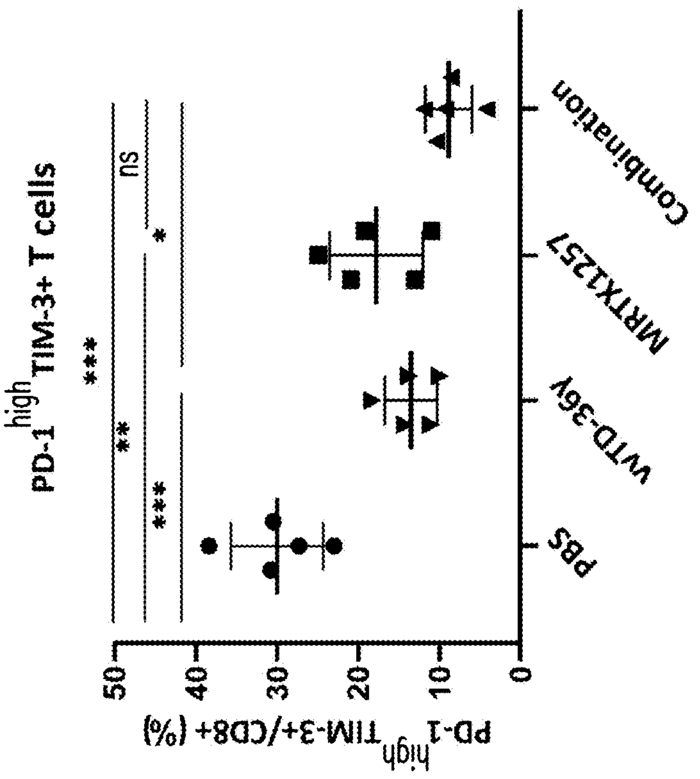
FIG. 5L shows levels of exhausted CD8+ T cells (PD1hiTIM3+CD8+).
Figure 5K:
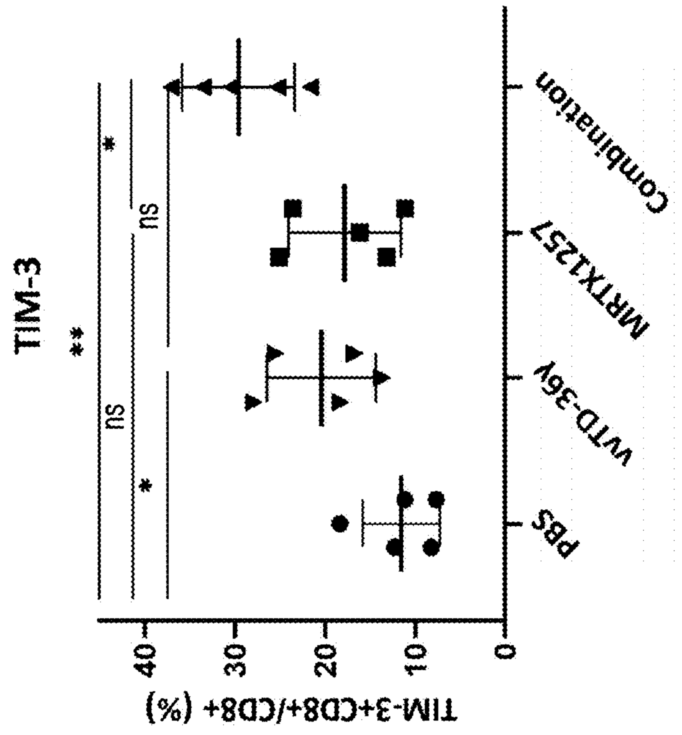
FIG. 5K shows levels of CTLA-4+ CD8+ T cells.
Figure 5N:
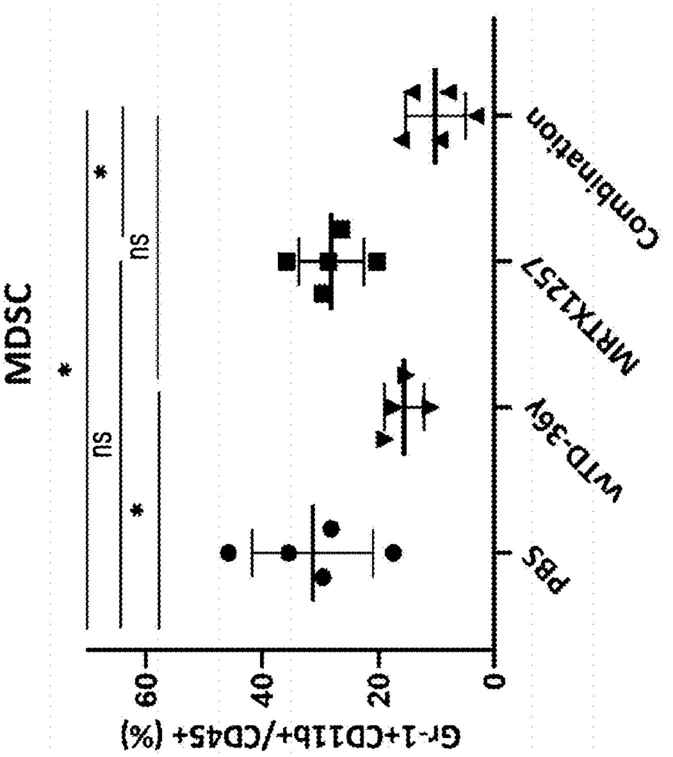
FIG. 5N shows levels of myeloid-derived suppressor cells.
Figure 5M:
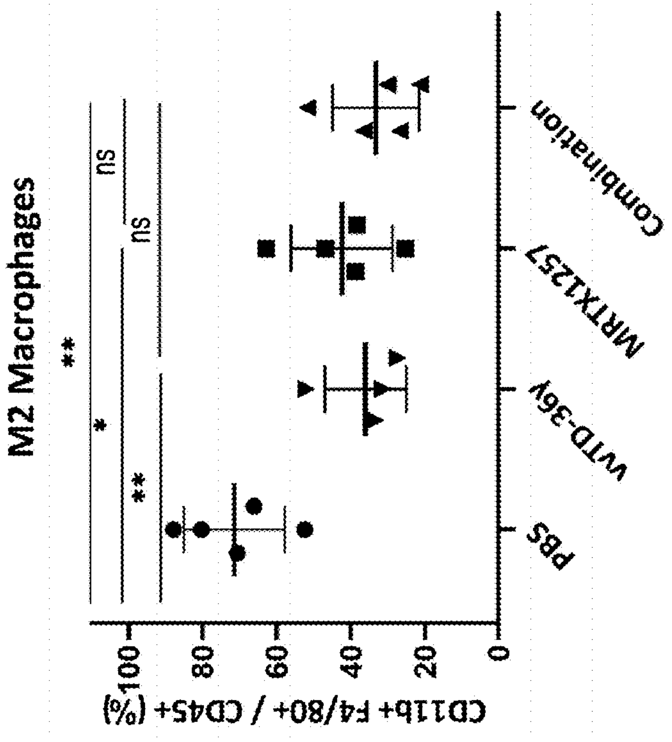
FIG. 5M shows levels of M2-like Macrophages (CD206+F4/80+).
Figure 5O:
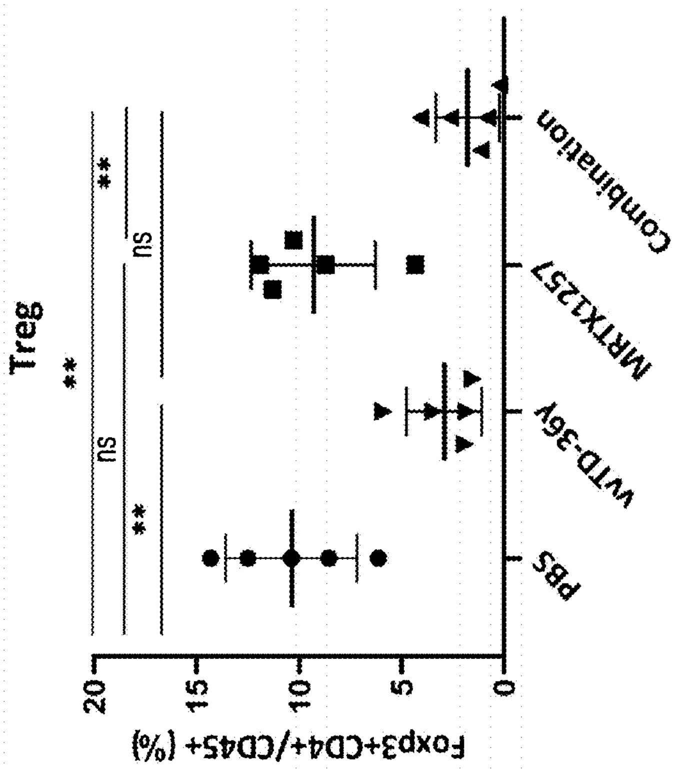
Figure 9B:
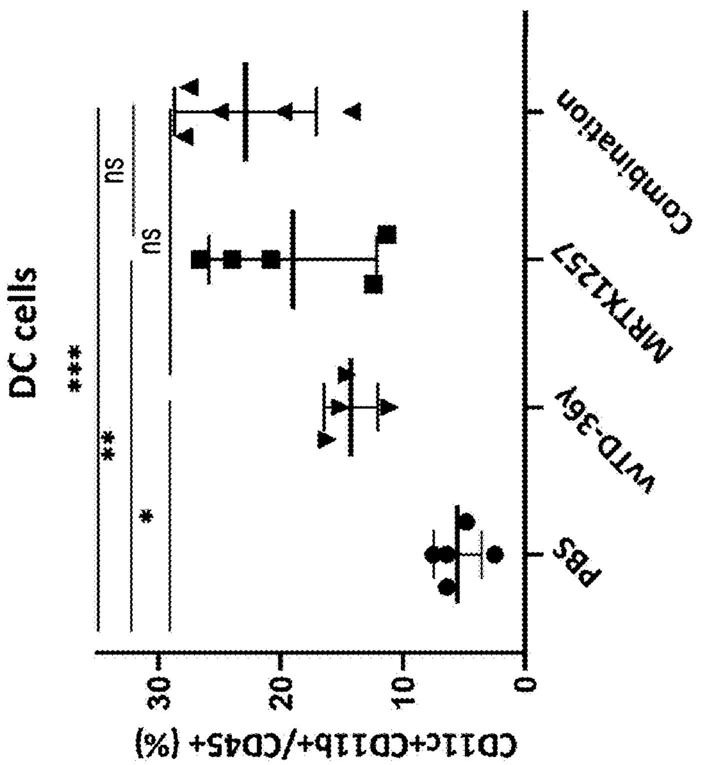
FIG. 9B shows levels of DC cells (CD11c+CD11b+).
Figure 9A:
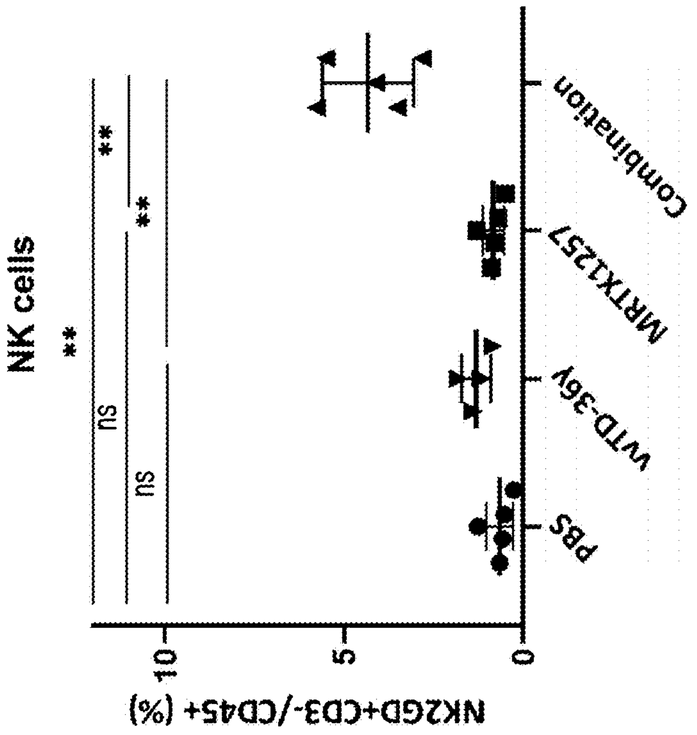
FIGS. 9A-9O illustrate the immune status change in the tumor microenvironment 11 days after vvTD-IL36γ alone or combined with MRTX1257 treatments.
Figure 9D:
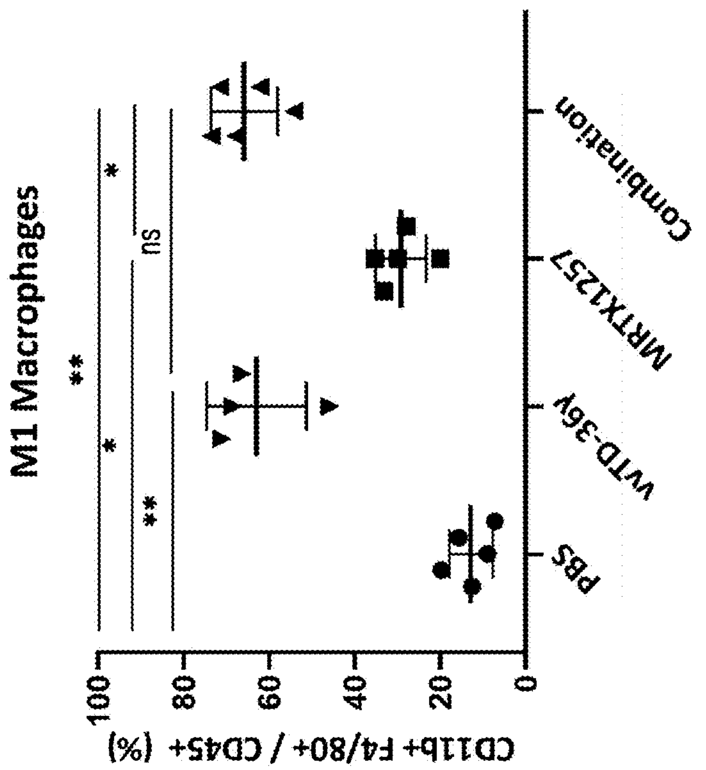
FIG. 9D shows levels of M1-like Macrophages (CD11c+F4/80+).
Figure 9C:
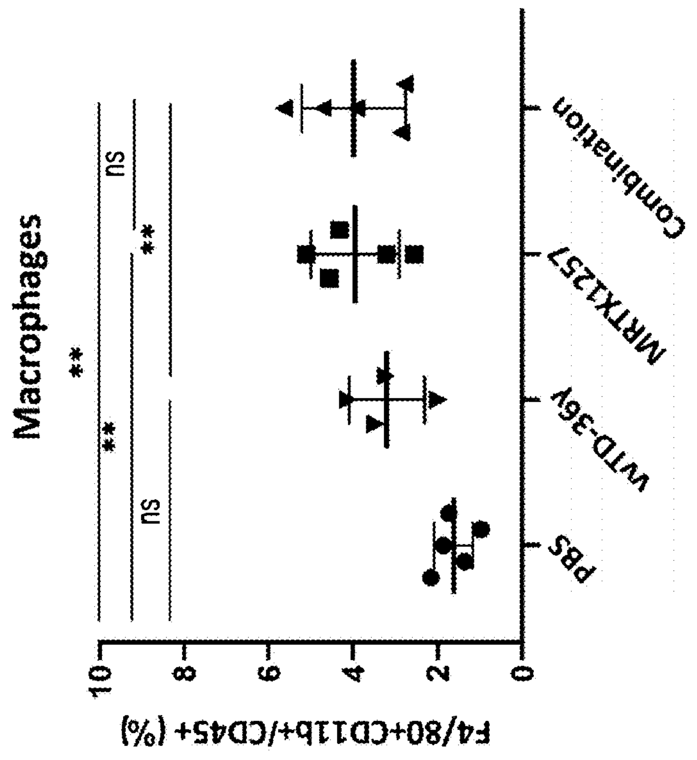
FIG. 9C shows levels of macrophages (F4/80+CD11b+).
Figure 9F:
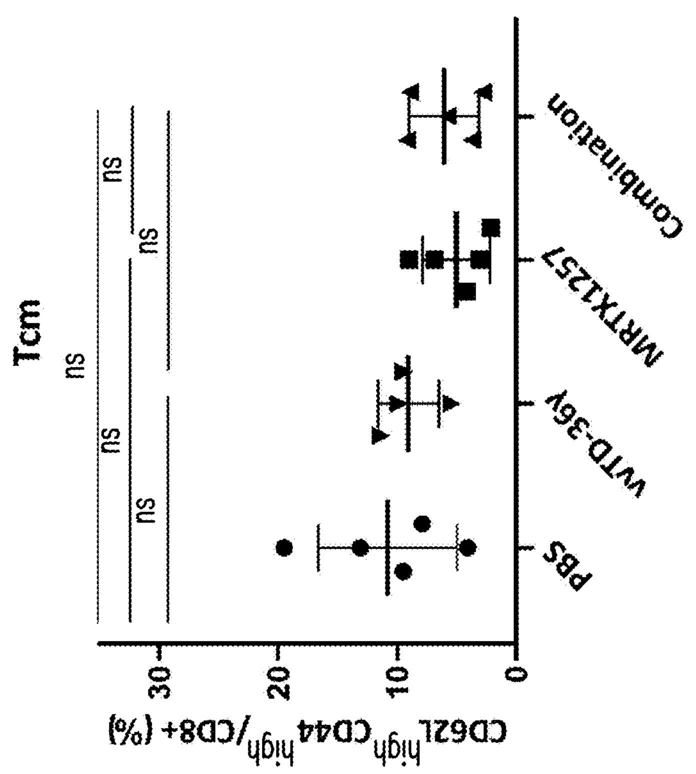
FIG. 9F shows levels of central Memory T cells (CD62L+ CD44+).
Figure 9E:
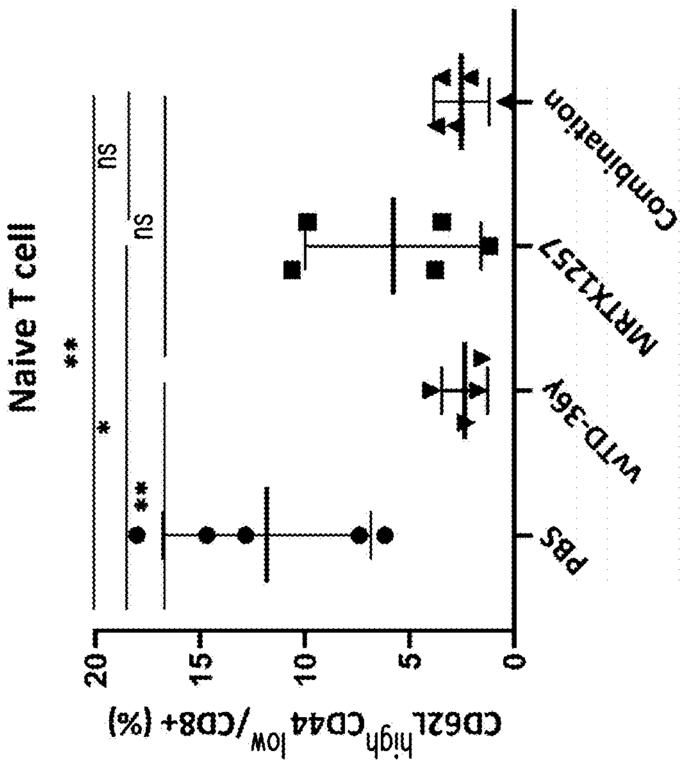
FIG. 9E shows levels of naive T cells (CD62L+CD44−).
Figure 9H:
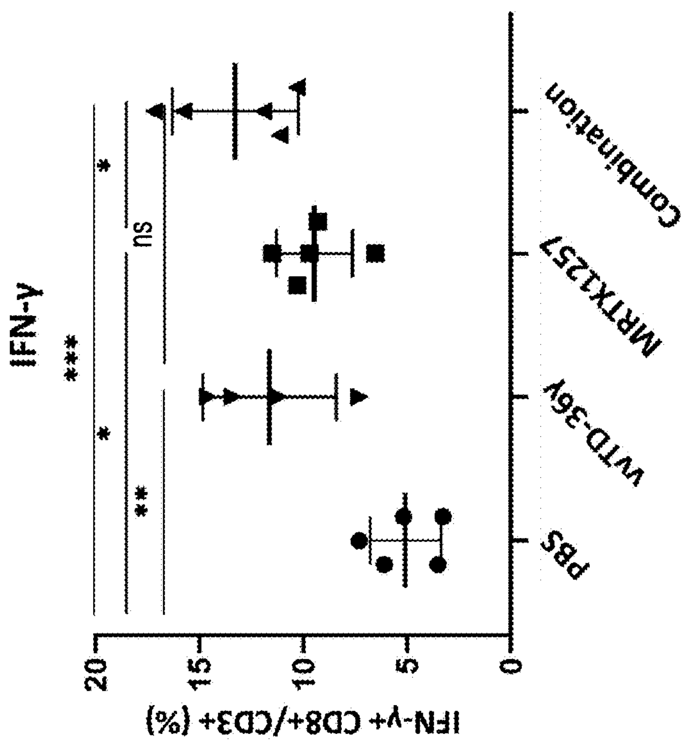
FIG. 9H shows levels of CD8+IFN-γ+ T cells.
Figure 9G:
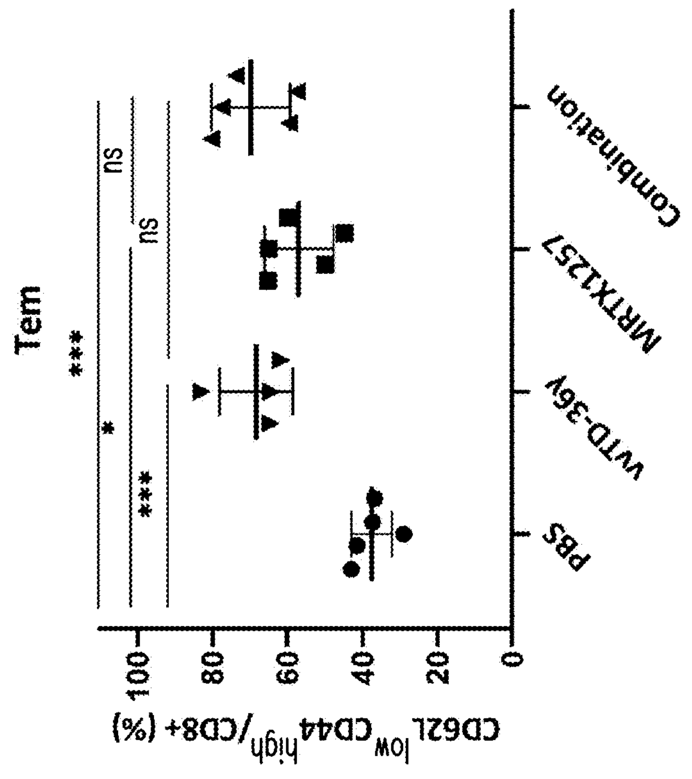
FIG. 9G shows levels of effector Memory T cells (CD62L− CD44+).
Figure 9J:
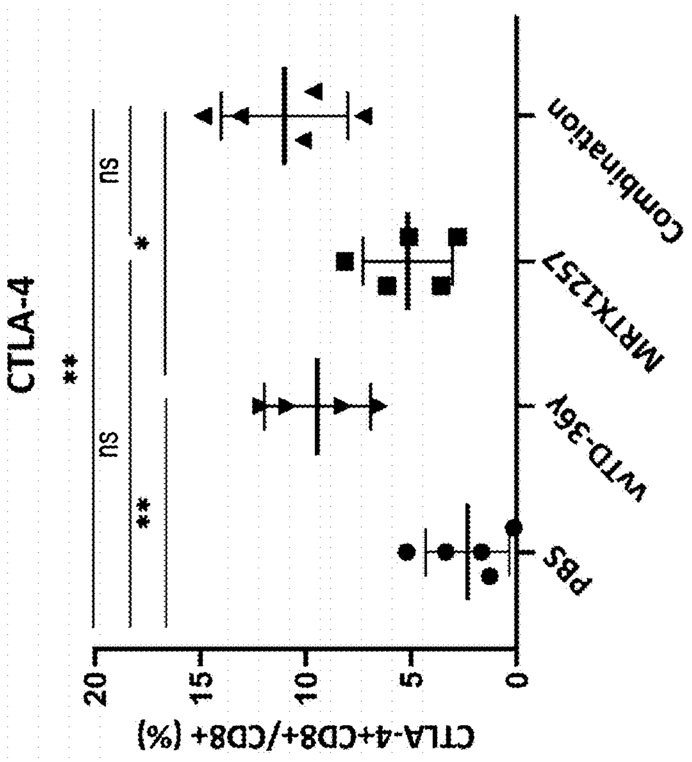
FIG. 9J shows levels of TIM-3+CD8+ T cells.
Figure 9I:
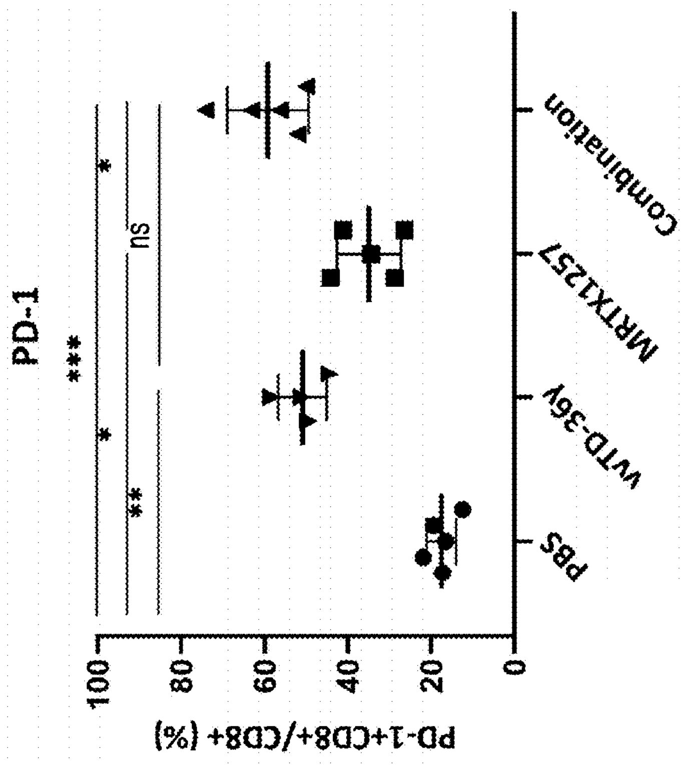
FIG. 9I shows levels of PD-1+CD8+ T cells.
Figure 9K:
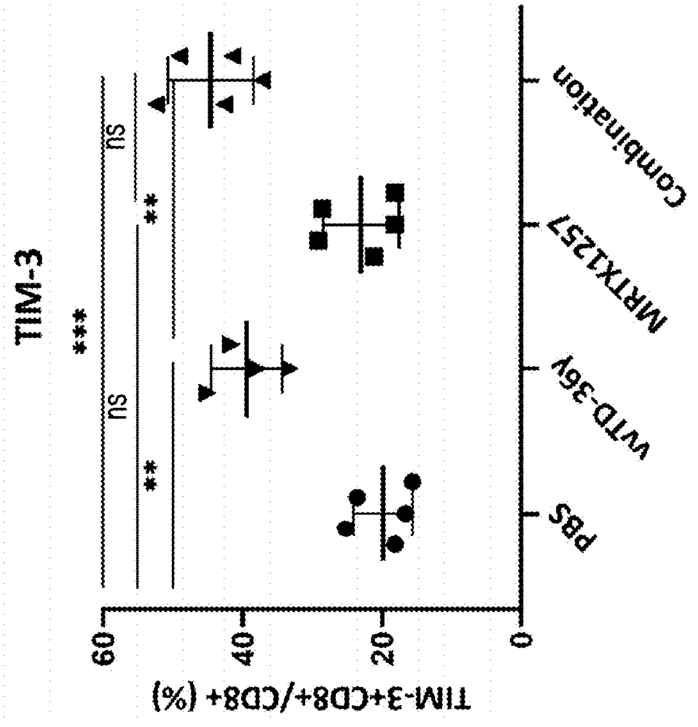
FIG. 9K shows levels of CTLA-4+CD8+ T cells.
Figure 9L:
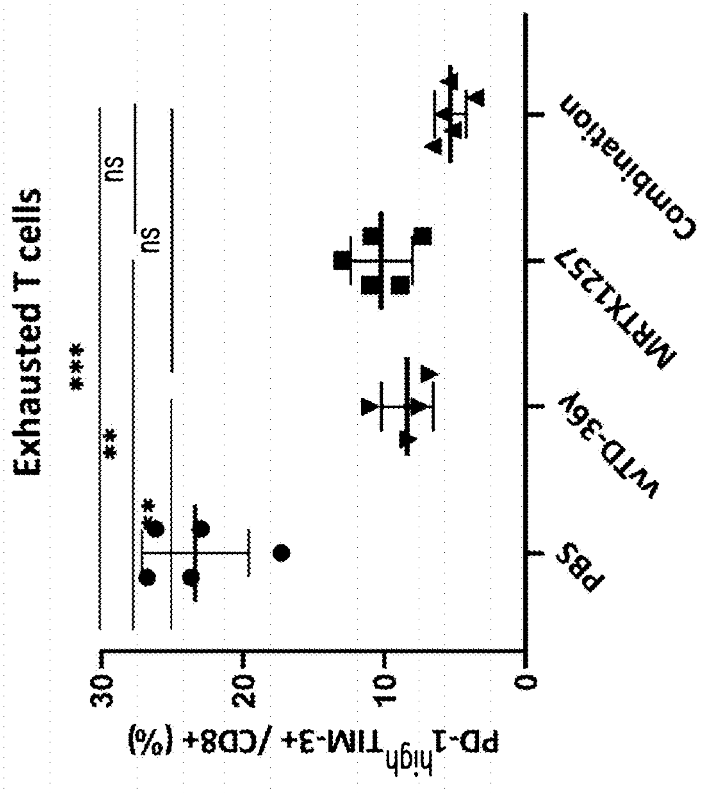
FIG. 9L shows levels of exhausted CD8+ T cell (PD1highTIM3+CD8+).
Figure 9N:
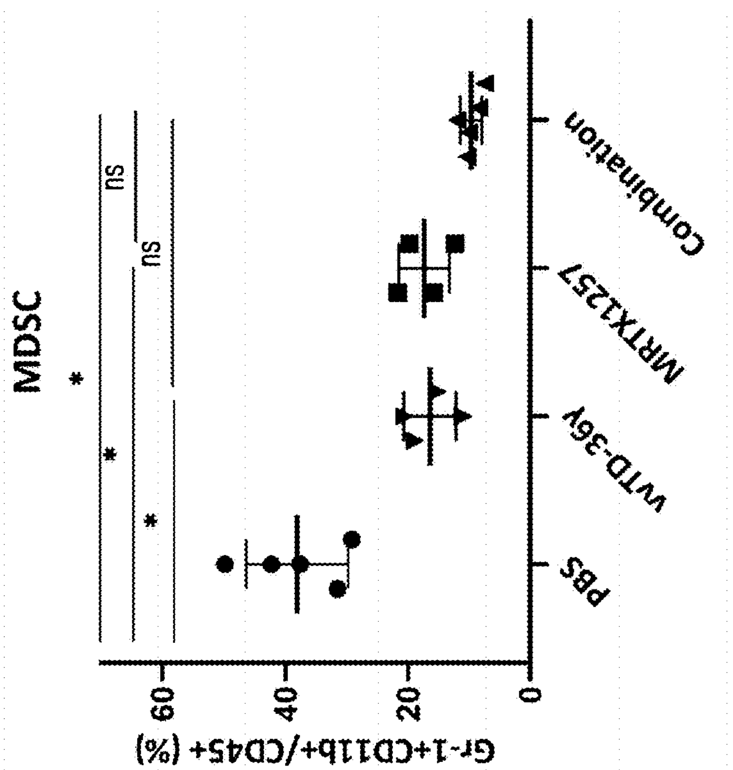
FIG. 9N shows levels of regulatory T cells (CD4+Foxp3+).
Figure 9M:
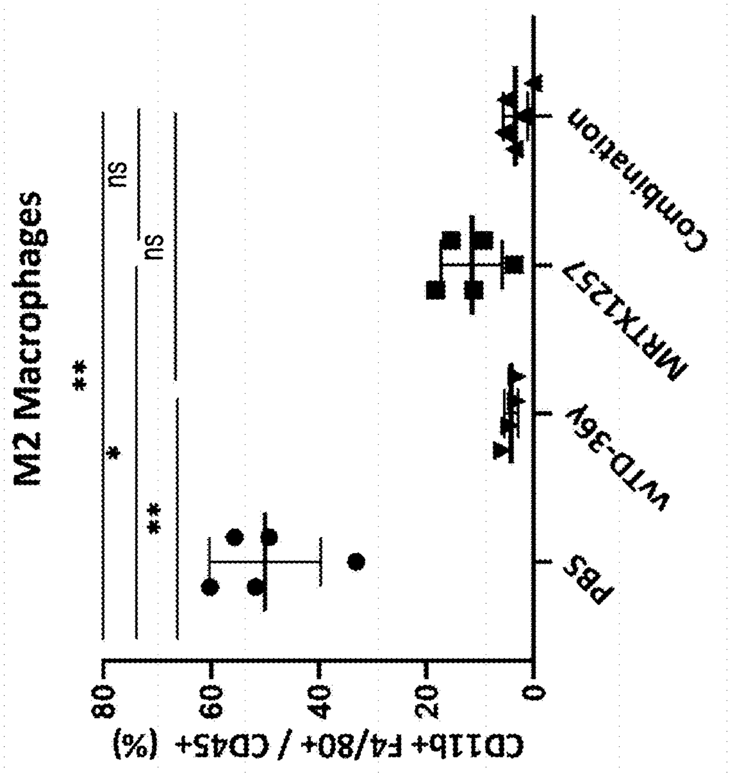
FIG. 9M shows levels of M2-like Macrophages (CD206+F4/80+).
Figure 9O:
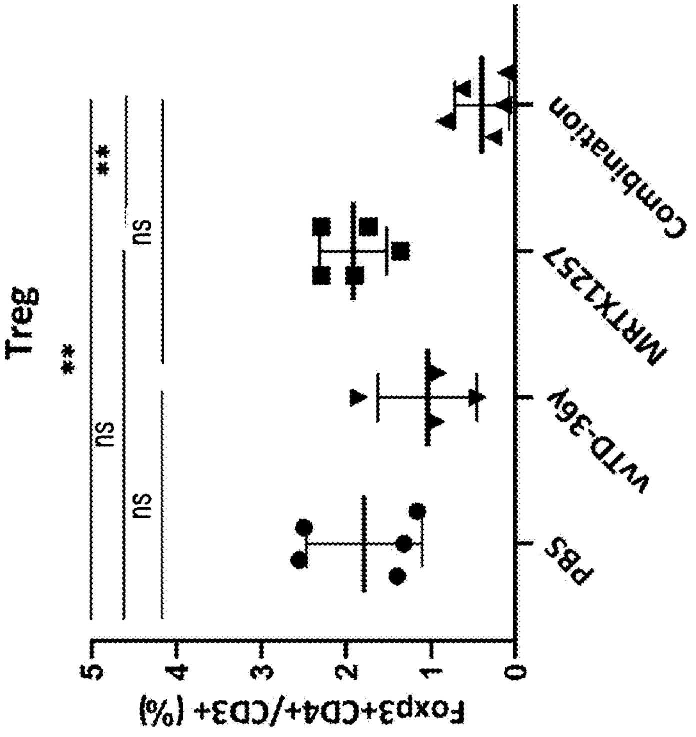
Figure 10A:
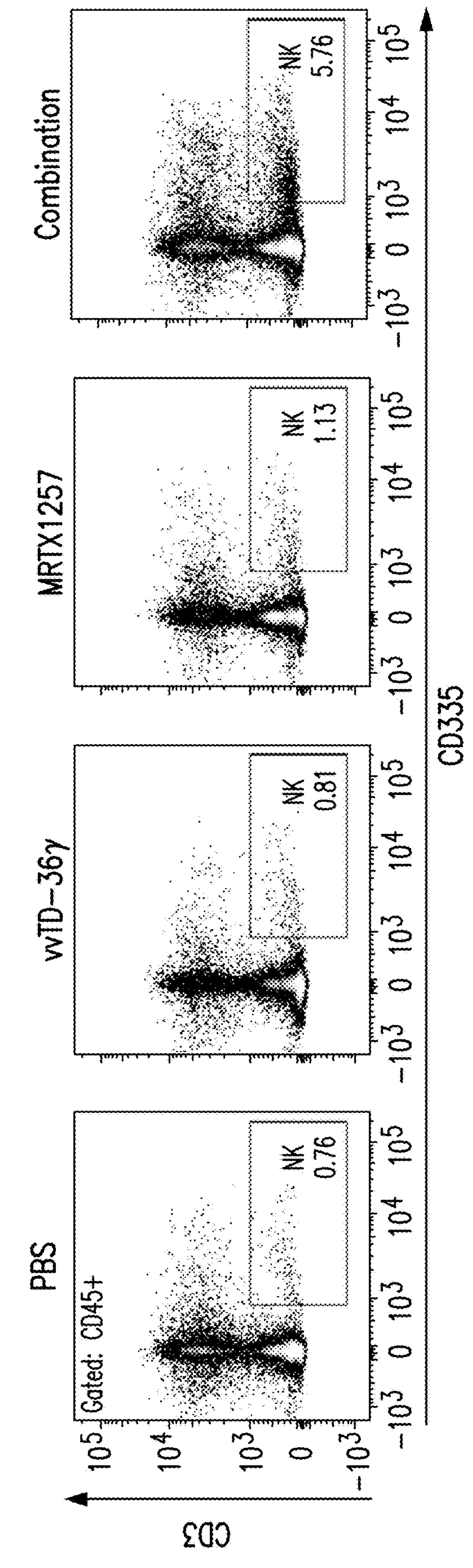
FIGS. 10A-10L illustrate representative flow cytometric analysis of percentages of TILs 11 days post-treatment.
Figure 10B:
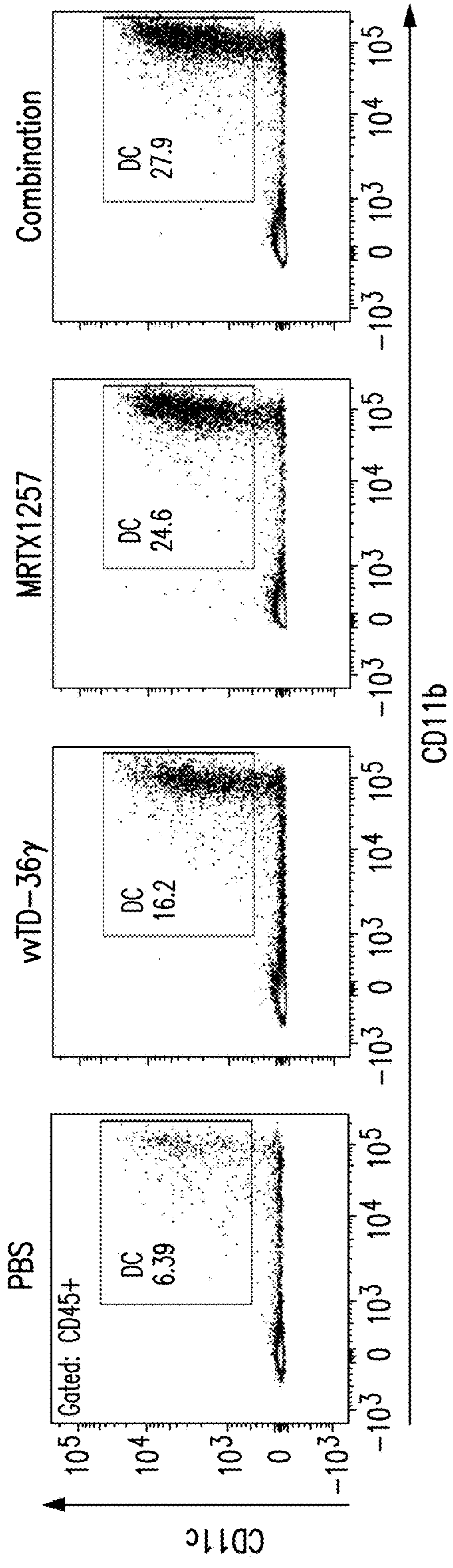
Figure 10C:
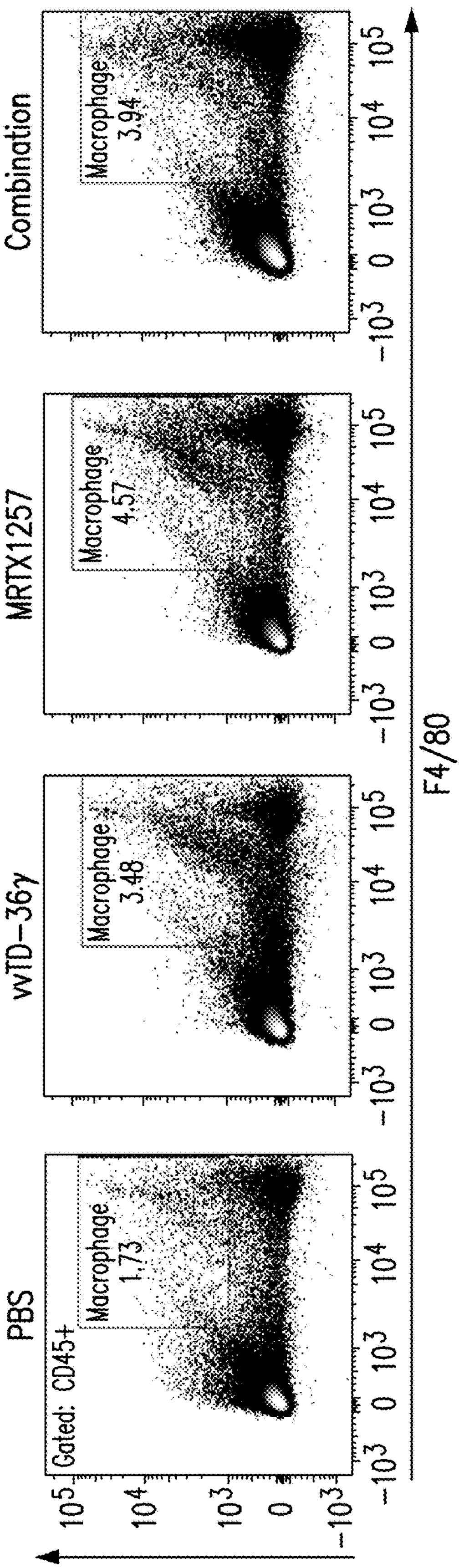
Figure 10D:
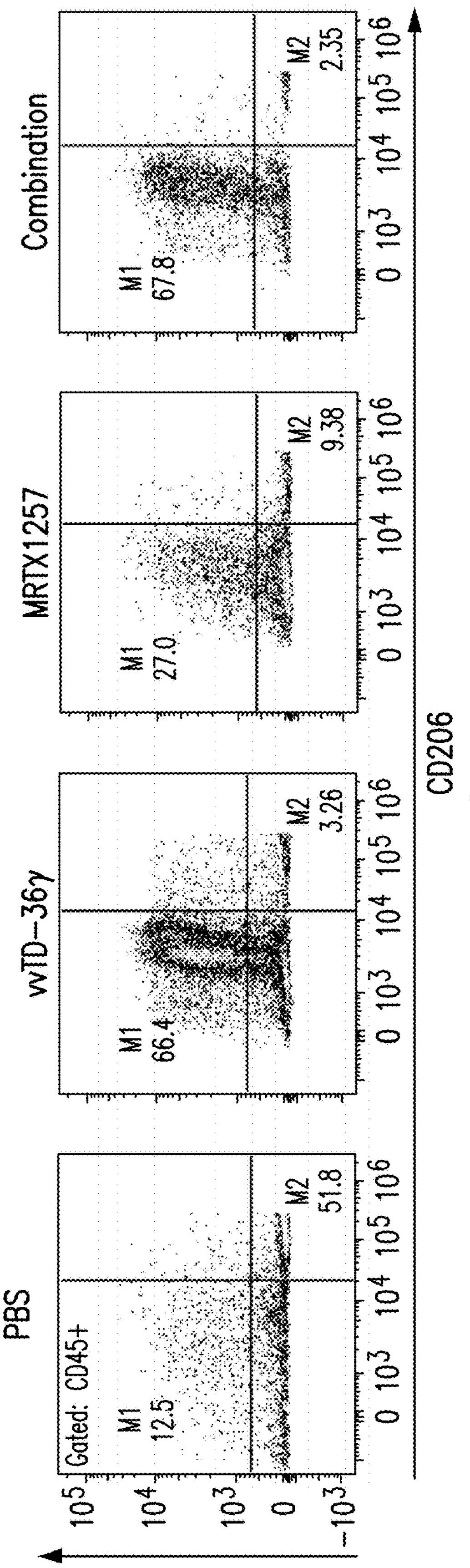
Figure 10E:
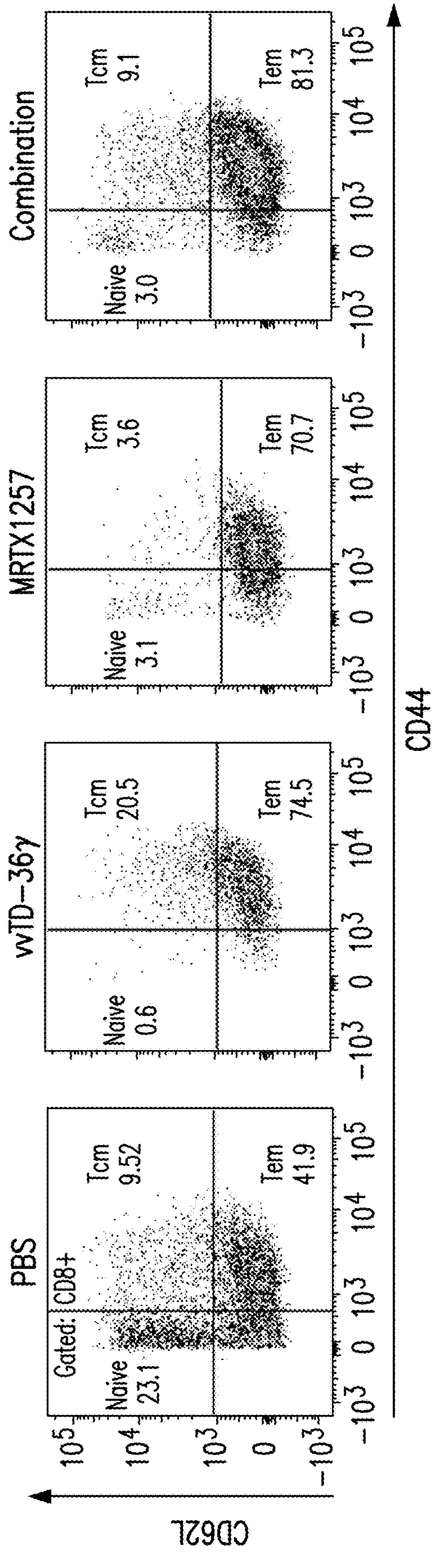
Figure 10F:
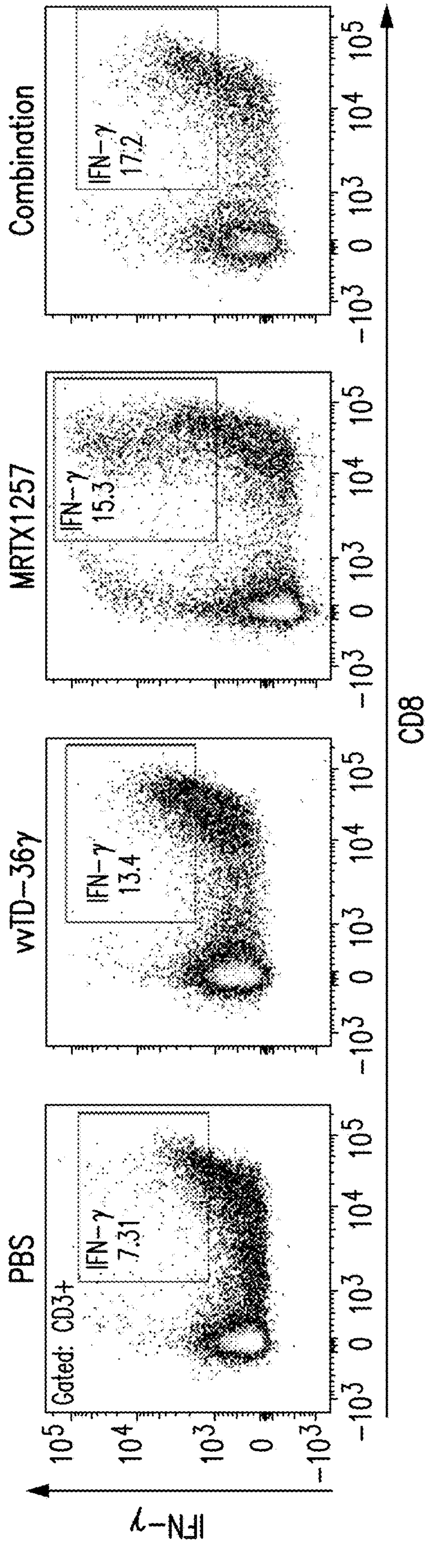
Figure 10G:
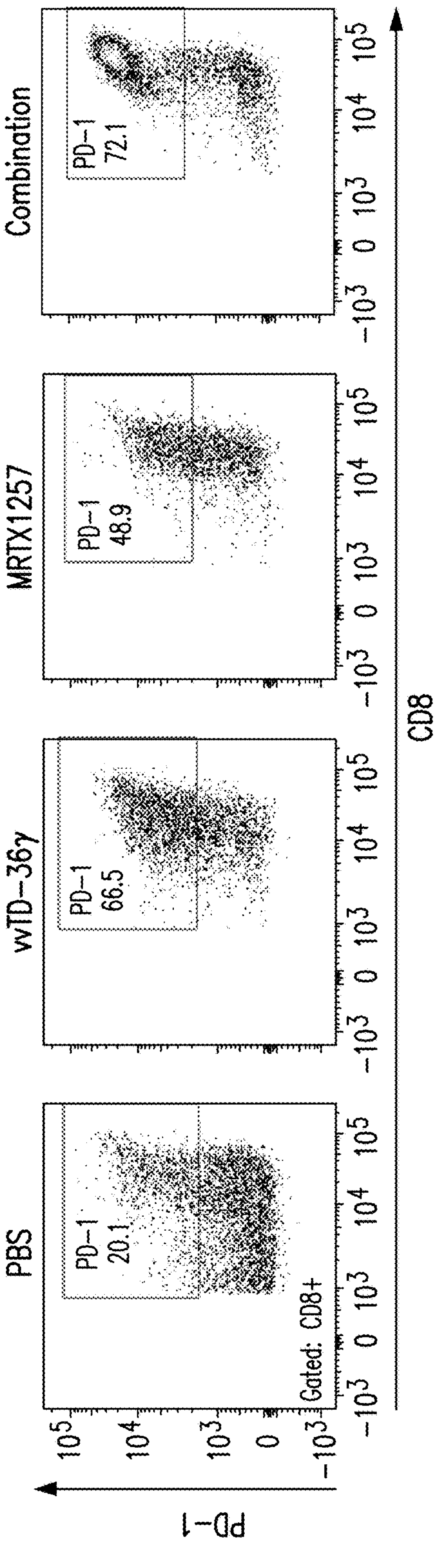
Figure 10H:
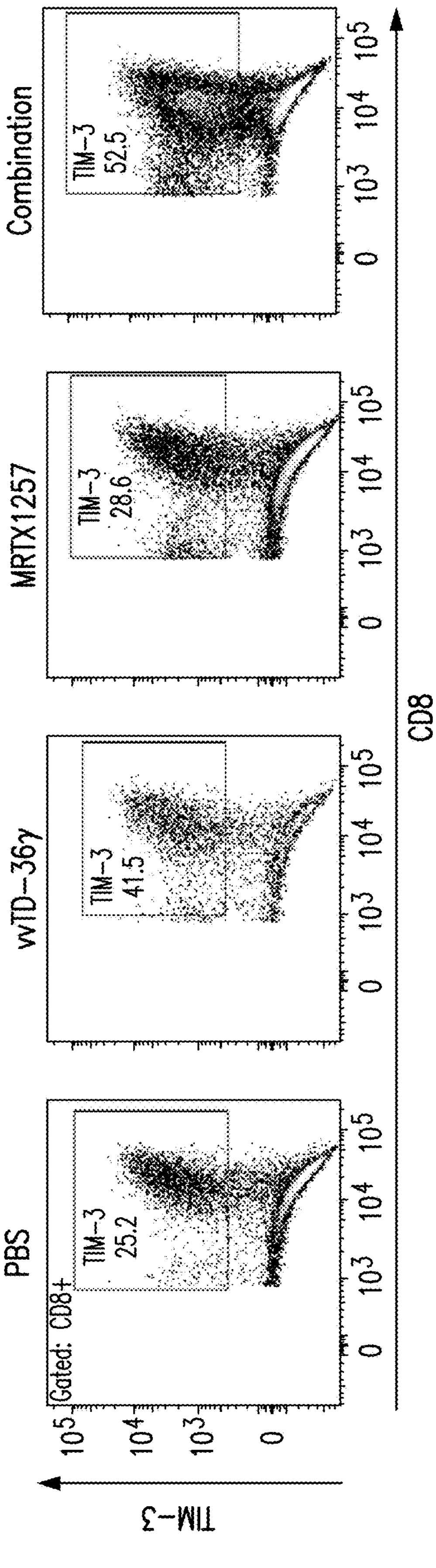
Figure 10I:
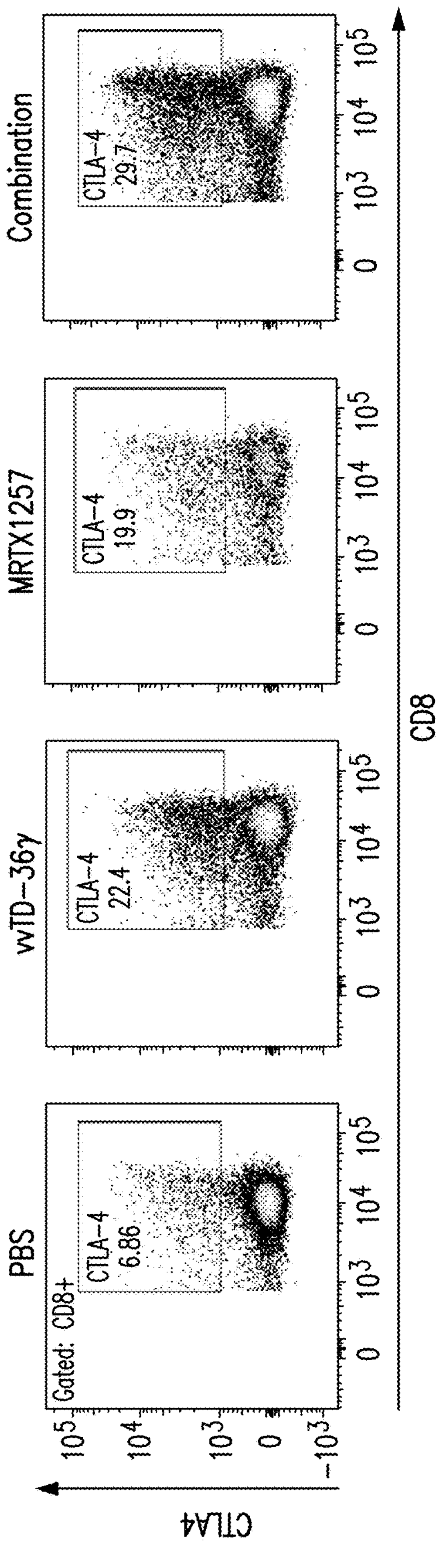
Figure 10J:
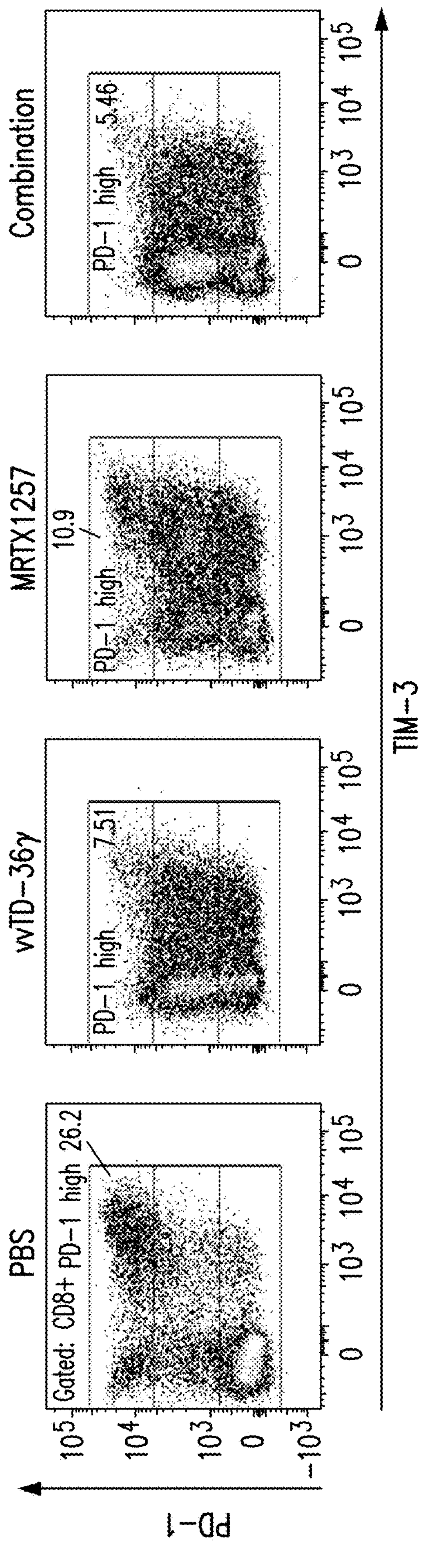
Figure 10K:
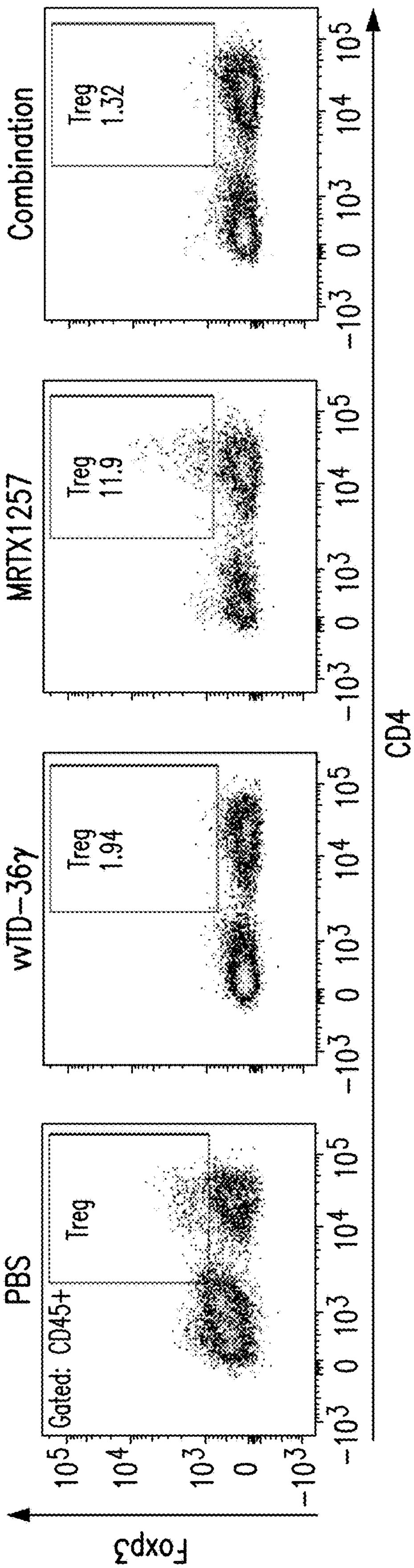
Figure 10L:
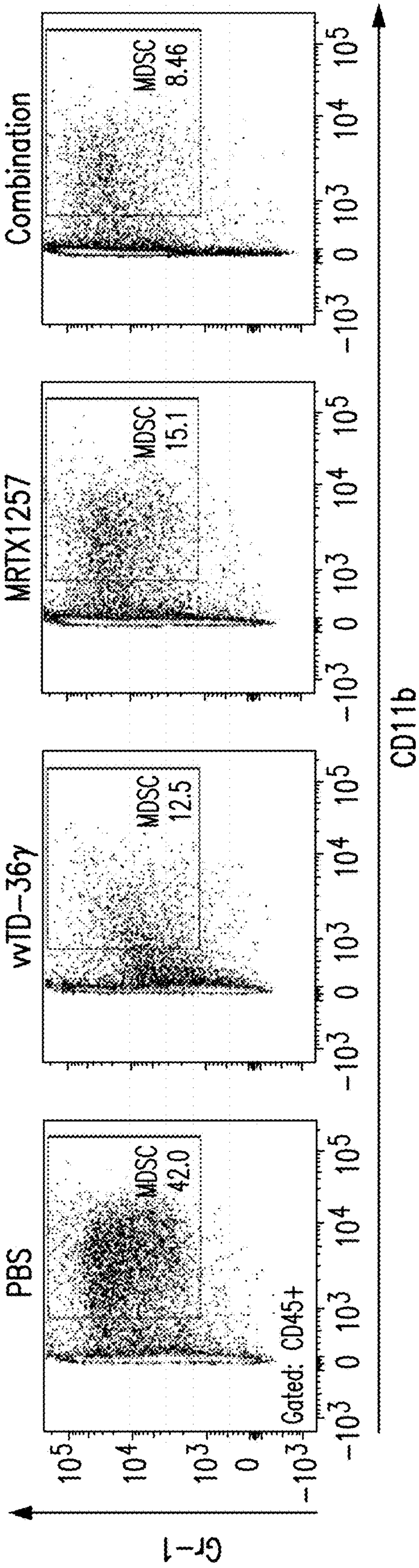
Figure 11A:
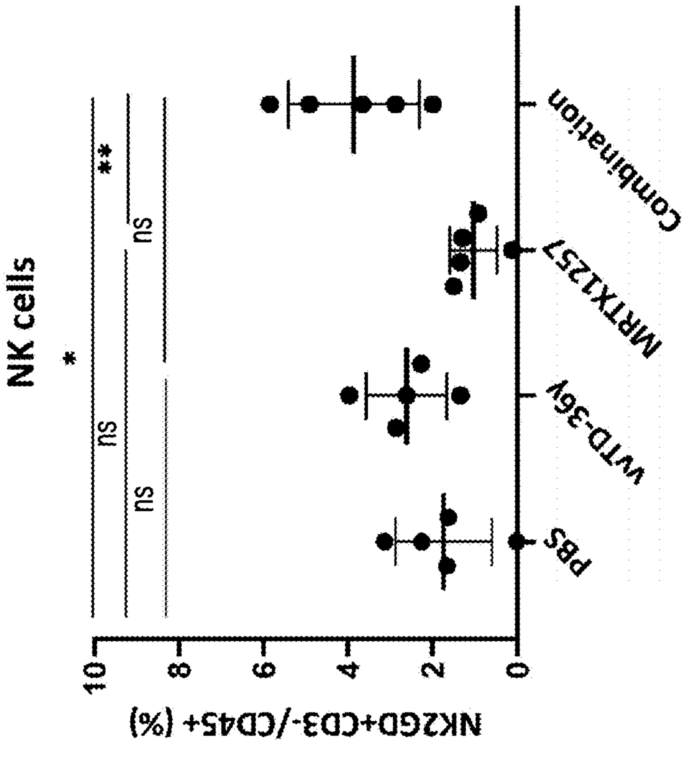
FIGS. 11A-11O illustrate immune status change in the splenocytes 6 days after vvTD-IL36γ alone or combined with MRTX1257 treatments.
Figure 11B:
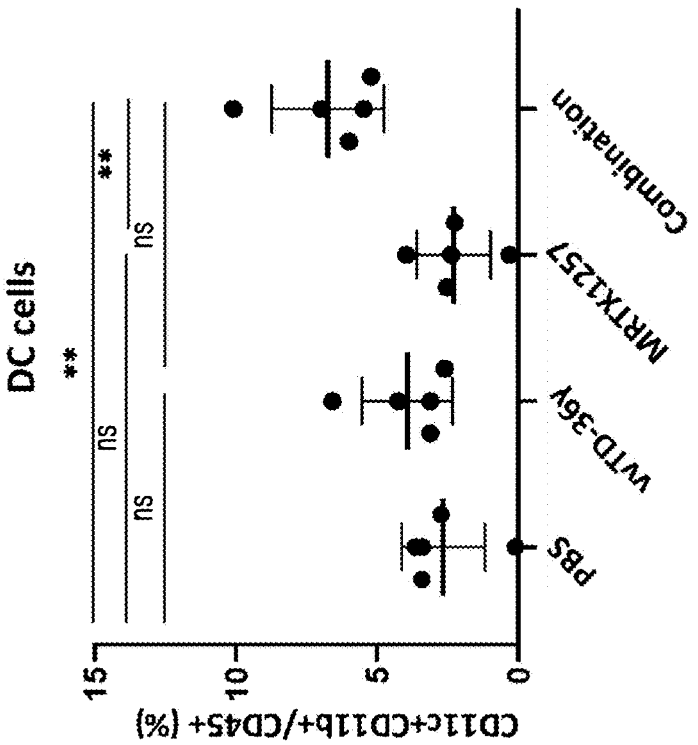
Figure 11D:
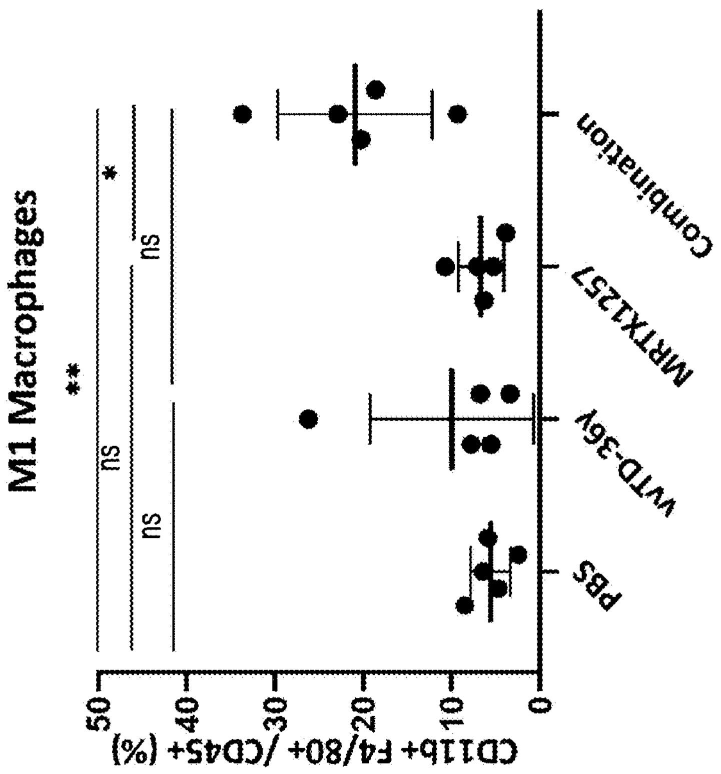
Figure 11C:
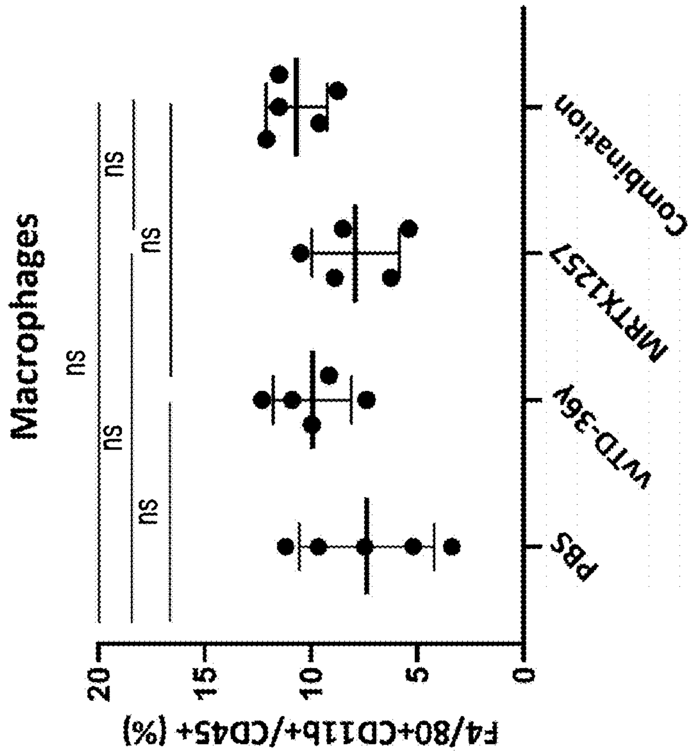
Figure 11F:
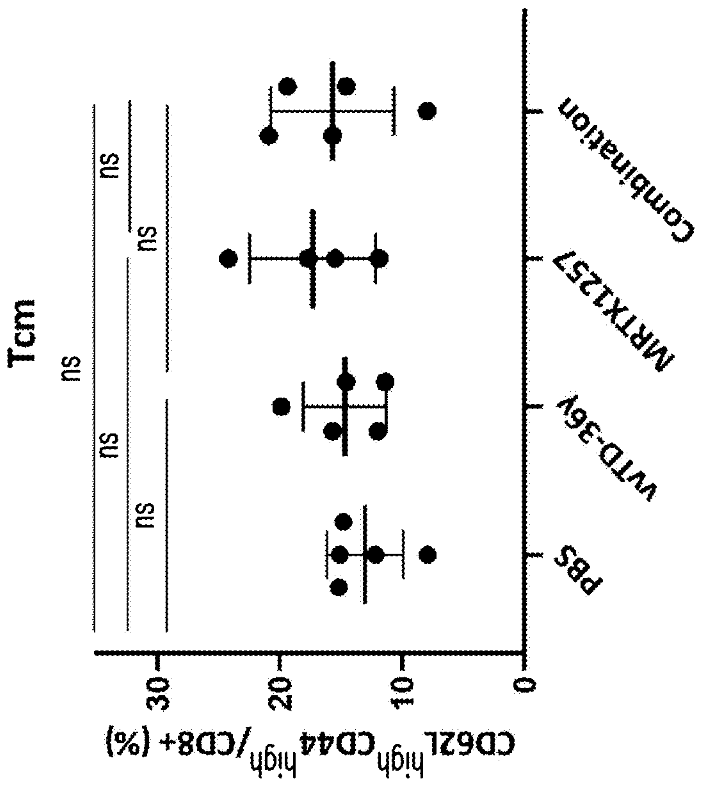
Figure 11E:
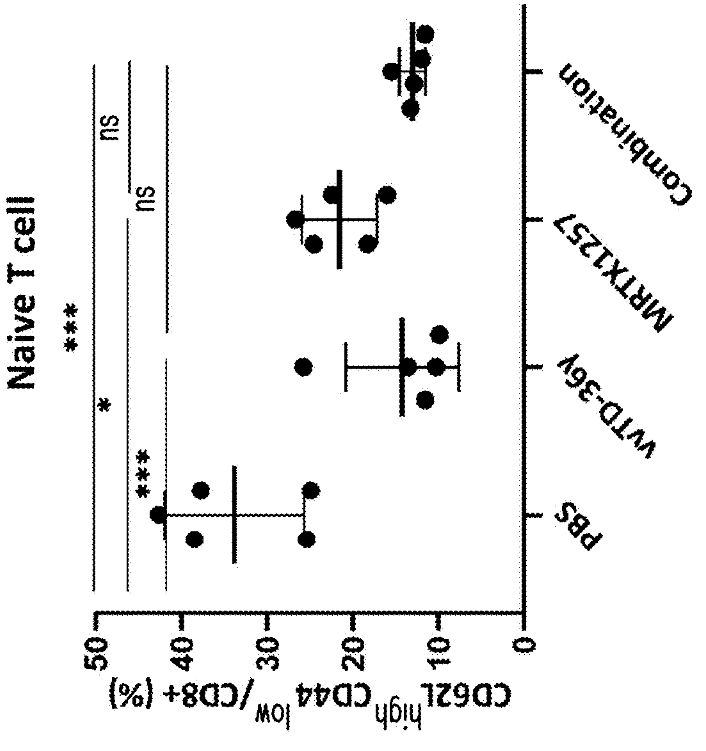
Figure 11H:
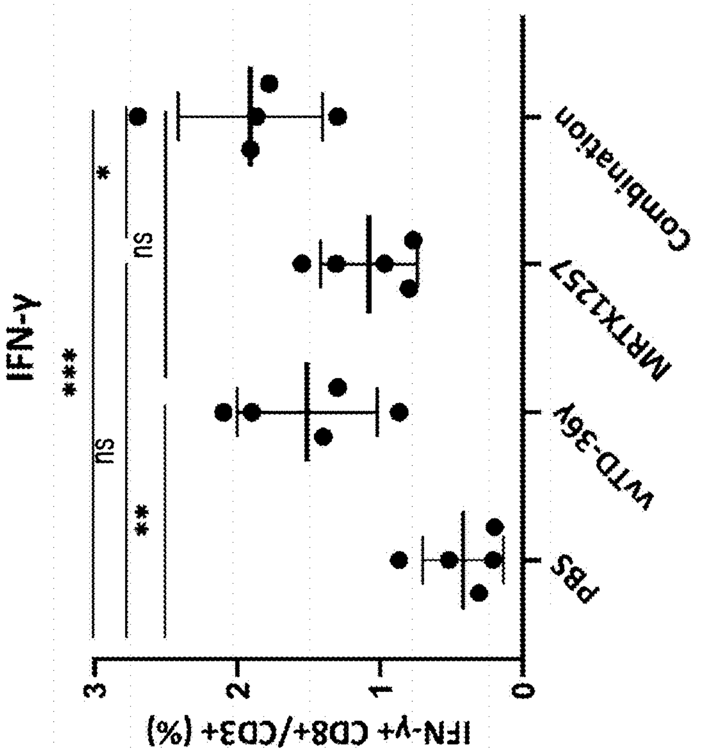
Figure 11G:
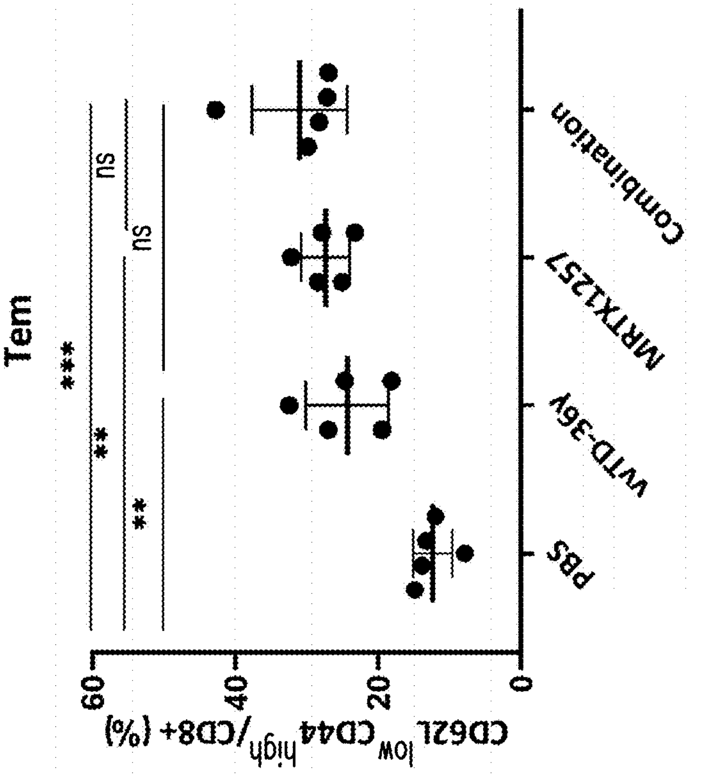
Figure 11I:
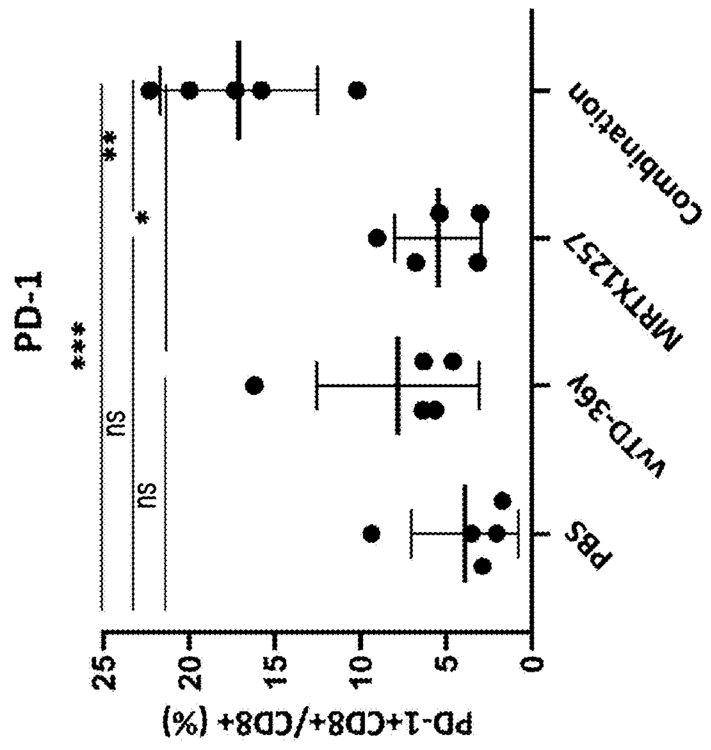
Figure 11J:
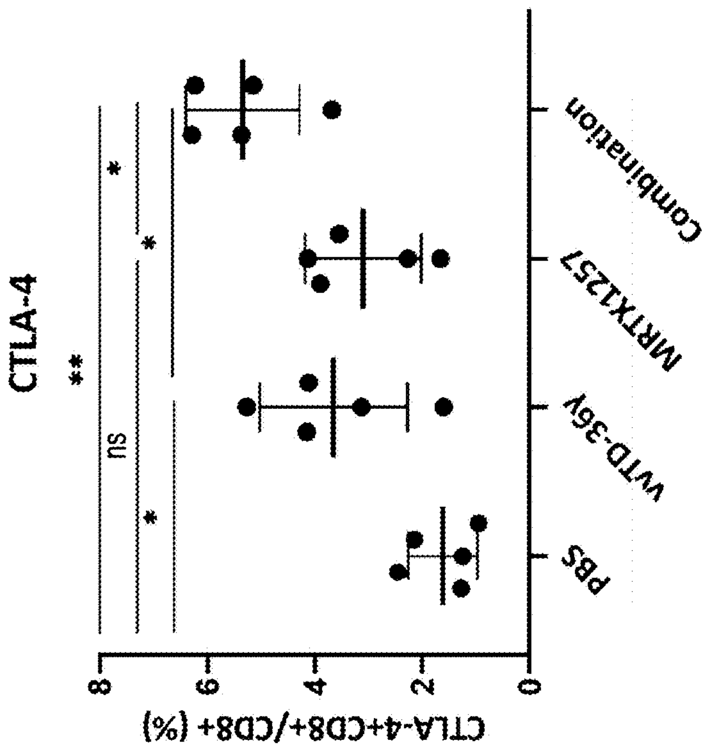
Figure 11L:
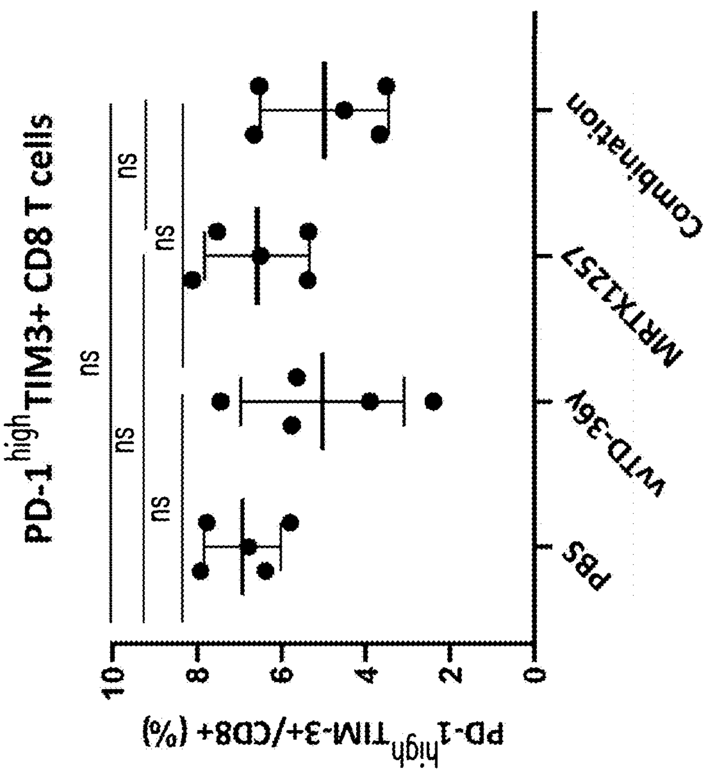
Figure 11K:
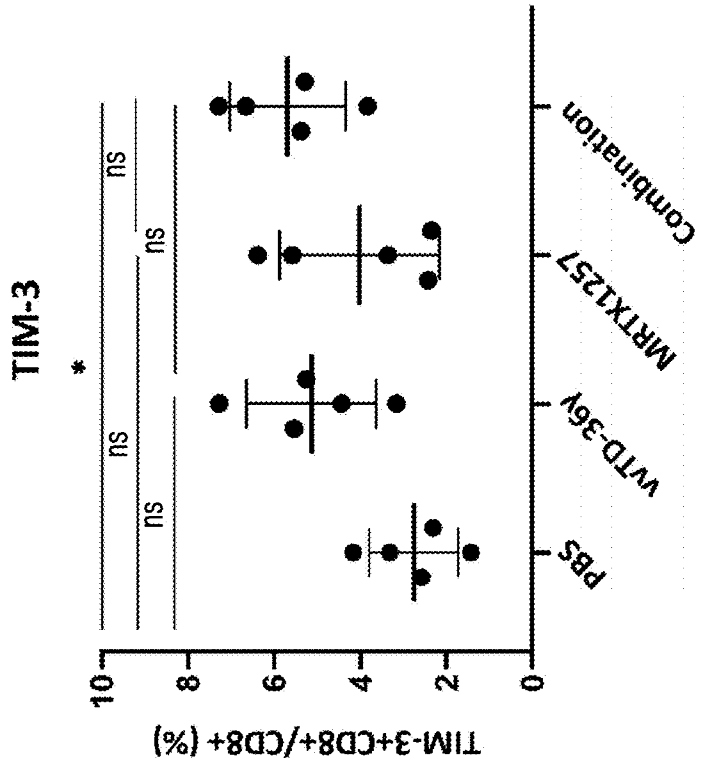
Figure 11N:
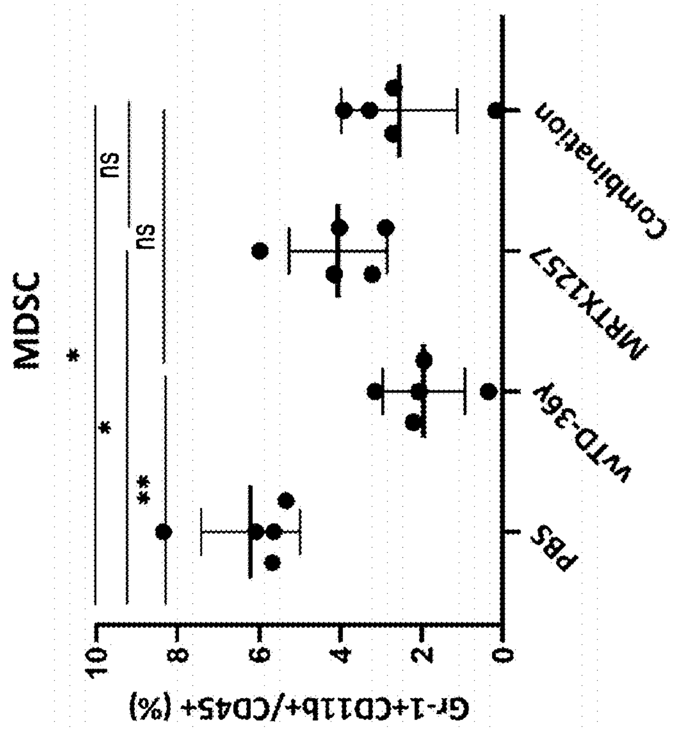
Figure 11M:
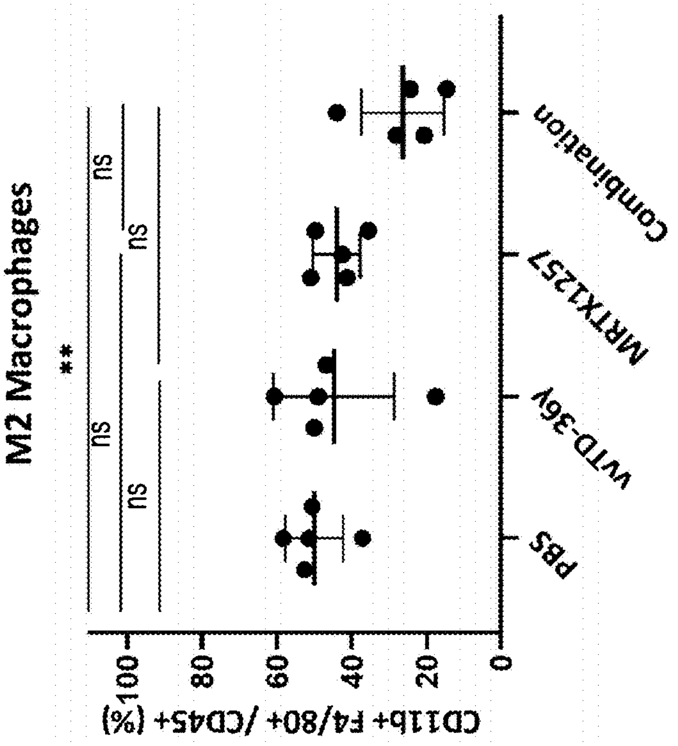
Figure 11O:
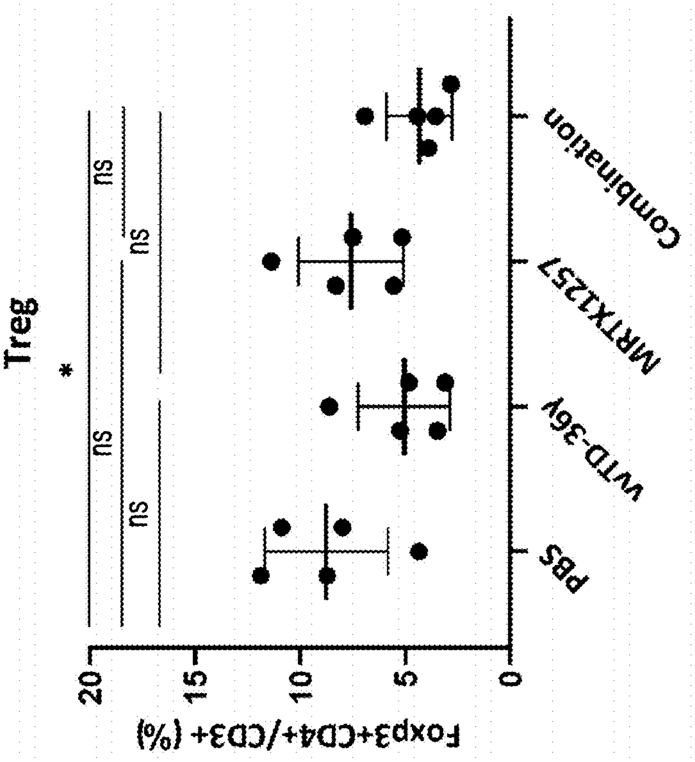
Figure 12B:
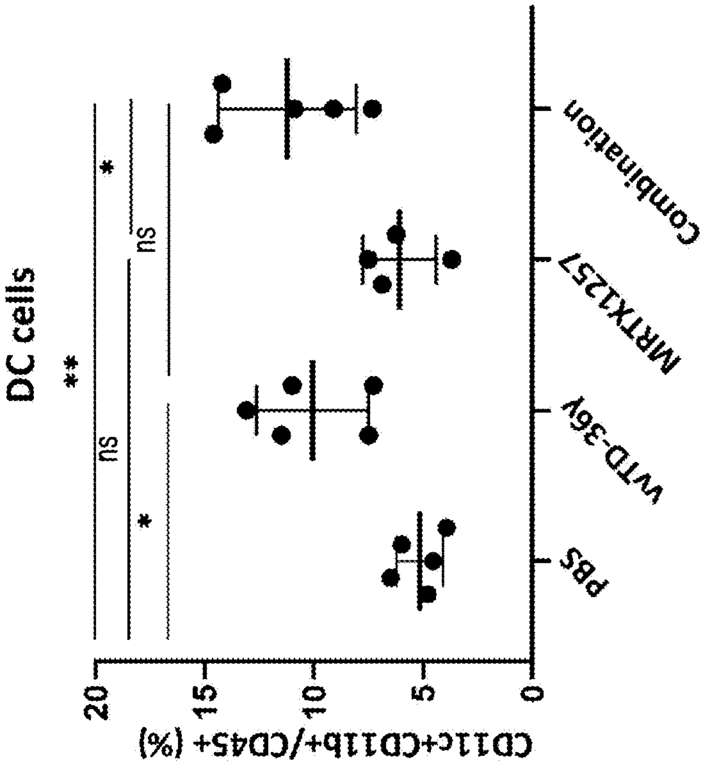
FIGS. 12A-12O illustrate immune status change in the splenocytes 11 days after vvTD-IL36γ alone or combined with MRTX1257 treatments.
Figure 12A:
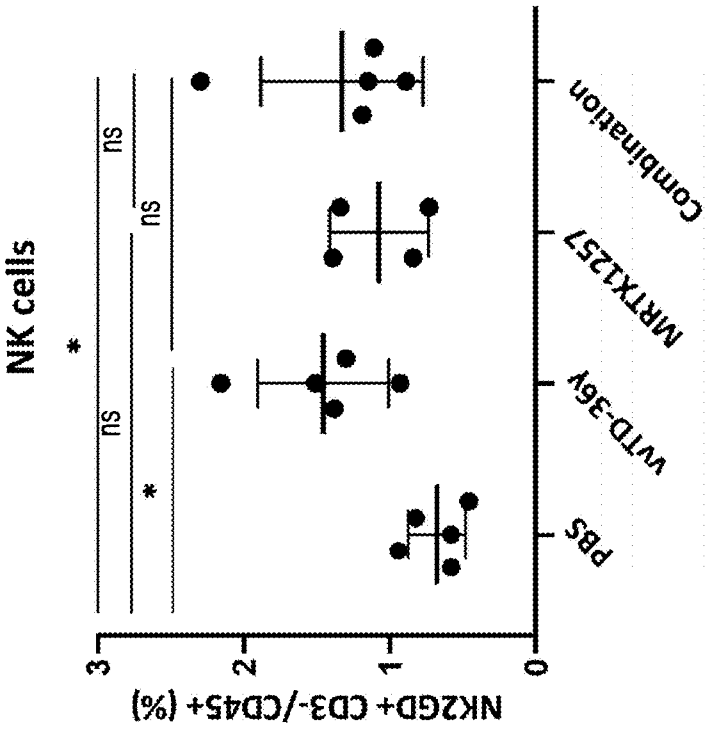
Figure 12C:
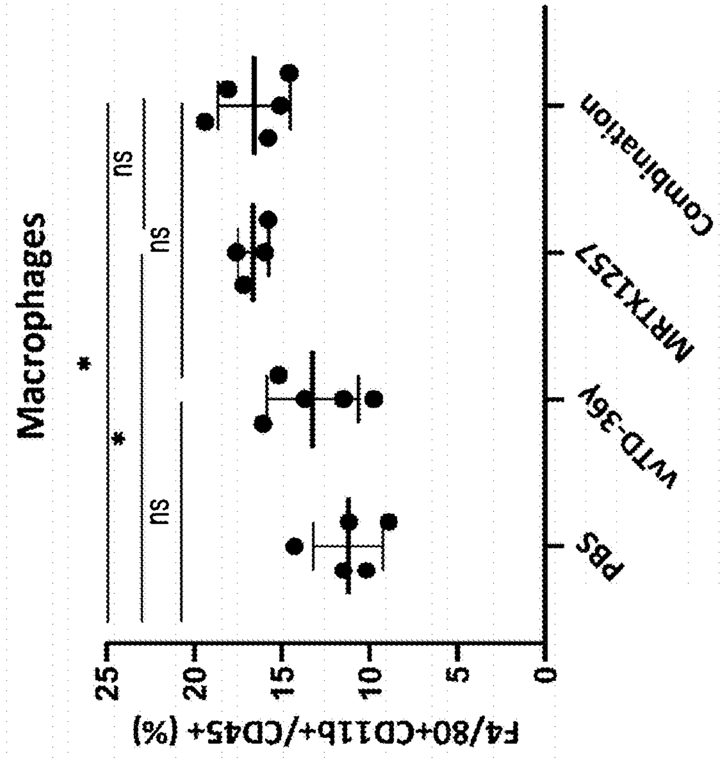
Figure 12D:
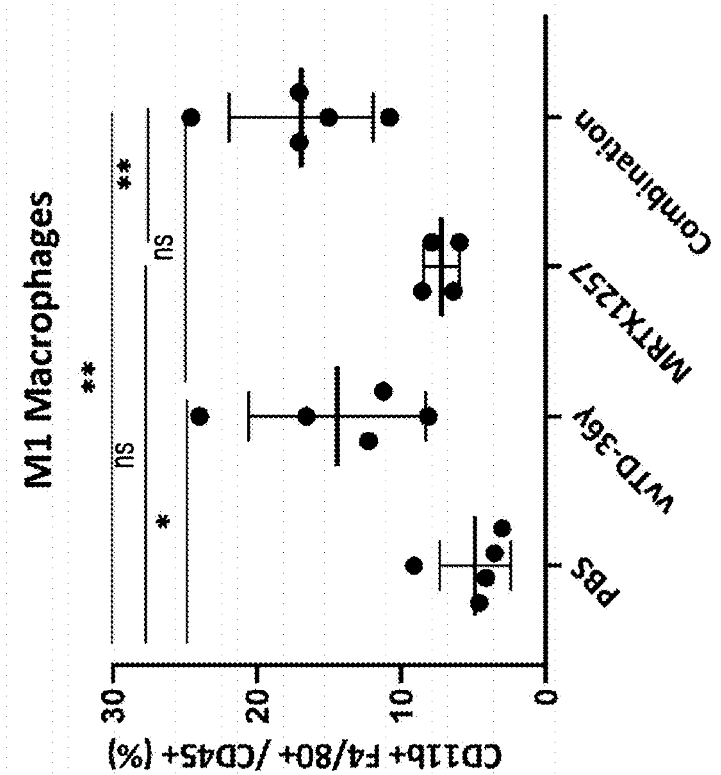
Figure 12F:
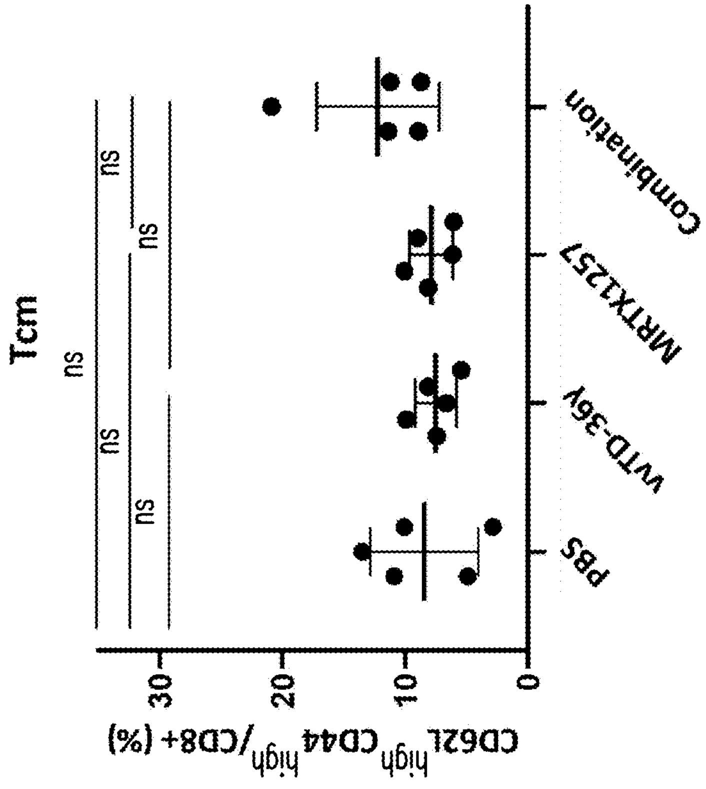
Figure 12E:
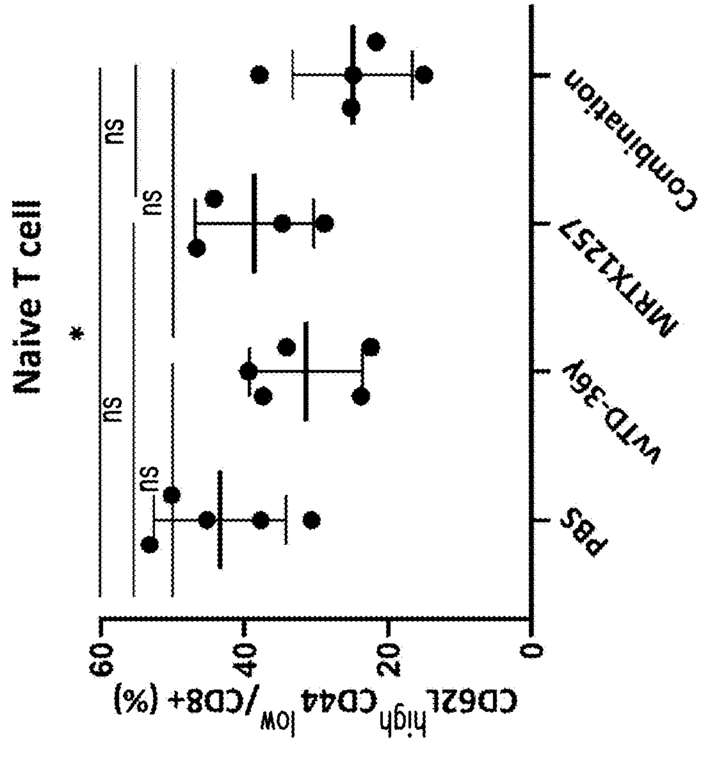
Figure 12H:
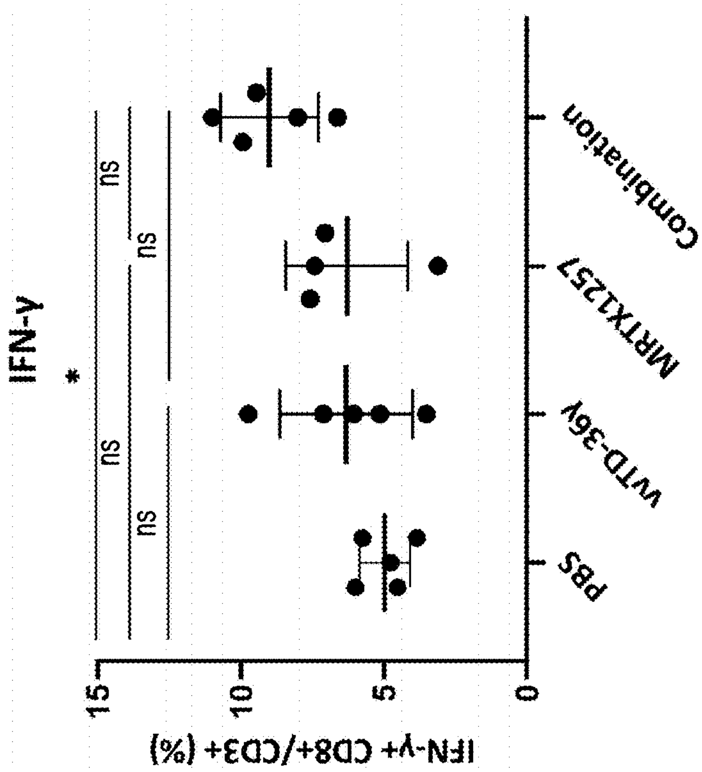
Figure 12G:
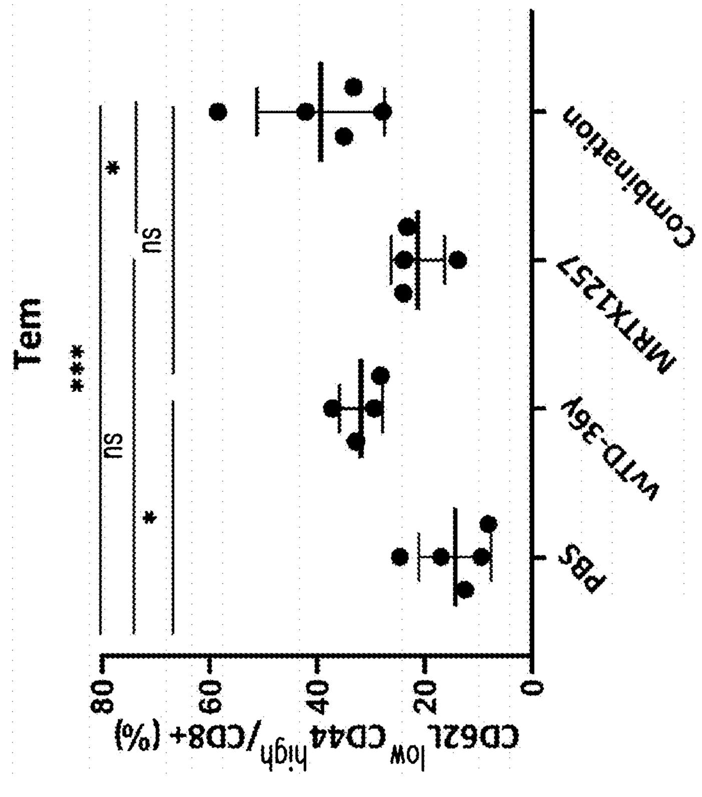
Figure 12J:
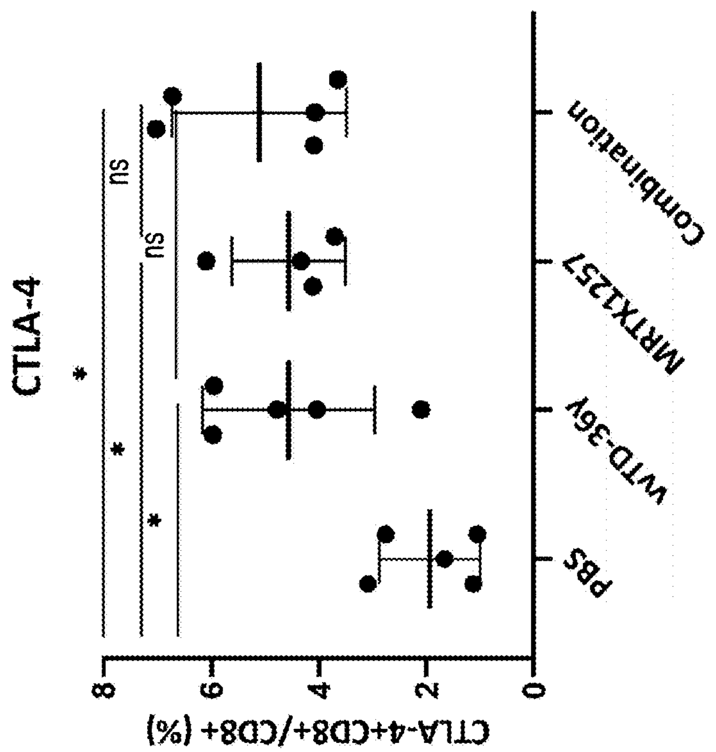
Figure 12I:
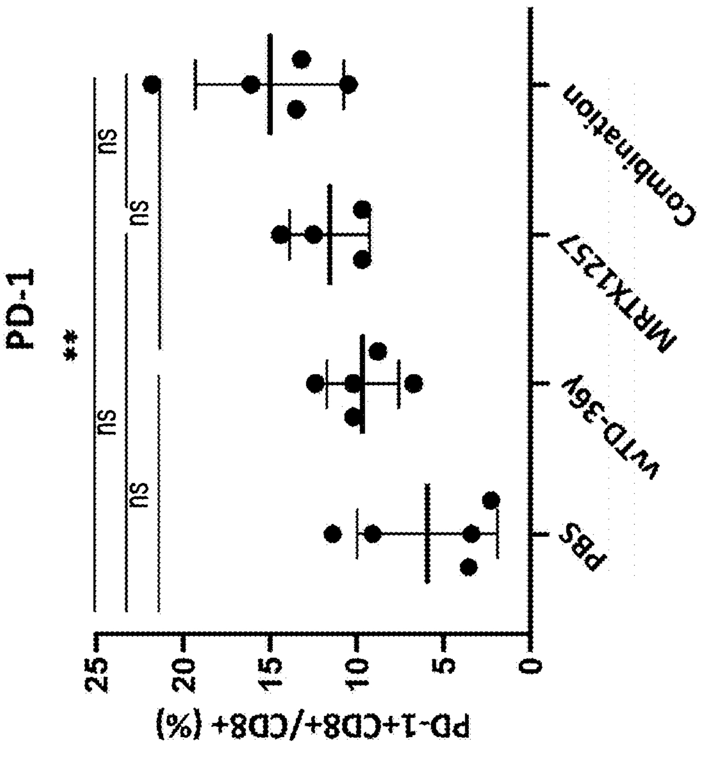
Figure 12K:
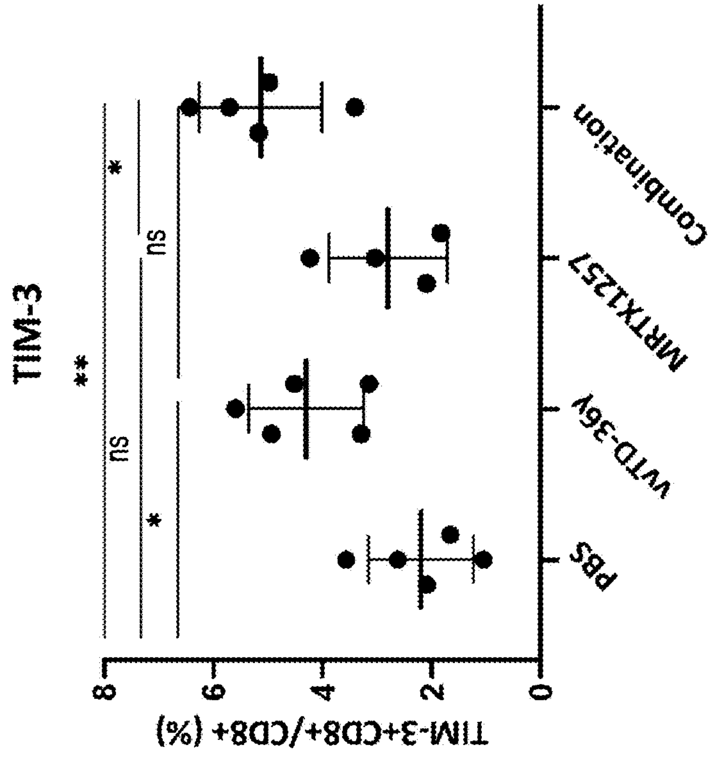
Figure 12L:
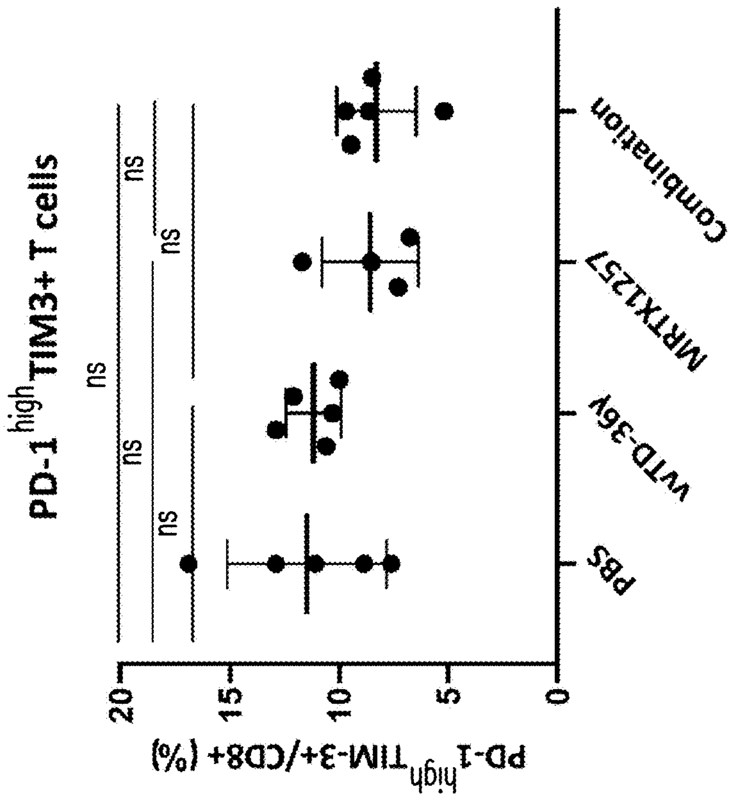
Figure 12N:
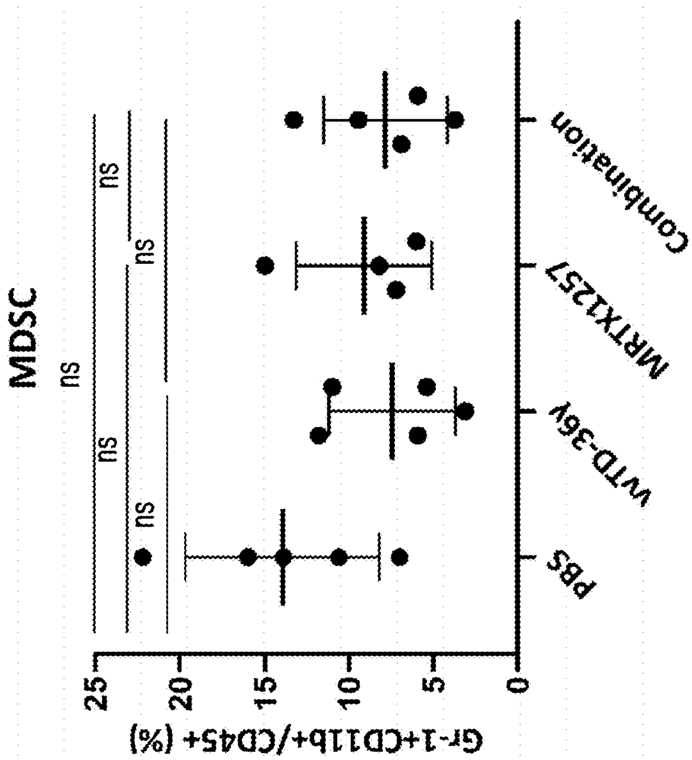
Figure 12M:
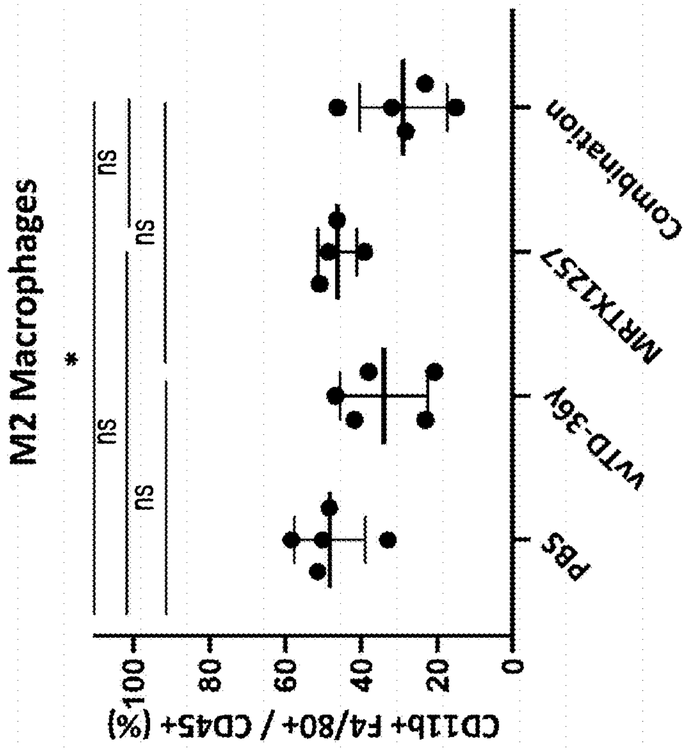
Figure 12O:
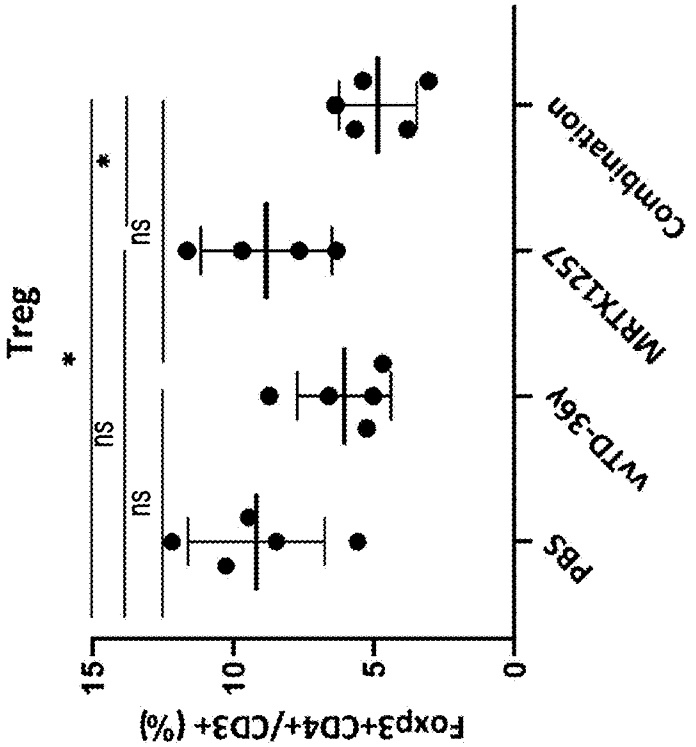

Subsets of immune cells were analyzed by flow cytometry at day 6 after therapies (FIGS. 5A-5O). The data set on day 11 are presented in FIGS. 9A-9O. There were NK and DC cells in treated groups (FIGS. 5A-5B). There were more macrophages (FIG. 5C), and more importantly more M1-like macrophages in all treated groups ($p<0.05$ compared to PBS) (FIG. 5D). In all treated groups, both Tn and Tcm were reduced (FIGS. 5E-5F), accompanied by a concurrent increase of Tem (FIG. 5G). IFN-γ+CD8+ and PD-1+ CD8+ T cells were increased, indicating activated cytotoxic T cells (FIG. 5H-5I). However, CTLA-4+CD8+ T cells were increased in all treated groups (FIG. 5J). Tim-3+CD8+ T cells were not increased in monotherapy groups but enhanced in dual therapy group (FIG. 5K). Interestingly, PD-1hiTIM-3+CD8+ T cells, as previously shown to be highly exhausted, were reduced significantly in all treated groups ($p<0.01$ between PBA and MRTX1257; $p<0.001$, PBS versus vvTD-IL36γ or dual therapy) (FIG. 5L). Finally, three key types of immunosuppressive cells were examined (FIGS. 5M-5O). M2 macrophages were reduced in all treated groups (FIG. 5M). MDSCs and Treg cells were reduced in vvTD-IL36γ and dual treated groups, but not in MRTX1257 group (FIGS. 5N-5O).

Figure 6A:
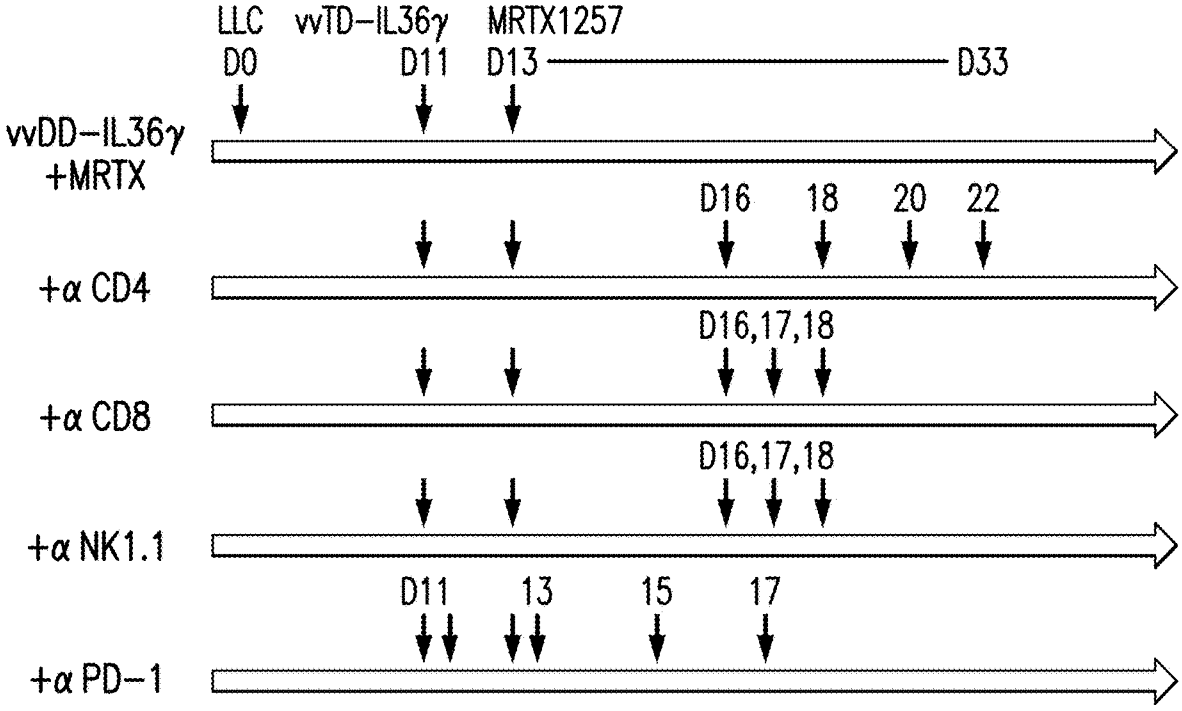
FIGS. 6A-6E illustrate that vvTD-IL36γ or/and MRTX 1257 stimulates CD8+ T cell-dependent anti-tumor immunity, and the triple combination led to the best therapeutic efficacy. B6 mice bearing subcutaneous LLC tumors, when reached size of 100-150 $mm^3$ (around D11), were injected i.t. with PBS or 2.0e6 PFU vvTD-IL36γ, and/or MRTX1257 (on day 13 post-inoculation) daily by oral gavage for 3 weeks. For cell depletion of CD8+, CD4+ and NK cells, anti-CD8 Ab (250 μg per injection), anti-CD4 Ab (150 μg per injection), or PK136 (300 μg per injection), were i. p. injected into mice.
Figure 6B:
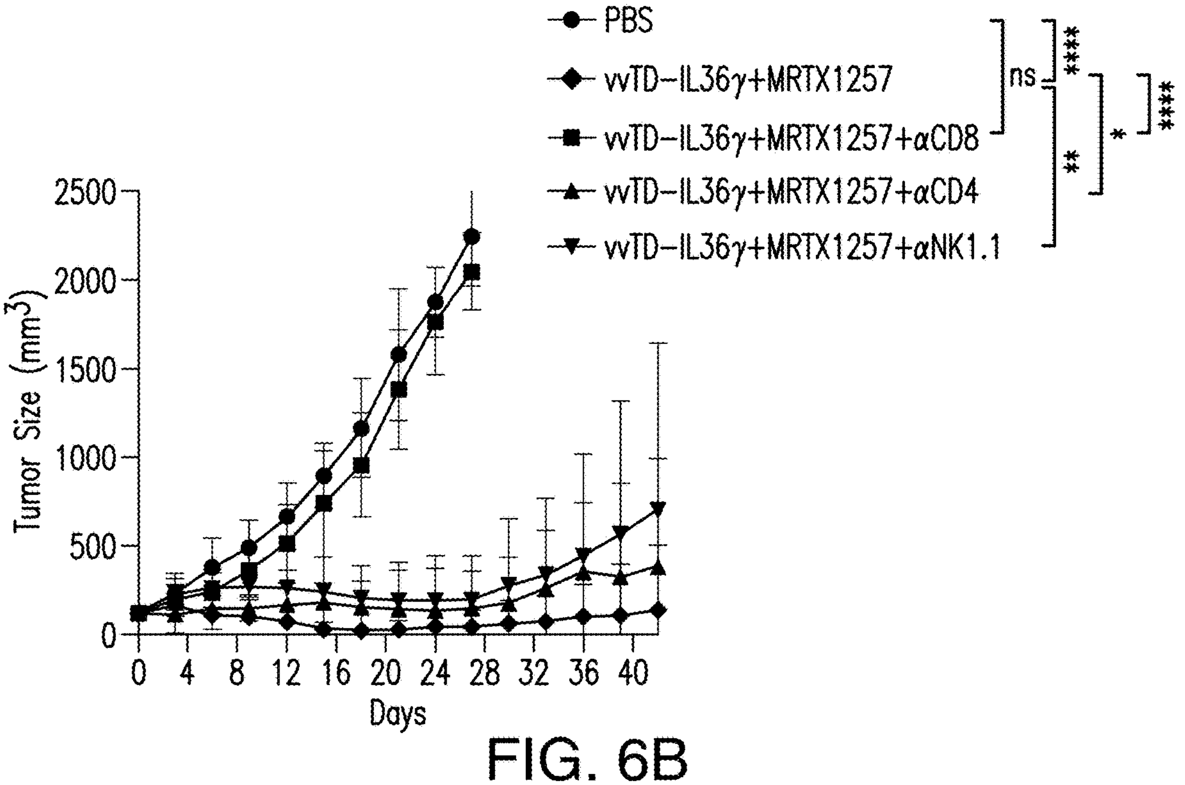
Figure 6C:
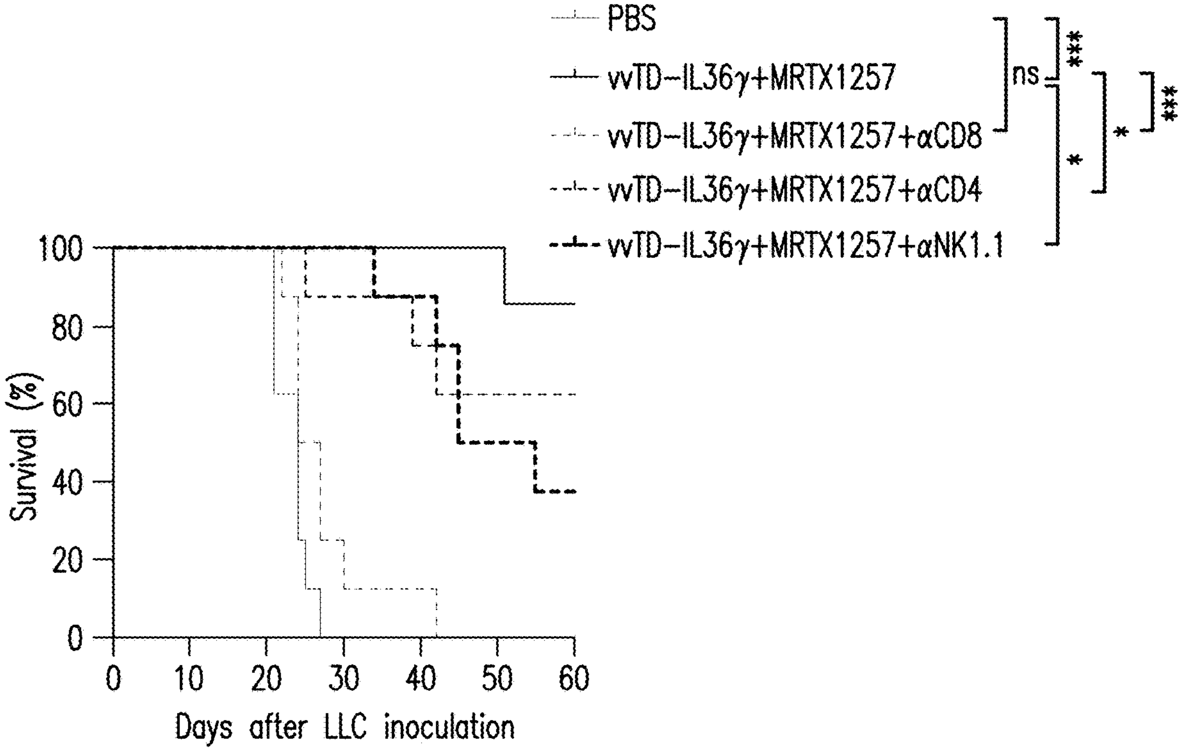

Having demonstrated that both MRTX1257 and OV can elicit adaptive antitumor immunity, the hypothesis that one or more types of immune cells play an essential role right after the treatments have been initiated was tested. FIG. 6A shows the schedule of the treatments, and antibodies to deplete CD4+, CD8+ and NK cells in LLC-bearing mice. In vivo experiments were performed on LLC tumor model treated with dual therapy and some groups with an additional infusion of antibodies to deplete CD4+, CD8+ or NK1.1+ cells. The tumor growth was plotted in FIG. 6B. The tumor sizes in mice in the PBS group reached over 2,000 $mm^3$ by day 24. In contrast, the group with dual treatment (vvTD-IL36γ and MRTX1257) remained baseline on day 42, the end of the plot. When depleted with either CD4 or NK cells, there were small, but significant loss of efficacy ($p<0.05$ for NK, and $p<0.001$ for CD4+ cells), indicating that NK cells and CD4+ T cells play some roles in therapy. When the effect of CD8 depletion was examined, we observed a complete loss of efficacy ($p<0.0001$), indicating that CD8+ T cells play key roles in the therapeutic efficacy.

Figure 6D:
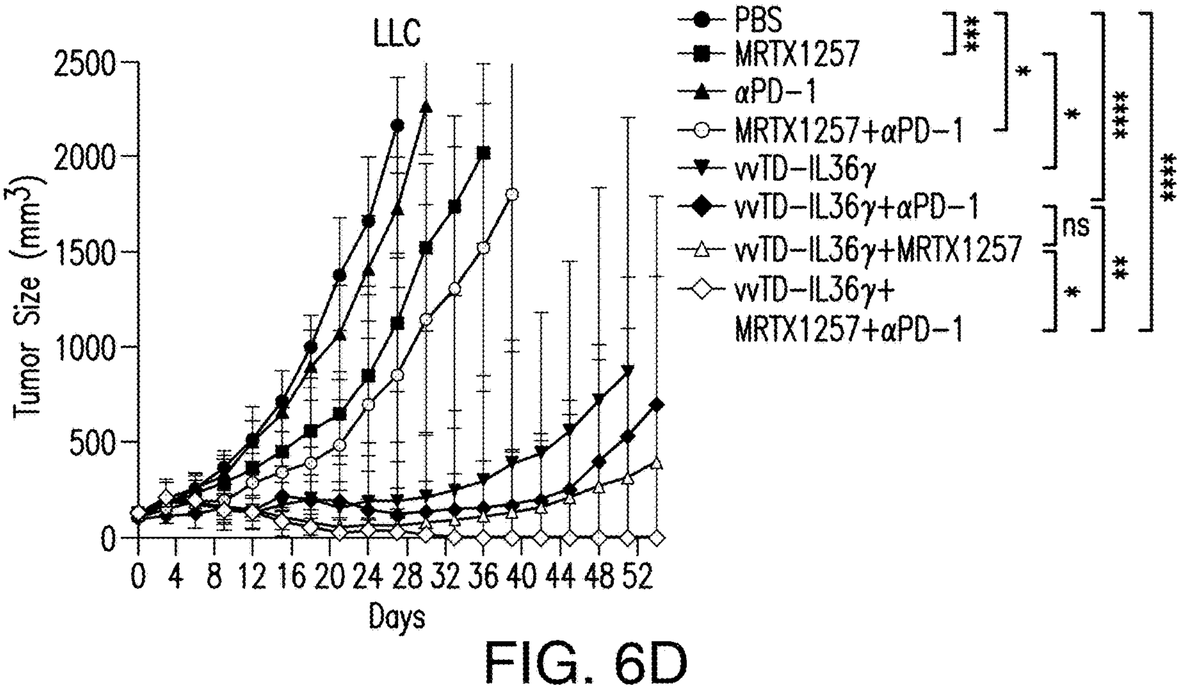
Figure 6E:
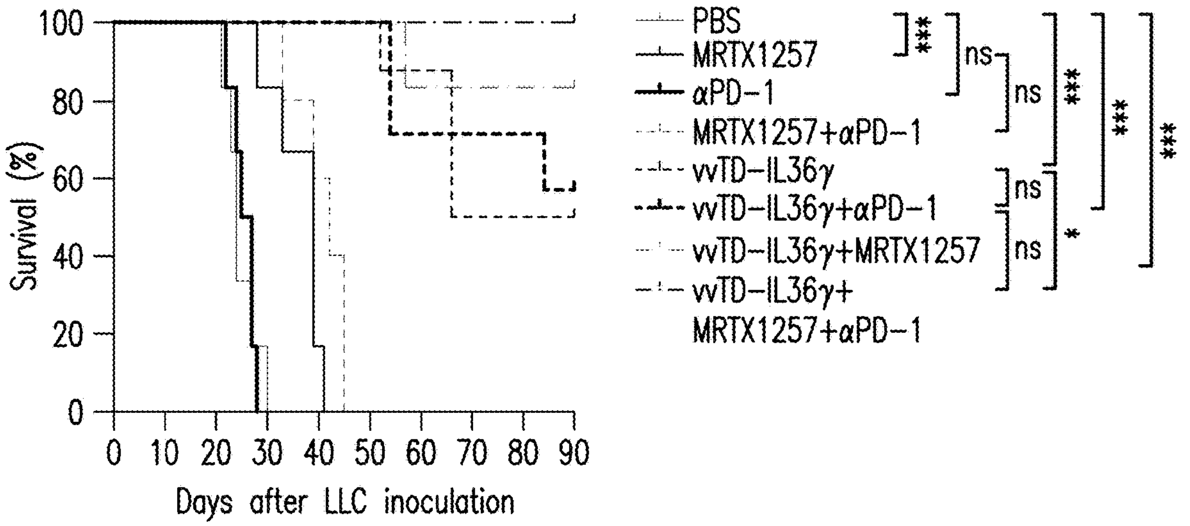

As it was shown that dual therapy enhanced PD-1+CD8+ T cells, especially PD-1hiTIM-3+CD8+ T cells in the TME (FIGS. 5I and 5L), it was determined whether anti-PD-1 immune checkpoint blockade would enhance the efficacy of dual therapy (FIGS. 6D-6E). Notably, the triple therapy group shows higher efficacy with vvTD-IL36γ+MRTX1257+αPD-1 ($p<0.05$, when compared to "vvTD-IL36γ+MRTX1257" dual therapy group). This best tumor growth inhibition by triple therapy also translated into best survival, with 100% of mice survived through the duration of the experiment (80 days) (FIG. 6E). In dual therapy, only 80% of mice survived even though there was no statistical significance between the two groups.

Figure 7A:
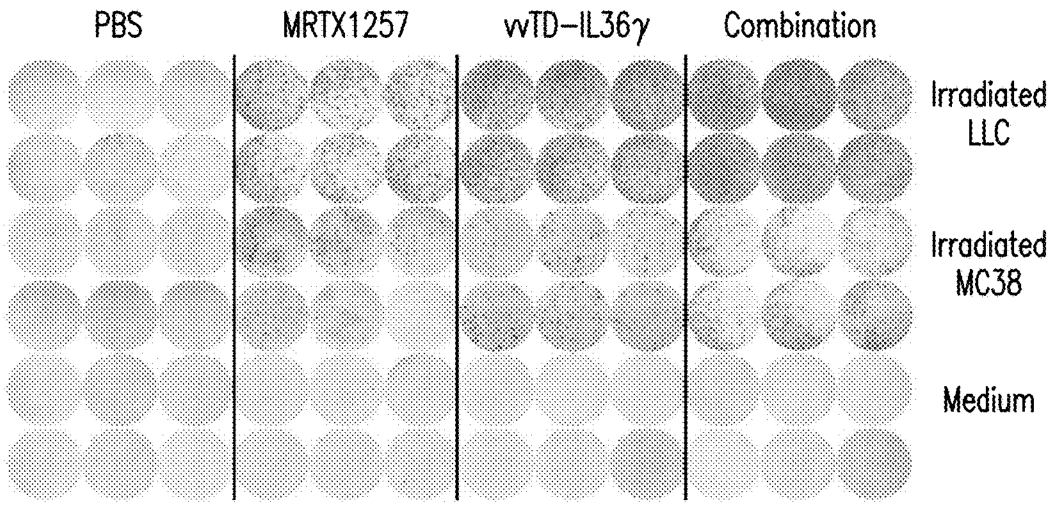
FIGS. 7A-7H illustrate that vvTD-IL36γ and MRTX1257 induced LLC tumor-specific CD8+ T cells in LLC tumor model.
Figure 7B:
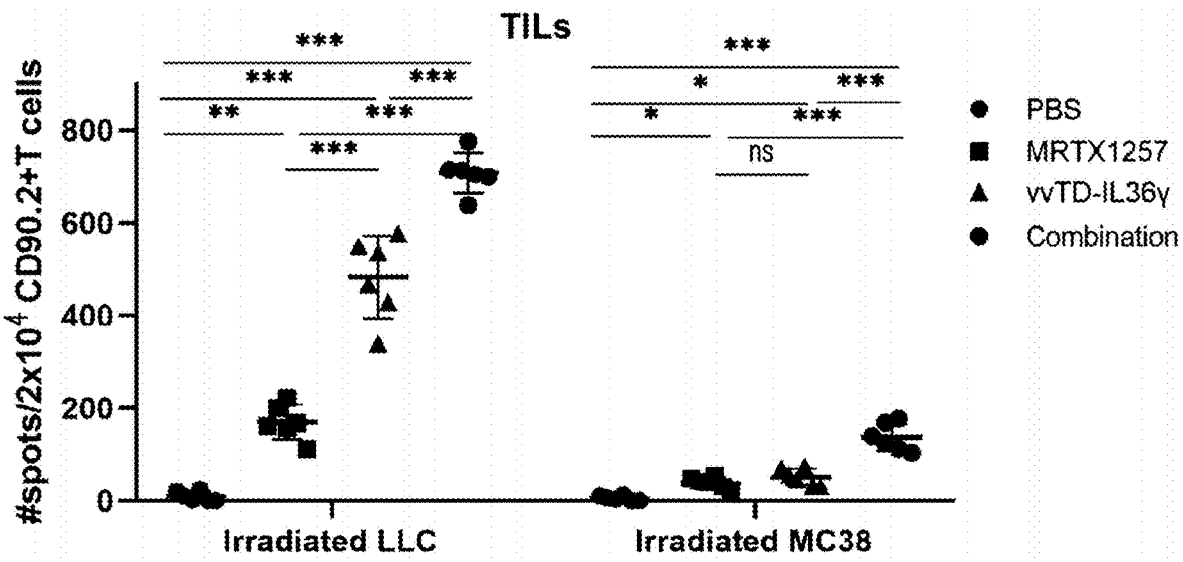

The adaptive antitumor immunity was analyzed by IFN-γ ELISpot assays and by analyzing a key activation marker molecule, 4-1BB, on T cells. First, ELISpot assay was conducted using TIL cells from tumor tissues and T cells from splenocytes isolated by CD90.2 affinity columns and incubated with irradiated LLC cells or control irradiated MC38 colon cancer cells (FIGS. 7A-7B). For TILs, there was a significant number of spots (~180) in TILs from MRTX1257 group ($p<0.01$ compared to PBS). vvTD-IL36 elicited more spots (~480). In the dual therapy group, the number of spots increased further, to ~700 ($p<0.001$, compared to either monotherapy group). There were few spots when incubated with MC38 cancer cells, indicating the tumor specificity.

Figure 7C:
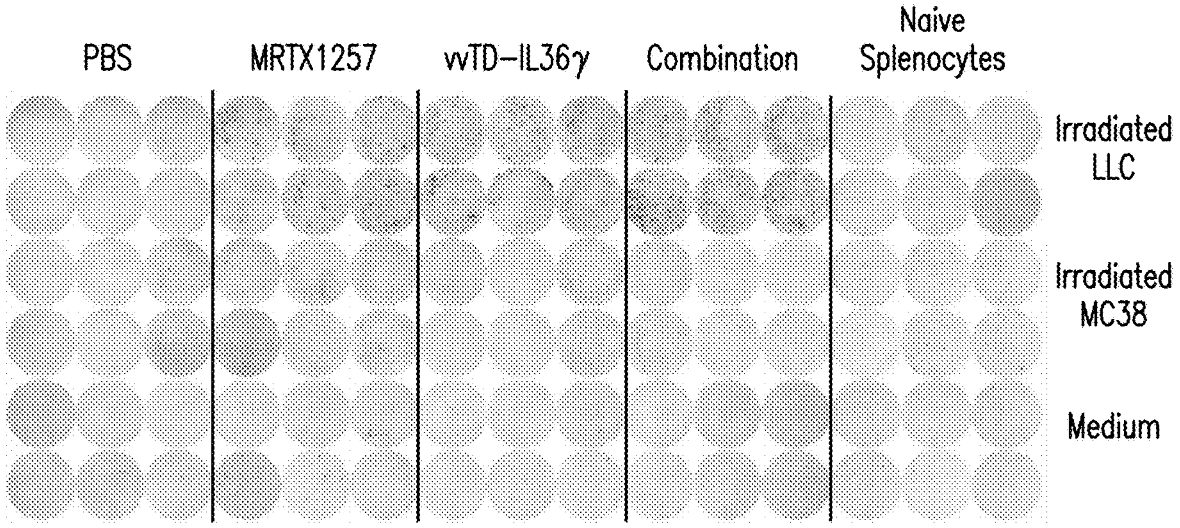
Figure 7D:
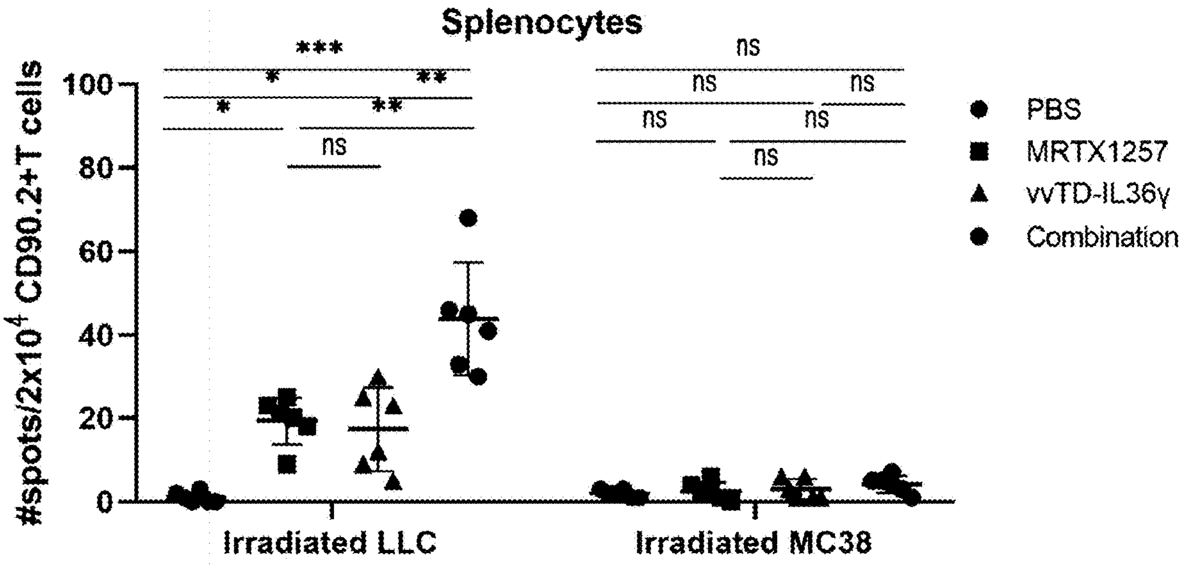
Figure 7E:
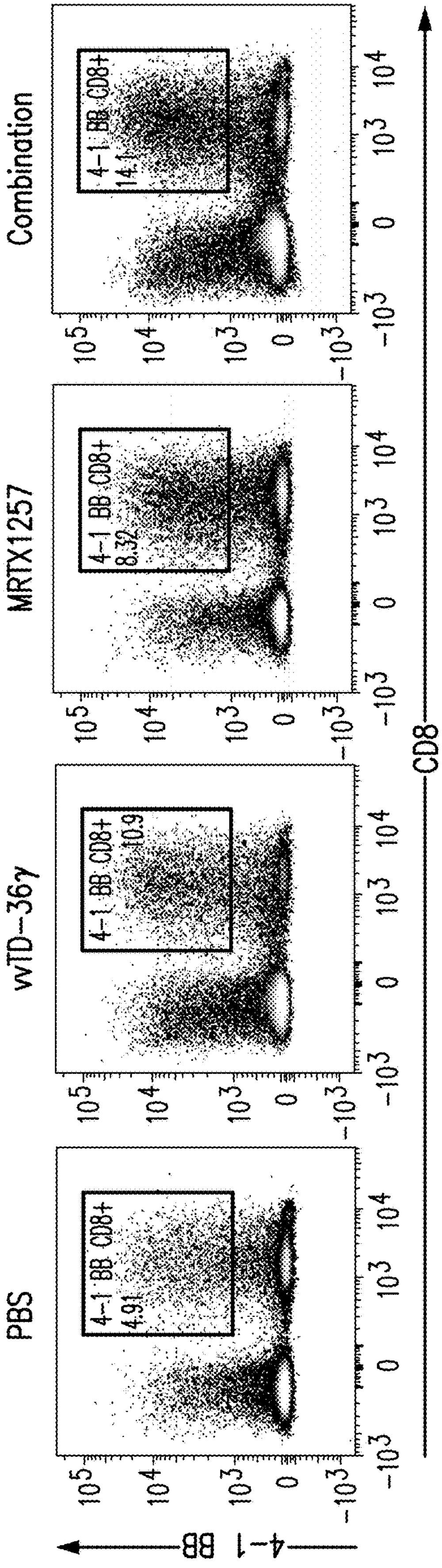
Figure 7F:
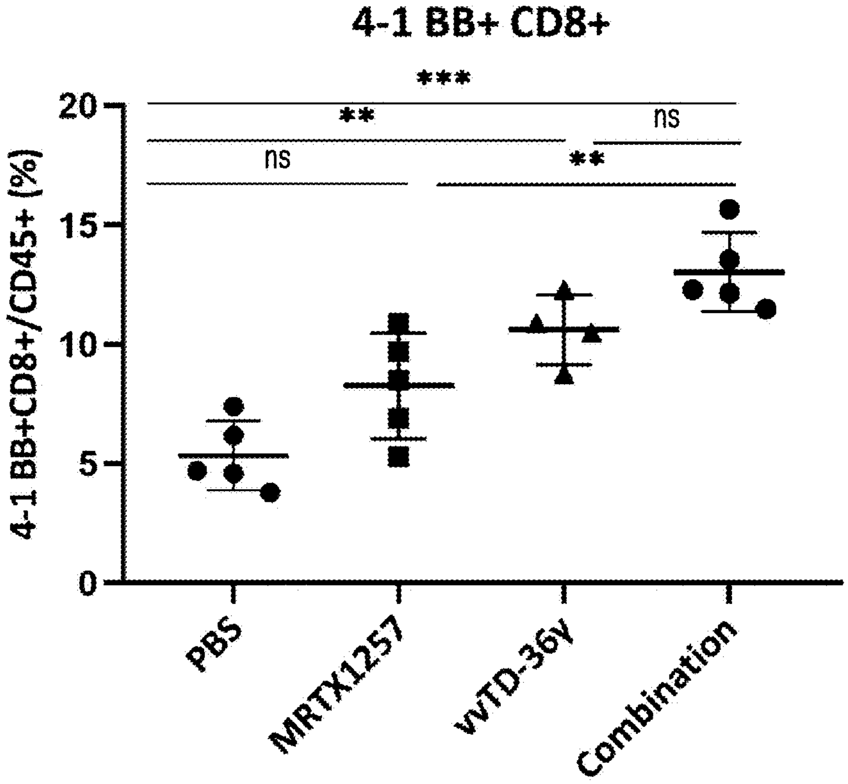
Figure 7G:
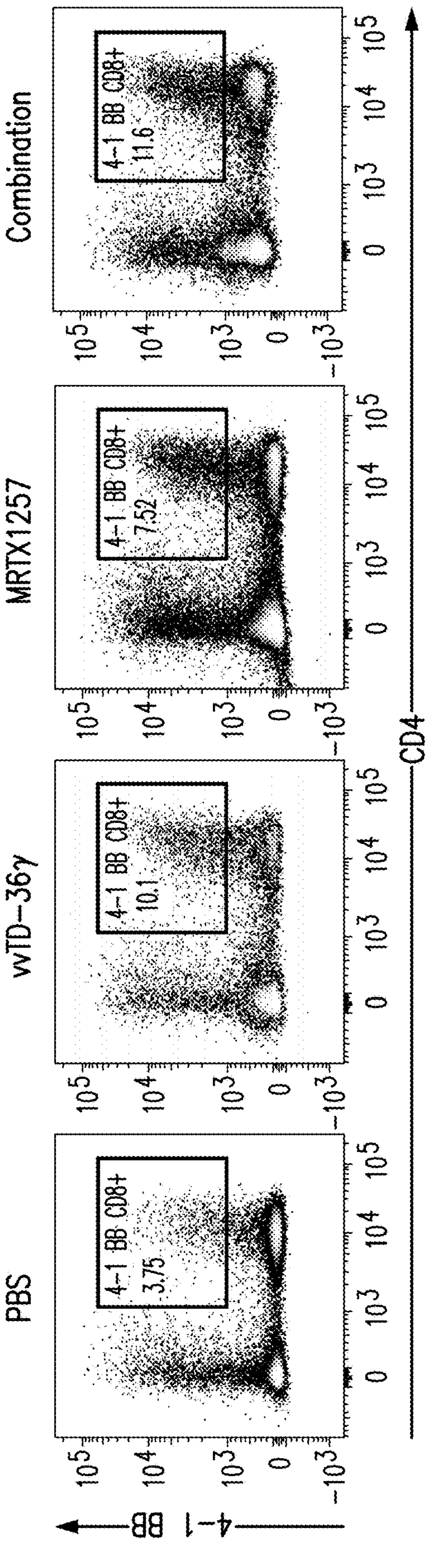
Figure 7H:
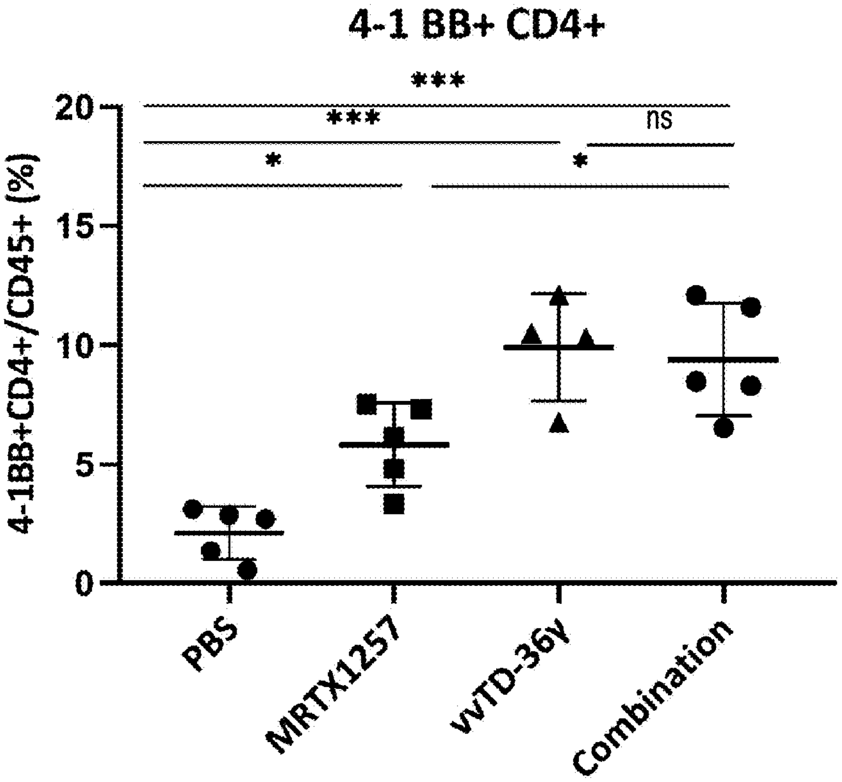
Figure 8A:
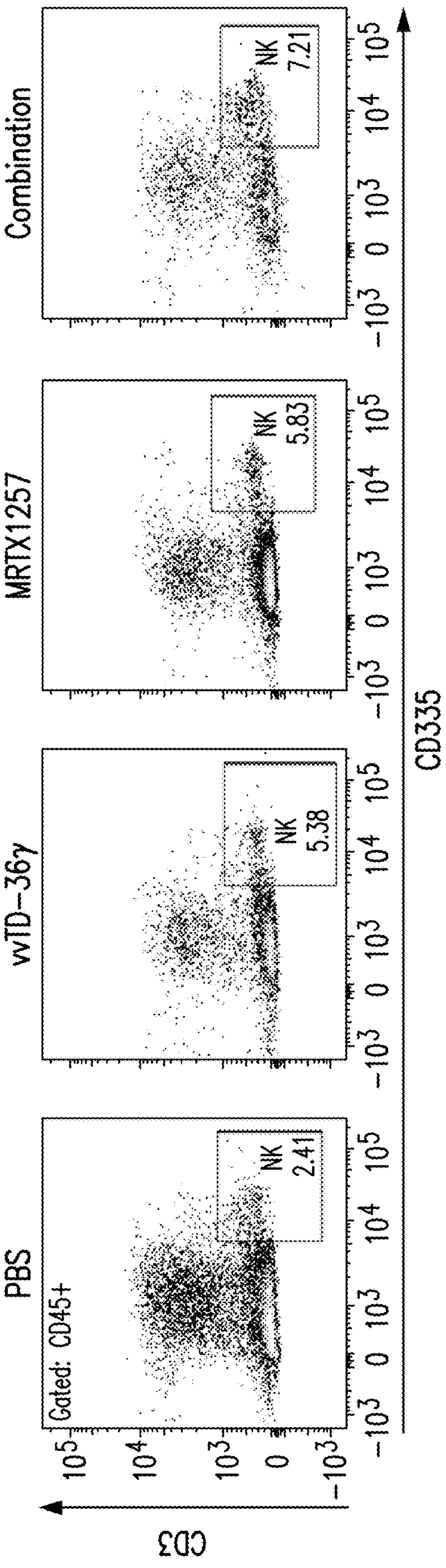
FIGS. 8A-8L illustrate representative flow cytometric analysis of percentages of TILs 6 days post-treatment.
Figure 8B:
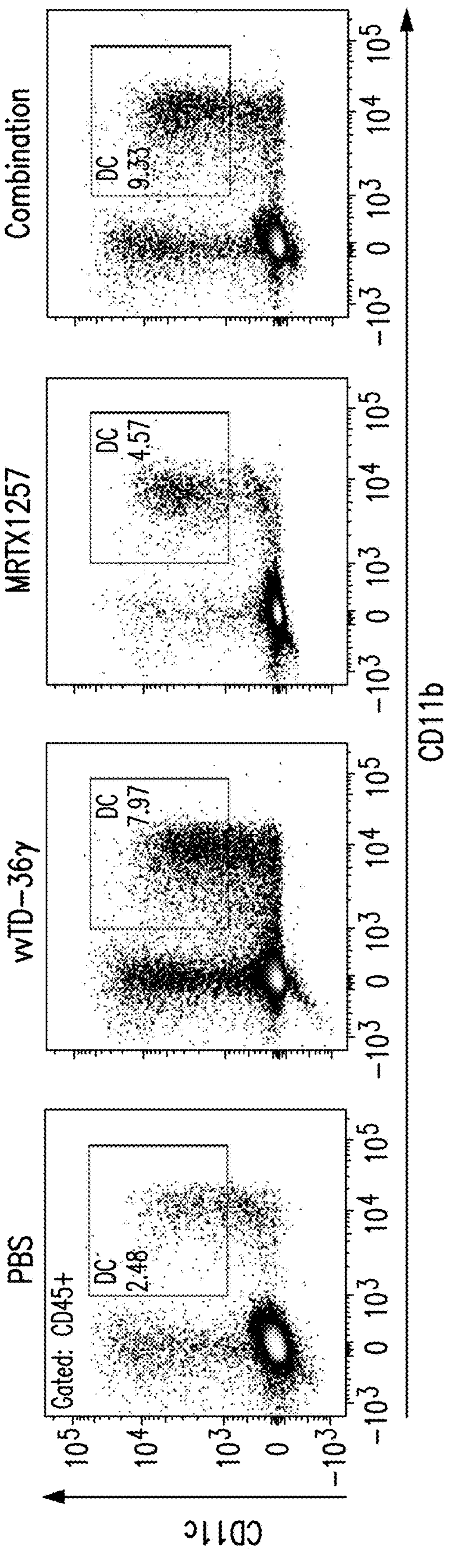
Figure 8C:
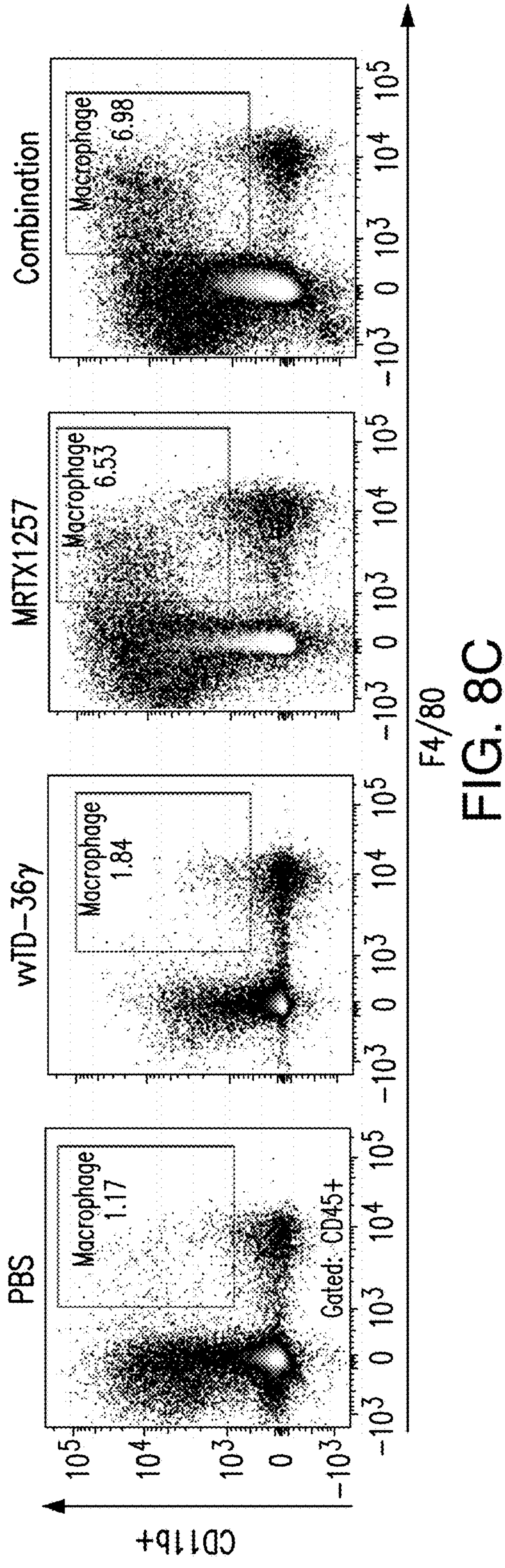
Figure 8D:
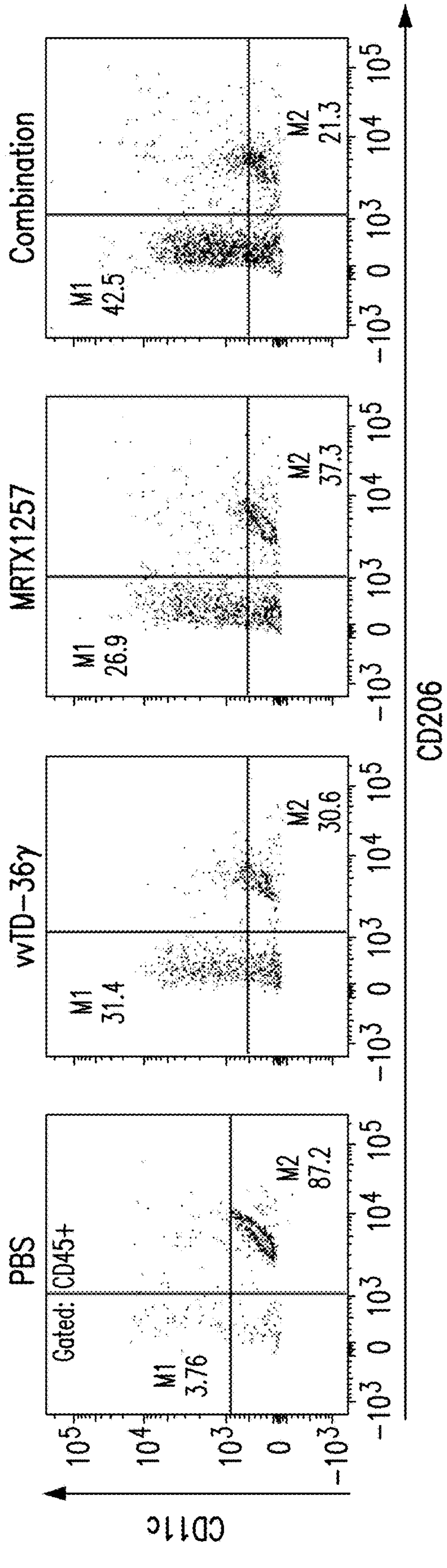
Figure 8E:
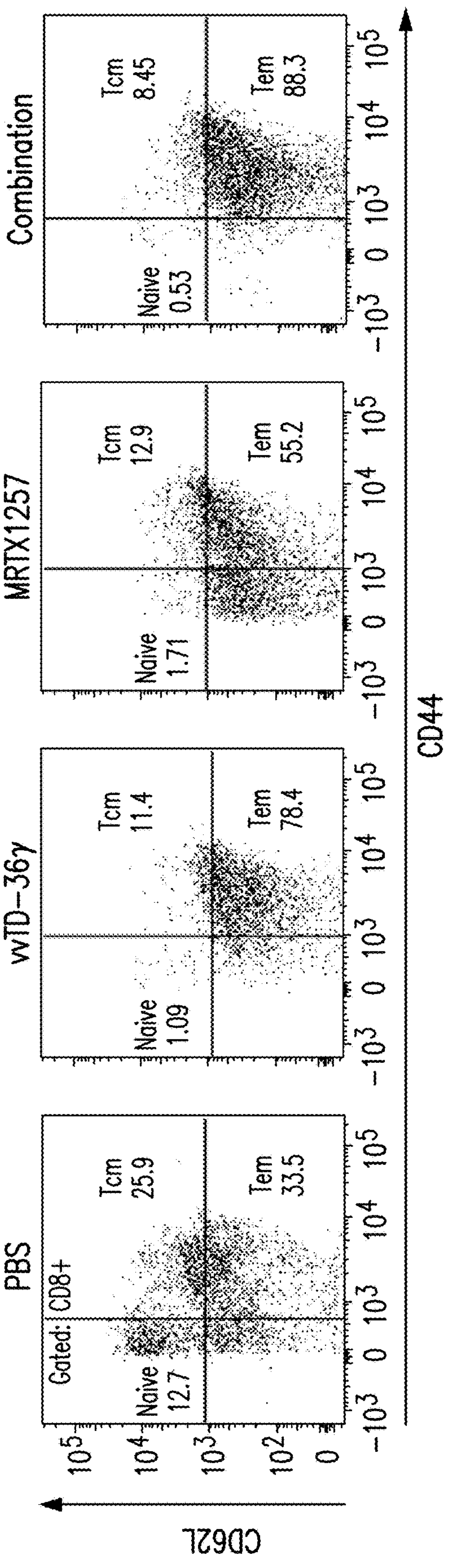
Figure 8F:
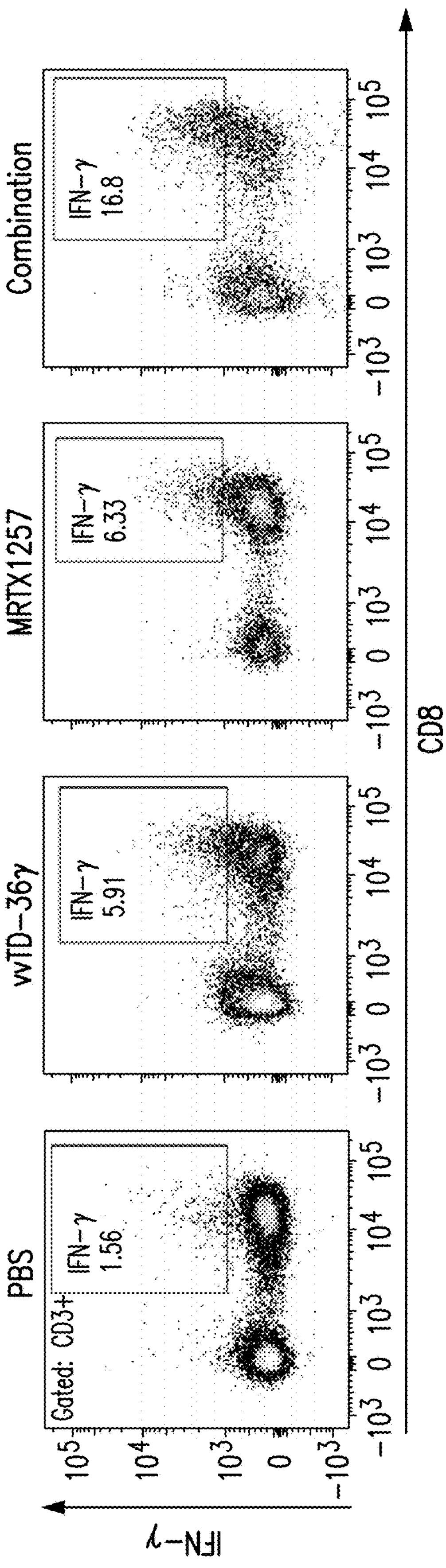
Figures 8G, 8H:
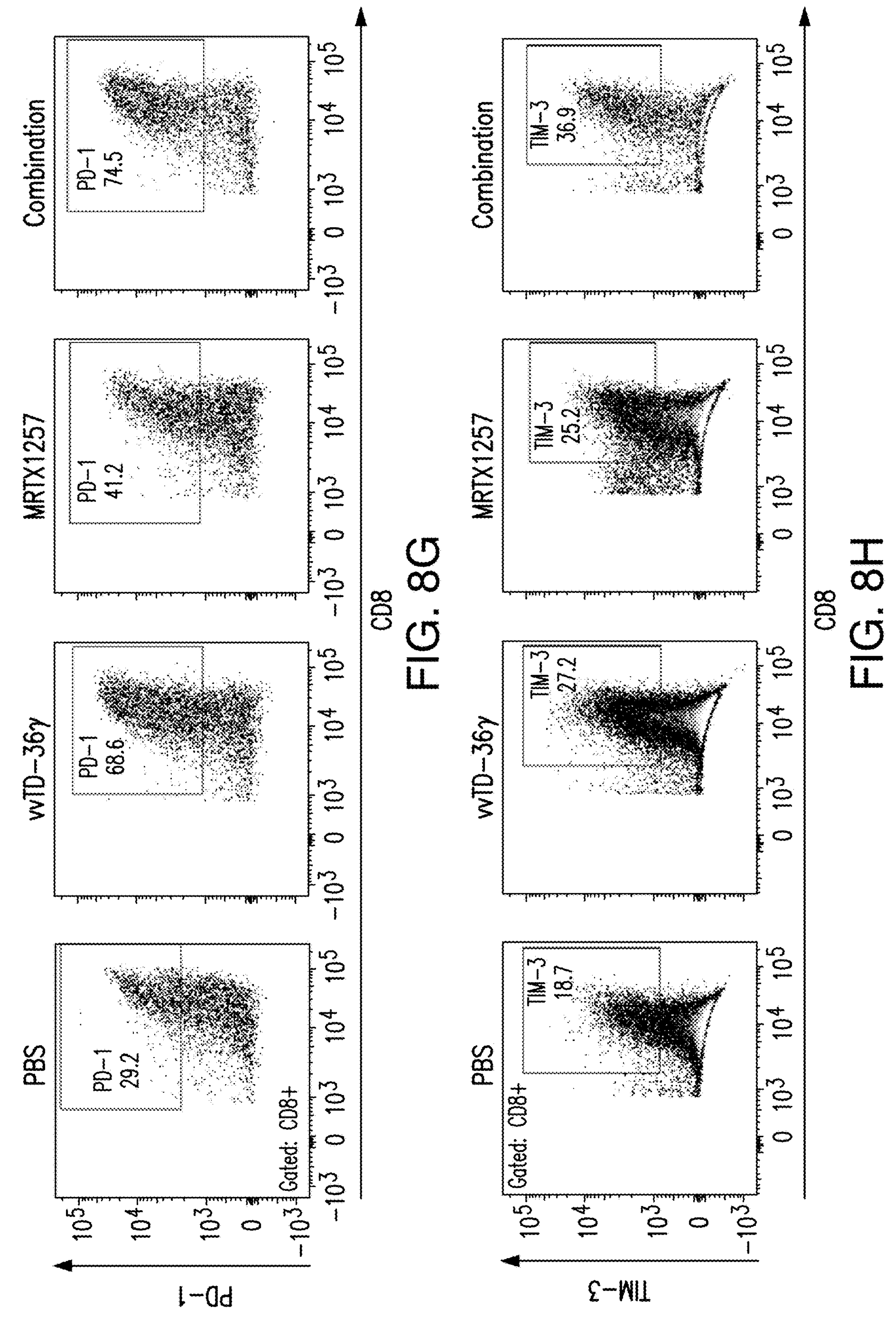
Figure 8I:
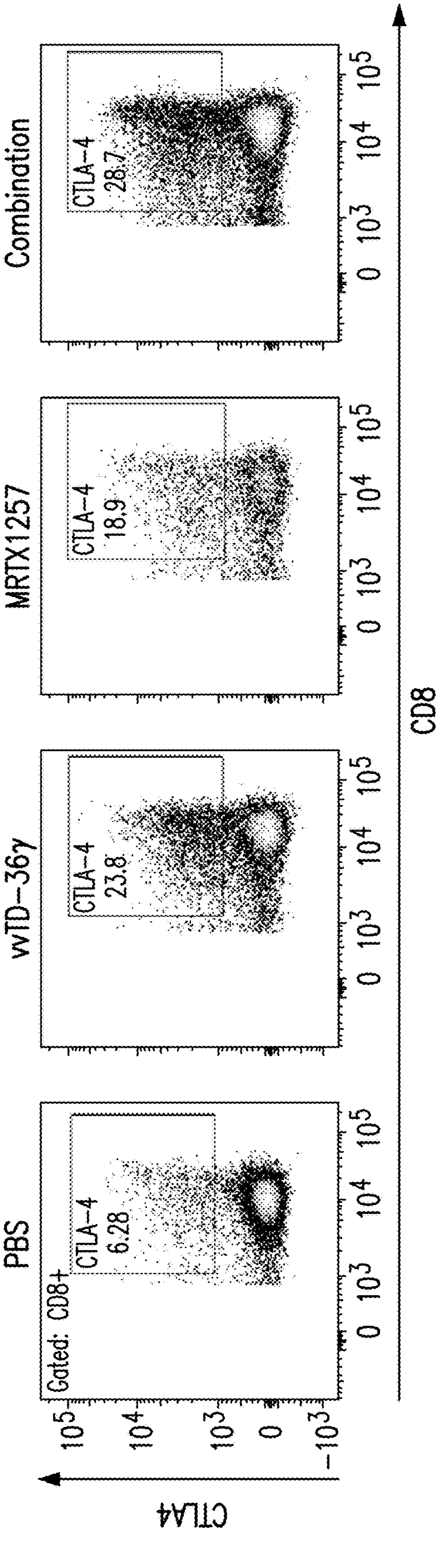
Figure 8J:
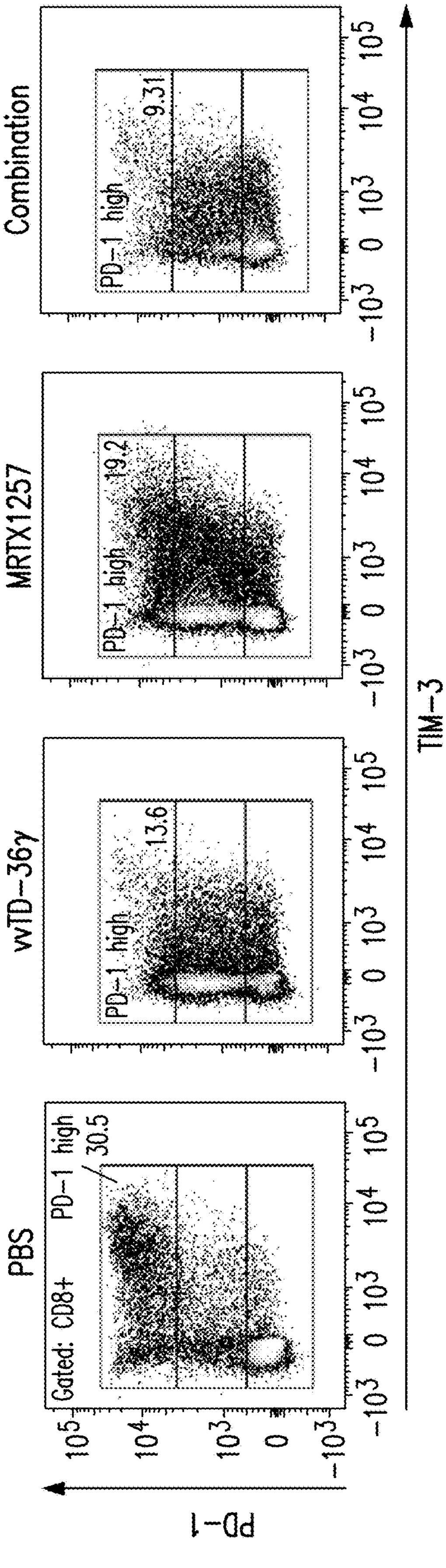
Figures 8K, 8L:
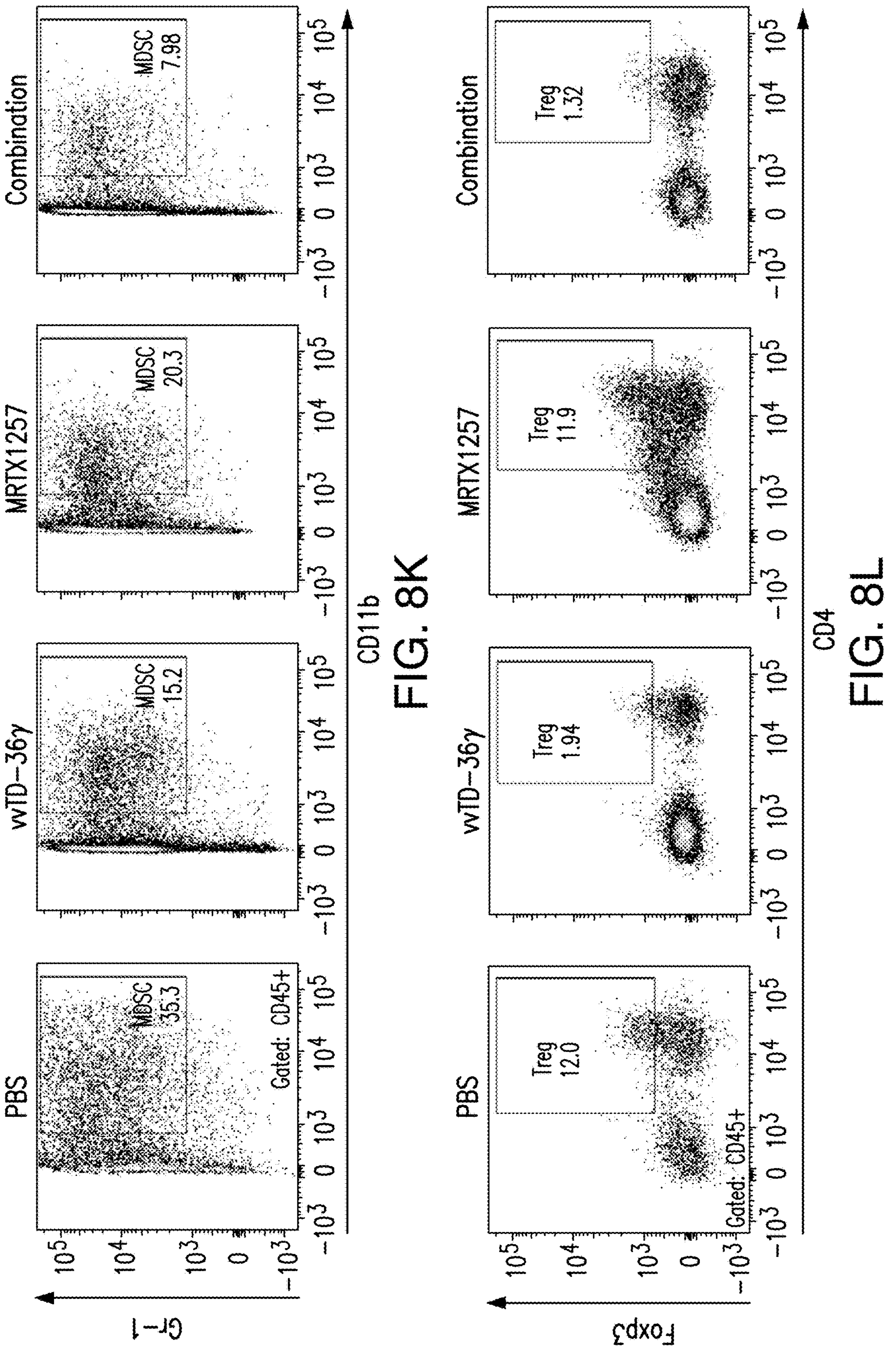

ELISpot assays were also performed with T cells isolated from splenocytes. The number of spots was at least 10-fold lower even though the patterns looked similar (FIGS. 7C-7D). These results indicated that tumor-specific T cells were enriched in the tumor tissues.

4-1BB expressed on the surface of T cells have been shown to be an activated marker for T cells. Therefore, the quantities of 4-1BB+CD4+ and 4-1BB+ CD8+ T cells were determined (FIGS. 7E-7H). A statistically significant increase of 4-1BB+ CD8+ T cells was observed in both monotherapy groups and a trend to increase was observed in dual therapy group ($p<0.01$ compared to PBS). 4-1BB+ CD4+ T cells also increased in all three treated groups ($p<0.05$ compared to PBS). Together, these results strongly indicated that, just like the potent OV, MRTX1257 can also elicit potent antitumor immunity. The combination works synergistically to elicit more optimal tumor-specific immunity for improved therapeutic efficacy.

Discussion:

Immune cell infiltration in the tumor impacts tumor progression and patient survival, and a strong lymphocyte infiltration has been reported to be associated with an antitumor response and improved clinical outcome in a variety of types of cancers, including colorectal cancer and lung cancer. The majority of solid tumors, especially those of low tumor mutational burden (TMB), however, lack an inflammatory infiltrate.

Cancers develop immune escape mechanisms to avoid detection by effector immune cells. This includes cell surface expression of immune system checkpoint ligands such as PD-L1. The immunosuppressive tumor microenvironment includes immunosuppressive macrophages, myeloid-derived suppressor cells and regulatory T cells interfering with an efficient anti-tumor T cell response. Inhibitory checkpoint molecules such as CTLA-4, PD-1, TIM-3, LAG3, are unregulated in chronically stimulated T cells, promoting T cell energy. Therefore, an effective cancer immunotherapy strategy would need to consider the factors of not only killing the tumor cells (oncolysis), but also improving the trafficking of immune cells to the tumor tissue, activation and proliferation of tumor-specific T cells and sustained activity of these antitumor immune cells. Pro-inflammatory cytokine-armed oncolytic viruses (OVs) have been shown to promote not only the trafficking, but also the activation of tumor-specific T cells, thus enhancing adaptive antitumor immunity. However, due to the fact that the highly immunosuppressive TME paralyzes the functions of T cells, often the OV itself is not potent enough to turn the corner, making it pro-antitumoral environment. Therefore, it is strategic to form combinations with other antitumor regimens that act synergistically by eliciting potent and sustained adaptive antitumor immunity.

In the present example, it was hypothesized that it is rational to combine a small molecule inhibitor to the driver oncoprotein KRASG12C with a potent OV for improved therapeutic efficacy on KRASG12C cancers. One such small molecule inhibitor (AMG510) has been shown recently to induce inflammation in cancer tissue. Surprinsingly, such an inhibitor by itself can induce potent innate and adaptive antitumor immunity. For innate immune cells, it increases the quantities of NKs, DCs, and M1 macrophages while decreasing M2 macrophages. As for the subsets of CD8+ T cells, it promotes the conversion from Tn, Tcm to Tem, and effector T cells. Even though it increases the expression of CTLA-4, PD-1, and TIM-3 on CD8+ T cells, it reduces PD-1hiTIM-3+CD8+ T cells, the terminally exhausted cells, in the TME (FIGS. 5A-5O). Further analyses showed that it can increase the quantities of CD8+ and CD4+ T cells in the tumor tissues, and NKG2D, granzyme B, and IFN-γ activation markers on those cytotoxic cells (FIGS. 4A-4I). Finally, ELISpot assays clearly demonstrated that this small molecule can induce tumor-specific T cells in LLC (FIGS. 7A-7H). In summary, these data show that MRTX1257 induces tumor-specific T cells in the LLC model.

In the present example, studies were performed with an OV expressing IL36 in KRASG12C cancer models. For the profile of innate immune cells, just like the small molecule, the OV increased the quantities of NKs, DCs, and M1 macrophages. More dramatically, the OV decreased M2 macrophages, MDSCs, and Tregs, all three major types of cells inhibiting the antitumoral immune response. Further analyses showed that it can increase the quantities of CD8+ and CD4+ T cells in the tumor tissues, and NKG2D, granzyme B, and IFN-γ activation markers on those cytotoxic cells (FIGS. 4A-4I). For CD8+ T cell subsets, the OV promotes the conversion from Tn, Tcm to Tem, and effector T cells. Even though it enhances CTLA-4, PD-1, and TIM-3 on CD8+ T cells, it reduces PD-1hiTIM-3+CD8+ T cells in the TME (FIGS. 5A-5O). Finally, the induction of tumor-specific T cells was shown in ELISpot assays with both TILs and splenocytes, and for 4-1BB+CD4+ and 4-1BB+CD8+ T cells by flow cytometry.

Next, it was tested whether the combination of a specific inhibitor to KRASG12C and an oncolytic virus expressing IL-36 would work synergistically. Indeed, the data disclosed herein show that combination of the OV and MRTX1257 led to more potent pro-immune properties against cancer.

Next, it was evaluated whether addition of an anti-PD-1 blockade to the regimen would further improve the therapeutic effect. Analyses using flow cytometry and qRT-PCR indicated improved levels of innate immune cells (NKs, DCs, and M1 macrophages), both CD4 and CD8 T cells, and activation markers (NKG2D, granzyme B, IFN-γ, and 4-1BB), and further reduced levels of M2 macrophages, MDSCs, and Tregs. These changes led to further enhanced antitumor T cells intratumorally and systemically, as shown by ELISpot assays with TILs and splenocytes. Finally, the improved antitumor potency converts to the best therapeutic efficacy, leading to complete remission of LLC tumors in the majority of treated mice. This therapeutic efficacy depends heavily on CD8+ T cells, and to a smaller degree on CD4+ T and NK cells.

Combination therapies using regimens integrating immunocheckpoint inhibitors (ICIs) or small molecule inhibitor to a specific oncogenic driver protein like MRTX1257 and OV are attractive, as an OV can execute oncolysis and trigger the release/presentation of tumor associated antigens, danger signals, and pro-inflammatory cytokines, leading to increased T cell recruitment and activation of immune cells, including T cells. Viral infection also increases the expression of PD-1/PD-L1, CTLA-4, TIM3, and other immune checkpoint molecules. The latter become the targets of ICIs for improved T cell activity and therapeutic efficacy. As demonstrated in this example, the triple combination led to complete regression of tumors in the KRASG12C mutant tumor model.

In summary, the present example demonstrated that IL-36γ armed OV promotes T cell infiltration and enhances the population of tumor-reactive TILs in a murine colon cancer model. The present example provides a new therapeutic strategy to promote the generation and infiltration of tumor-reactive TILs in lowly or poorly immunogenic tumors and the expansion of such TILs for ACT. This new strategy can be translated into a clinical application and can allow adoptive T cell therapy for an expanded group of cancer patients.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

What is claimed is:

1. A method for treating a cancer in a subject in need thereof, comprising administering a therapeutically effective amount of a KRAS inhibitor and a therapeutically effective amount of an oncolytic virus to the subject, wherein the oncolytic virus comprises a nucleic acid molecule encoding interleukin-36γ (IL-36γ).

2. The method of claim 1, wherein the IL-36γ comprises an amino acid sequence that is at least 80% identical to the amino acid sequence set forth in SEQ ID NO: 1 or SEQ ID NO: 1.

3. The method of claim 1, wherein the nucleic acid molecule: (a) is an exogenous nucleic acid molecule; (b) is integrated into the genome of the oncolytic virus; (c) is a DNA molecule; (d) is operably linked to a promoter; and/or (e) is integrated into the locus of the J2R gene.

4. The method of claim 1, wherein the oncolytic virus is an oncolytic vaccinia virus, wherein the oncolytic vaccinia virus: (a) lacks the expression of a functional thymidine kinase (TK), a functional vaccinia growth factor (VGF), a functional serine proteinase inhibitor 1 (SPI-1), a functional serine proteinase inhibitor 2 (SPI-2), or a combination thereof; (b) comprises a mutation of the J2R gene, a mutation of the C11R gene, a mutation of the B22R gene, a mutation of the B13R gene, or a combination thereof; and/or (c) is a Western Reserve strain.

5. The method of claim 1, further comprising administering an immunomodulatory agent to the subject.

6. The method of claim 5, wherein the immunomodulatory agent is selected from the group consisting of immune checkpoint inhibitors, T cells, dendritic cells, therapeutic antibodies, cancer vaccines, cytokines, Bacillus Calmette-Guérin (BCG), and a combination thereof.

7. The method of claim 1, wherein the method improves the anti-cancer adaptive immune response in the subject; or wherein the method promotes the immunogenicity of a tumor microenvironment of the subject.

8. The method of claim 1, wherein the cancer is selected from the group consisting of adenocarcinomas, osteosarcomas, cervical carcinomas, melanomas, hepatocellular carcinomas, breast cancers, lung cancers, prostate cancers, ovarian cancers, leukemia, lymphomas, renal carcinomas, pancreatic cancers, gastric cancers, colon cancers, duodenal cancers, glioblastoma multiforme, astrocytomas, sarcomas, and a combination thereof.

9. The method of claim 1, wherein the KRAS inhibitor comprises KRpep-2d, lonafarnib, BI-3406, BAY-293, BI-2852, oncrasin-1, MRTX849, MRTX1257, K-Ras-IN-1, sotorasib, AMG510, ARS-1620, fendiline hydrochloride, deltarasin, K-Ras inhibitor 9, K-Ras inhibitor 6, K-Ras inhibitor 12, 6H05, a salt thereof, a derivative thereof, or a combination thereof.

10. The method of claim 1, wherein the KRAS inhibitor is administered to the subject at a dose from about 0.05 mg/kg to about 100 mg/kg, and wherein the oncolytic virus is administered to the subject at a dose from about $10^5$ and $10^{10}$ plaque forming units (PFU).

* * * * *